United States Patent [19]
Franconi et al.

[11] Patent Number: 5,186,181
[45] Date of Patent: Feb. 16, 1993

[54] RADIO FREQUENCY THERMOTHERAPY

[76] Inventors: Cafiero Franconi, 23, Via Sant'Erasmo, 00184 Rome, Italy; Jan Vrba, 2, Durerova, 100 00 Prague 10, Czechoslovakia

[21] Appl. No.: 558,670

[22] Filed: Jul. 27, 1990

[51] Int. Cl.$^5$ .............................................. A61N 5/00
[52] U.S. Cl. ..................................... 128/804; 128/399
[58] Field of Search .................................. 128/804, 399

[56] References Cited

U.S. PATENT DOCUMENTS

| | | | |
|---|---|---|---|
| 3,065,752 | 11/1962 | Potzl | 128/804 X |
| 4,108,147 | 8/1978 | Kantor | 128/804 |
| 4,282,887 | 8/1981 | Sterzer | 128/804 |
| 4,690,156 | 9/1987 | Kikuchi et al. | 128/804 |

FOREIGN PATENT DOCUMENTS

| | | | |
|---|---|---|---|
| 0036040 | 9/1981 | European Pat. Off. | 128/804 |
| 0221373 | 4/1985 | Fed. Rep. of Germany | 128/804 |
| 2135891 | 9/1984 | United Kingdom | 128/804 |

OTHER PUBLICATIONS

Assenheim et al, "A Diathermy Applicator . . . ", IEEE Trans Biomed Eng, vol. BME 27, No. 8, Aug. 1980, pp. 476–479.

Primary Examiner—Lee S. Cohen
Attorney, Agent, or Firm—John S. Hale

[57] ABSTRACT

An electromagnetic applicator for use in hyperthermic treatments of superficial and subcutaneous tissues employing radiators integrated in a waveguide segment which is working below the cutoff frequency and supports evanscent modes of propagation which are excited by the radiators to produce a multi-modal field of controlled intensity. Additional radiators are integrated in the same waveguide to generate directly another controlled field. The multi-modal and directly emitted field are generated with a large variety of field sizes, shapes and penetration features and are combined in many ways and in any power level ratio to provide a heating field emerging from the waveguide aperture which impinges upon tissue to be heated through a noncritical air gap thereby allowing heating of a large variety of subcutaneous tumors to temperatures causing tumor necrosis without injury to the normal fat and other access tissues. Moreover, palliative treatments may be performed on subcutaneous muscle tissues and joints and on hypertrophic tissues.

39 Claims, 20 Drawing Sheets

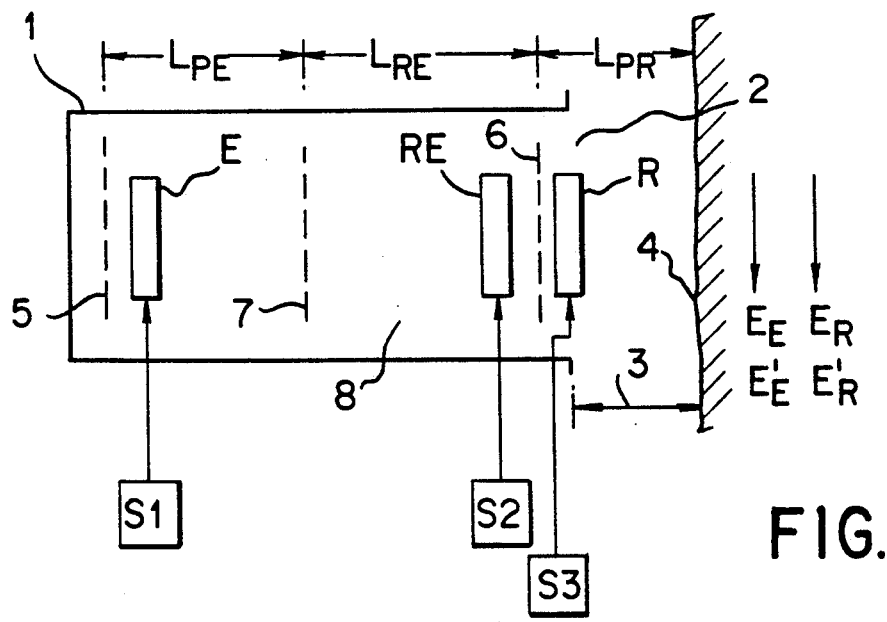
FIG. 1G
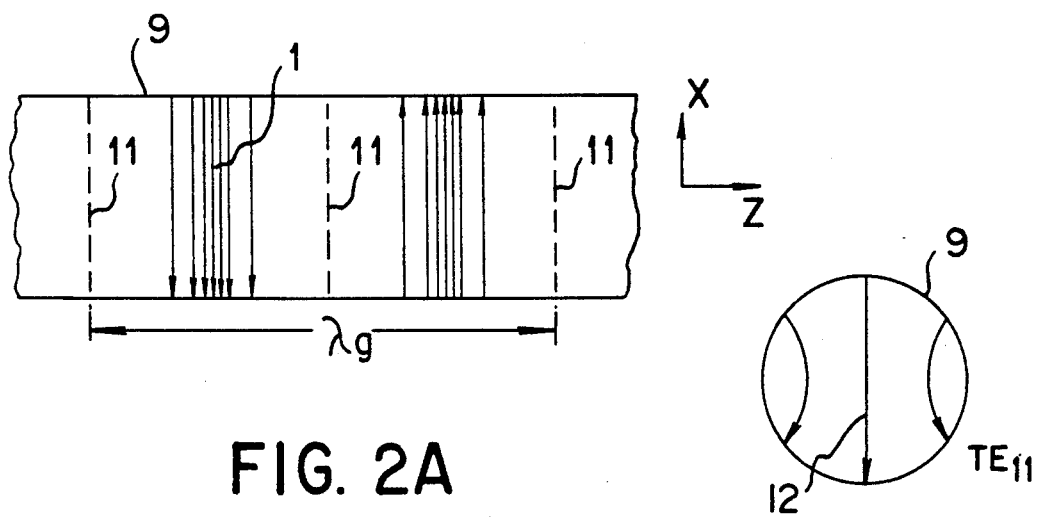
FIG. 2A
FIG. 2B
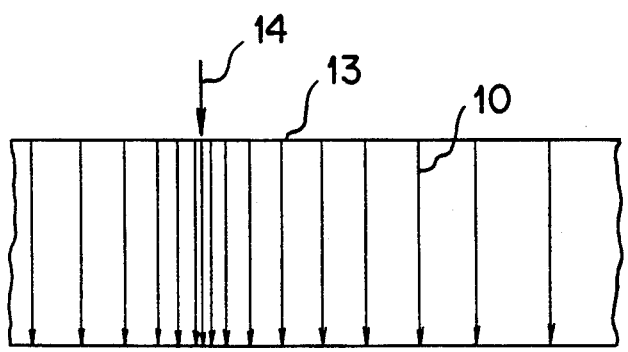
FIG. 3A

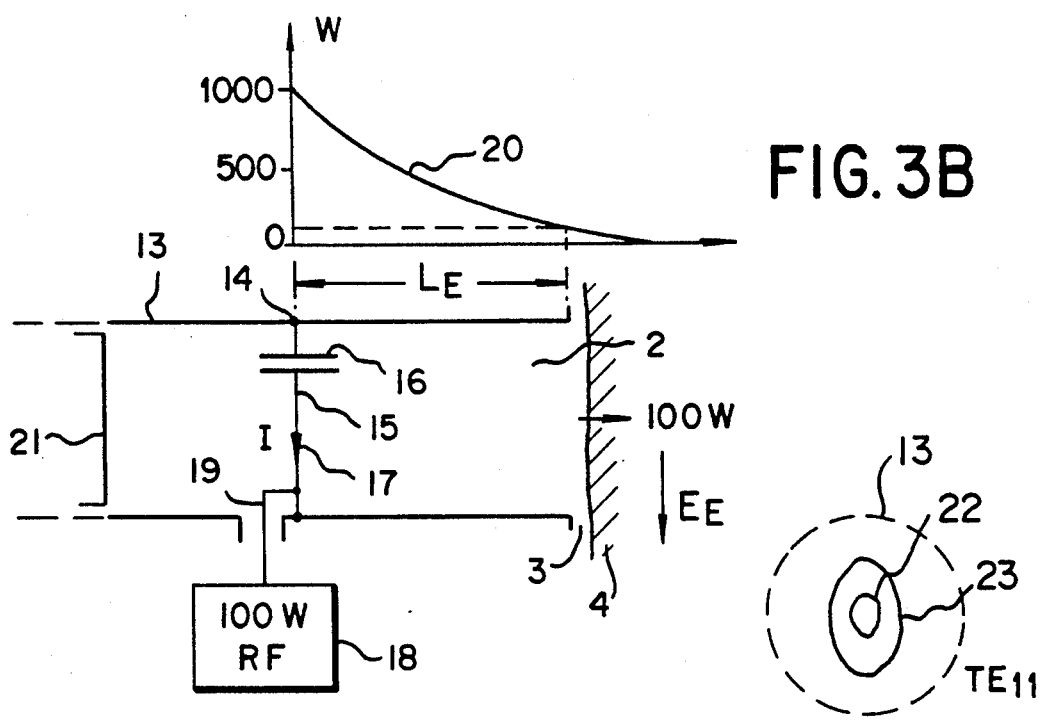
FIG. 3B
FIG. 4
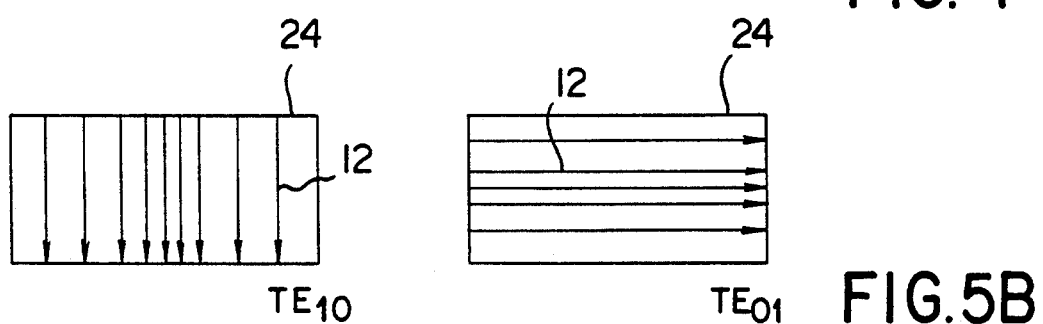
FIG. 5A
FIG. 5B
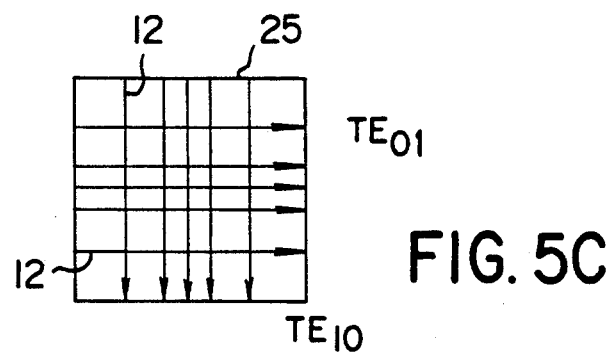
FIG. 5C
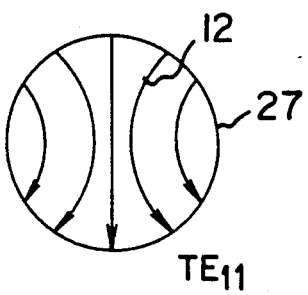
FIG. 5D

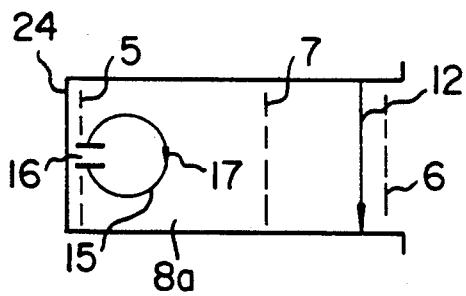
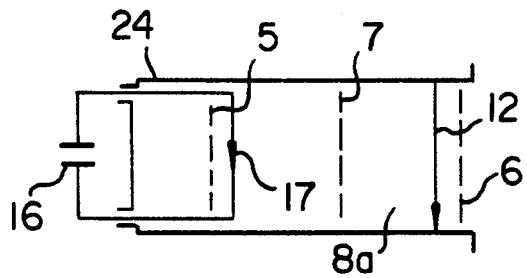
FIG. 6C  FIG.6D
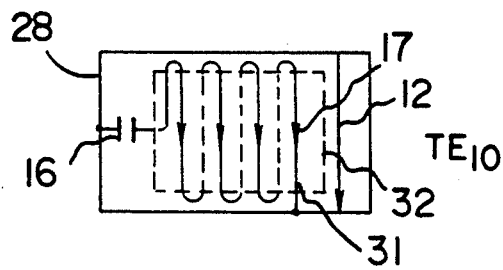
FIG. 7
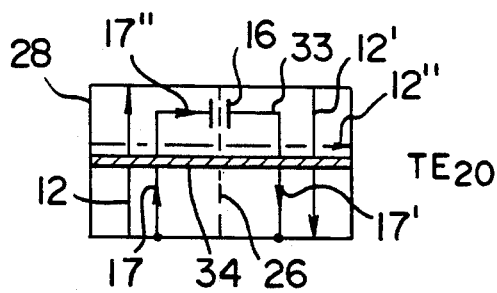
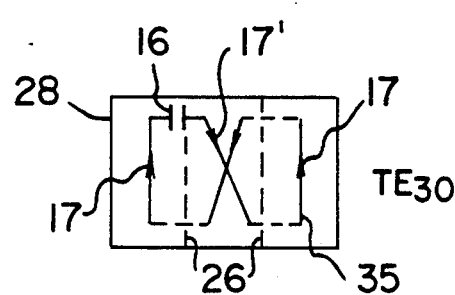
FIG. 8A  FIG.8B
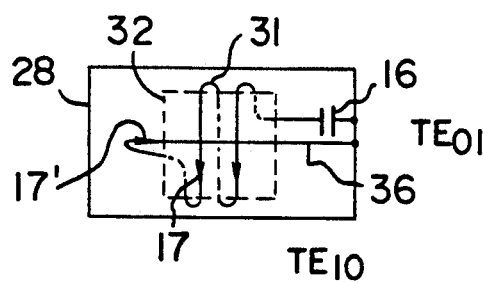
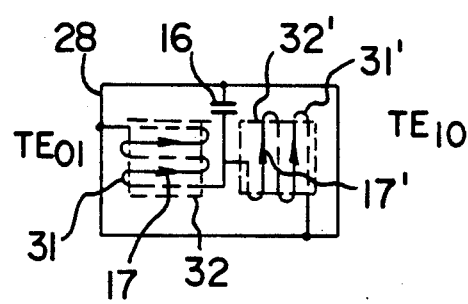
FIG. 9A  FIG.9B

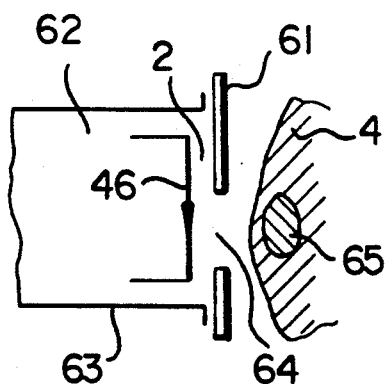
FIG. 20A
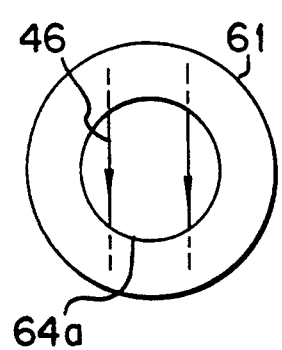
FIG. 20B
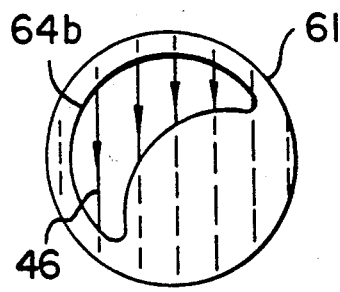
FIG. 20C
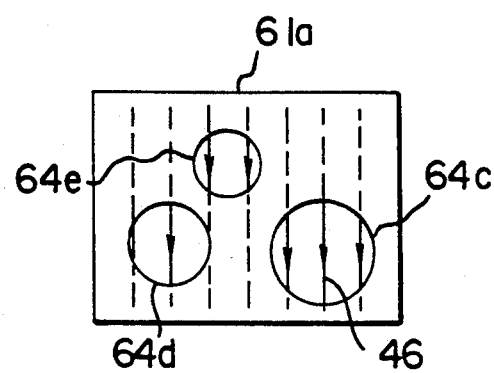
FIG. 20D
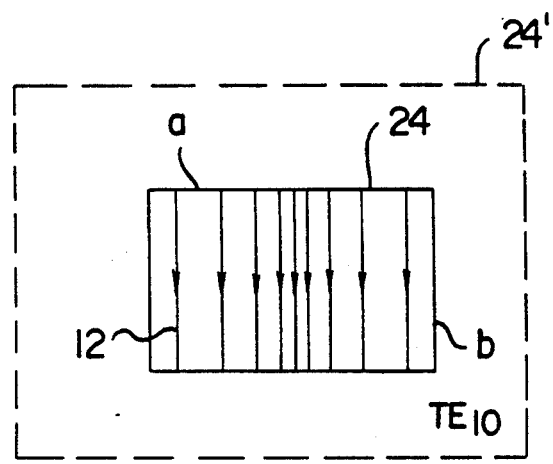
FIG. 20E
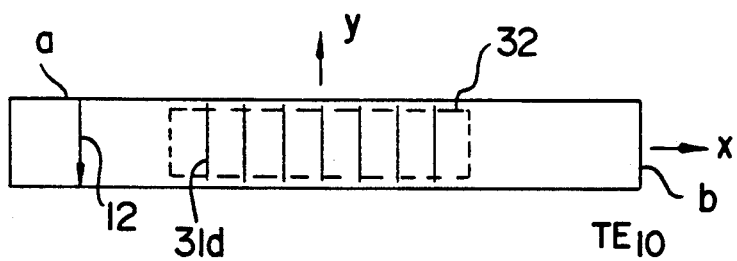
FIG. 20F
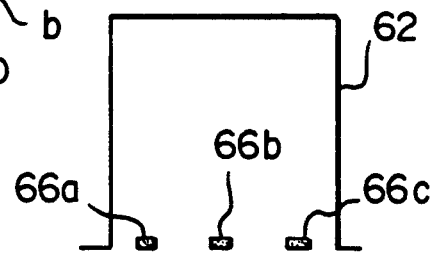
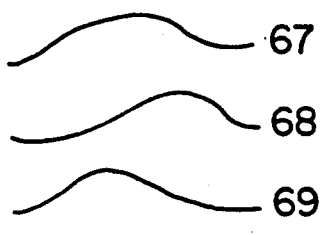
FIG. 21

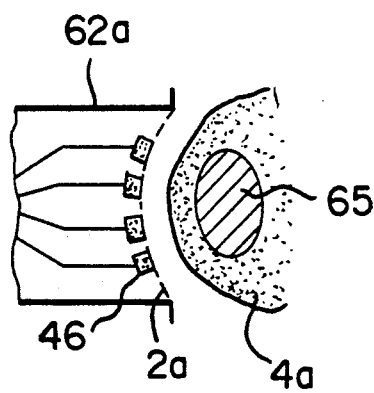
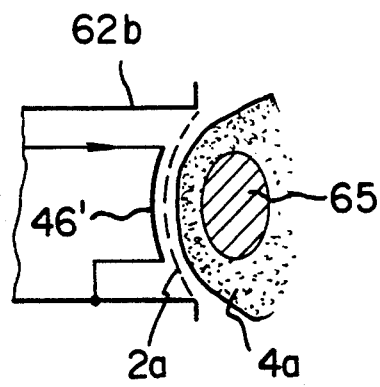
FIG. 22A  FIG. 22B
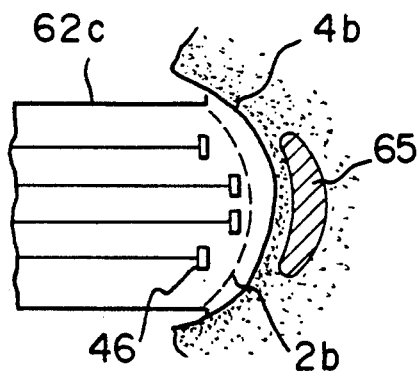
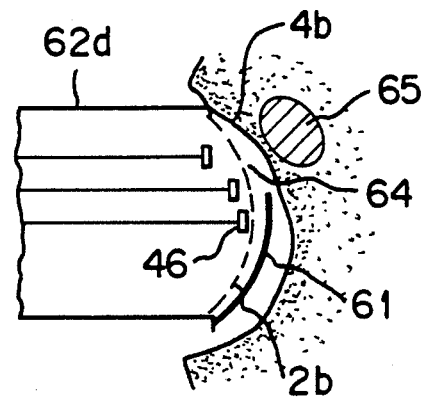
FIG. 23  FIG. 24
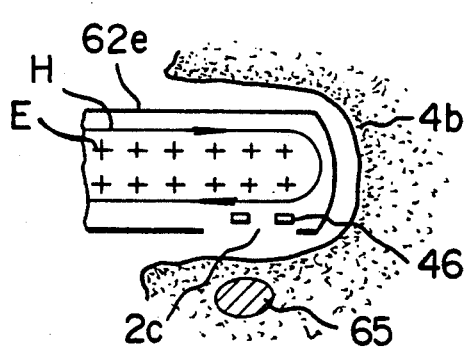
FIG. 25
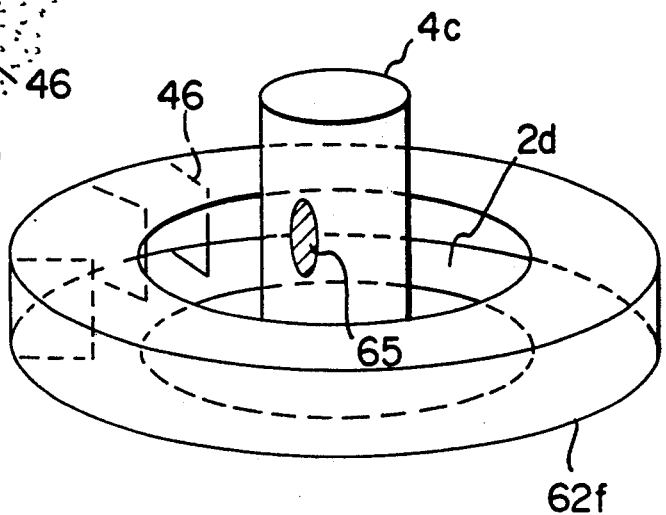
FIG. 26

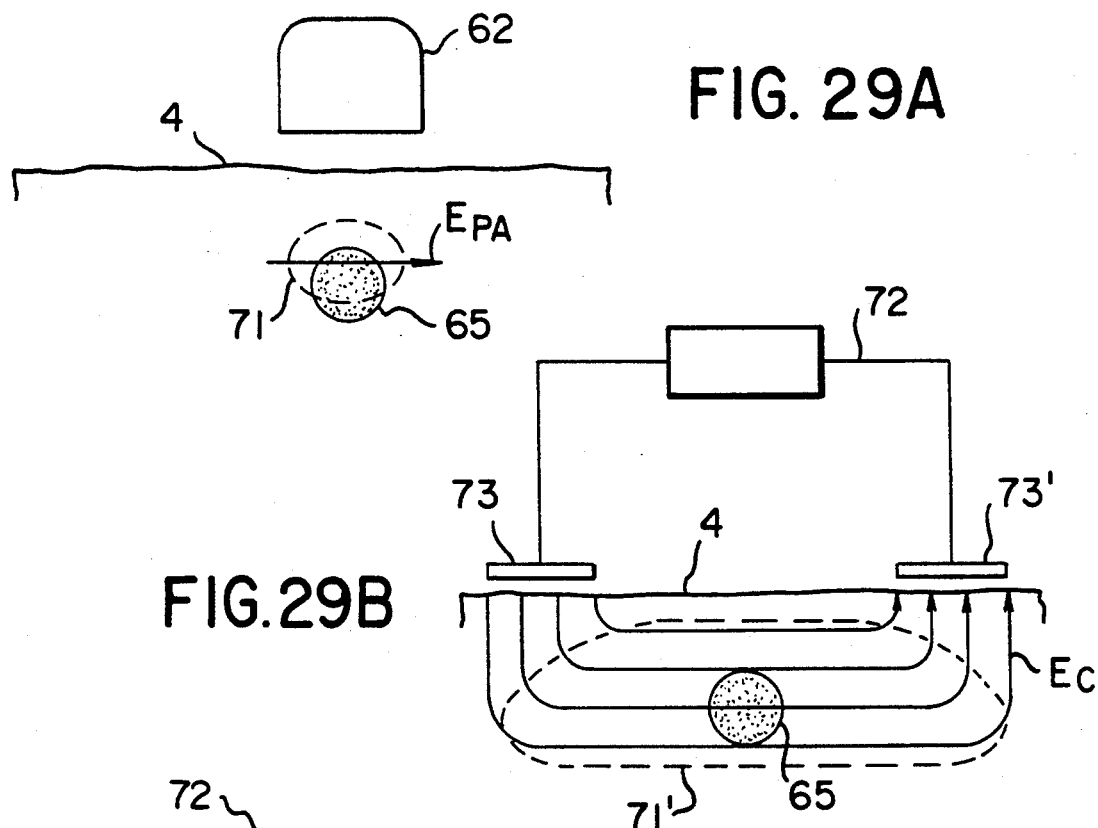
FIG. 29A
FIG. 29B
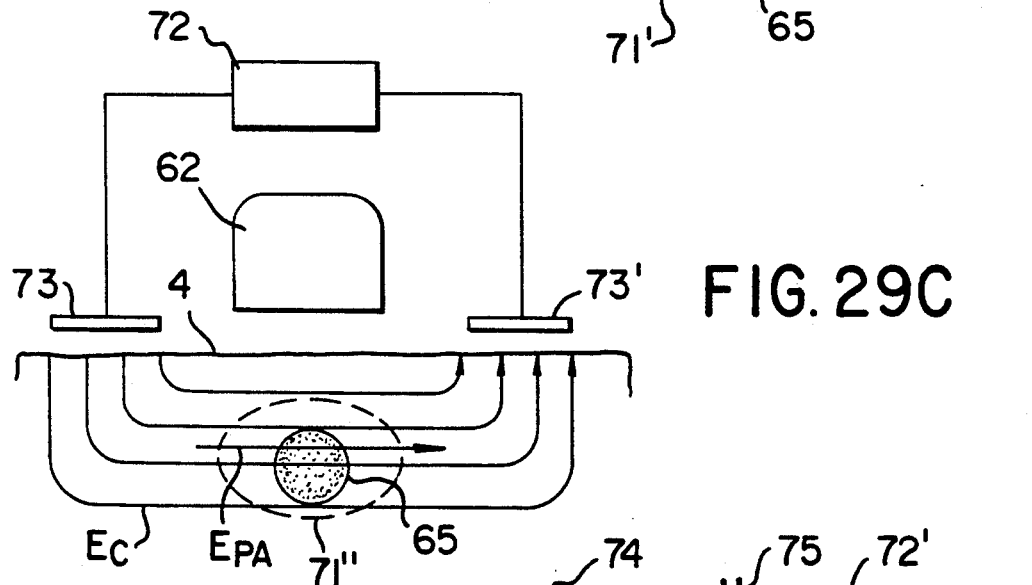
FIG. 29C
FIG. 29D
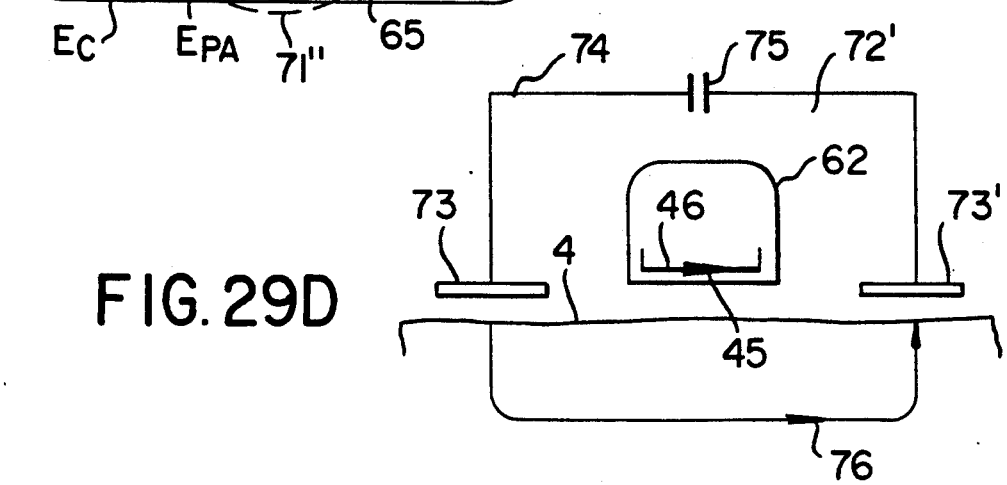

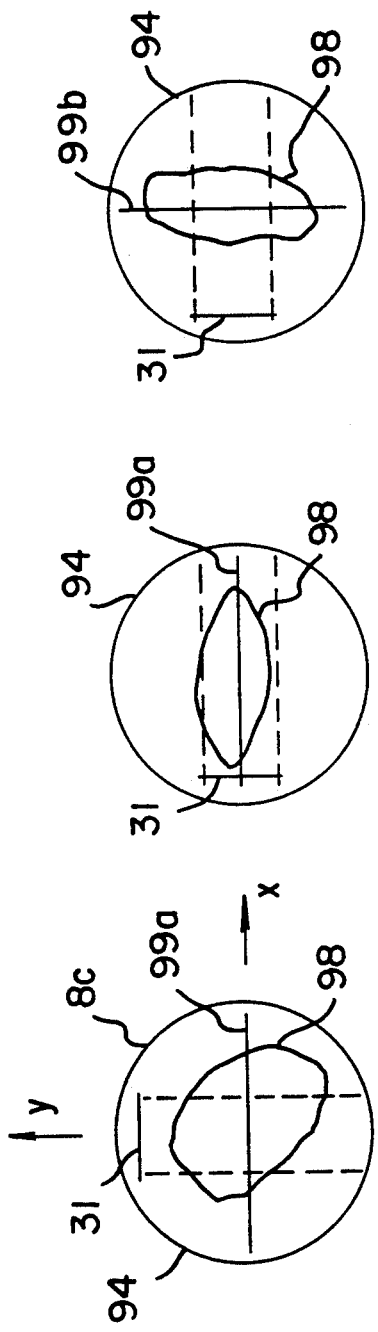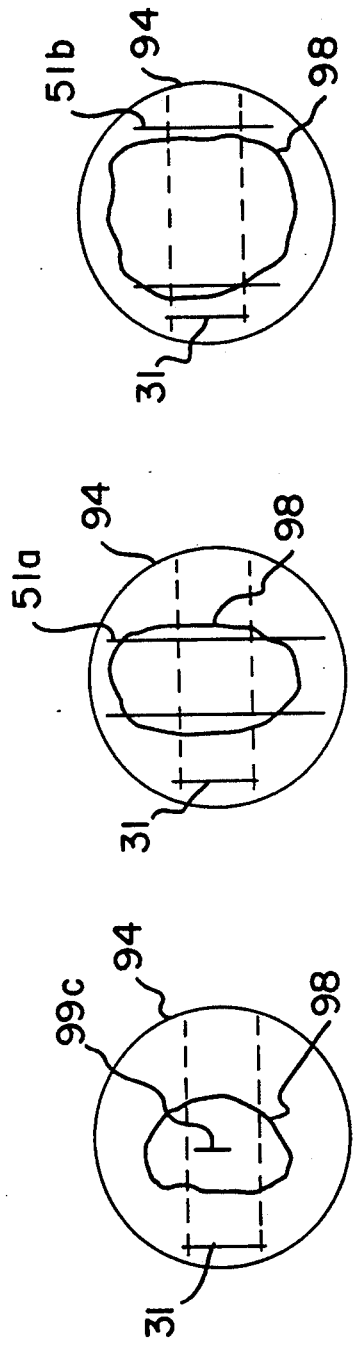

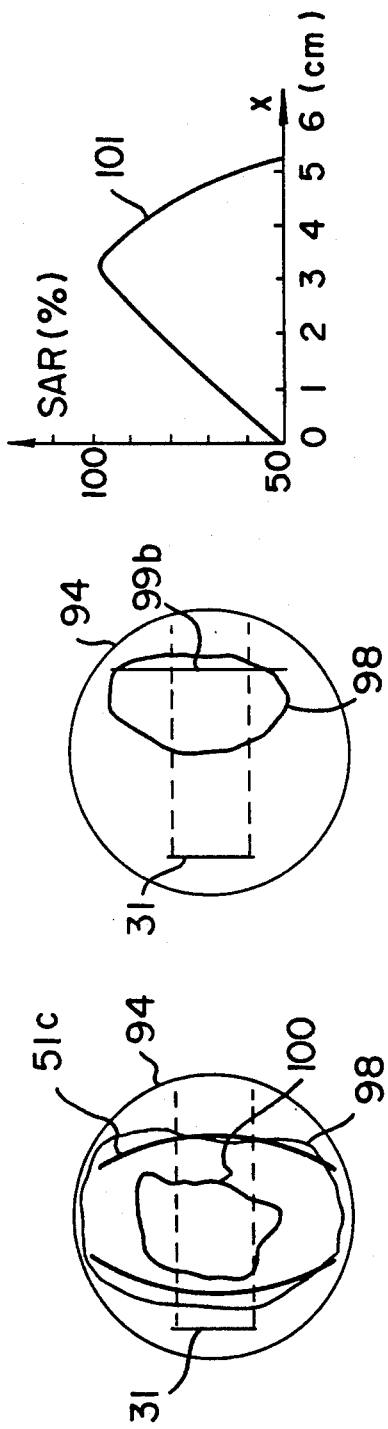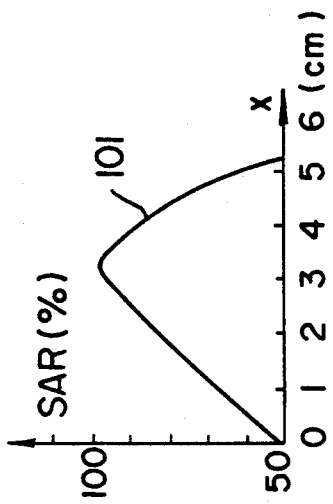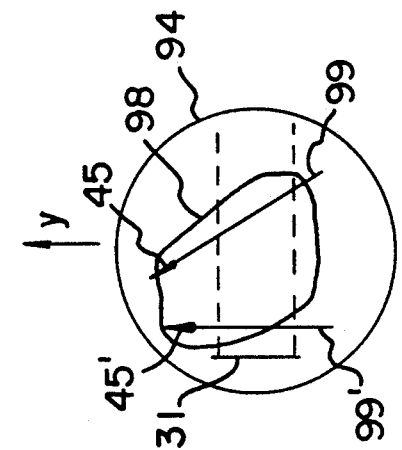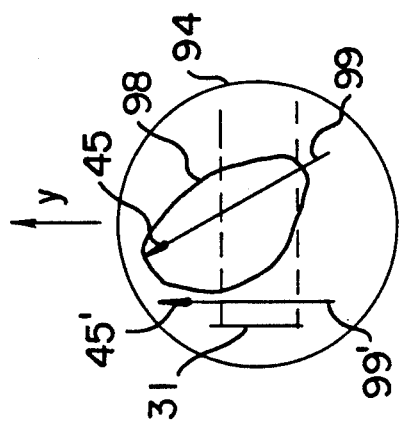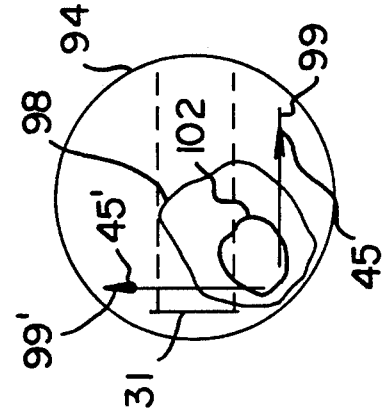

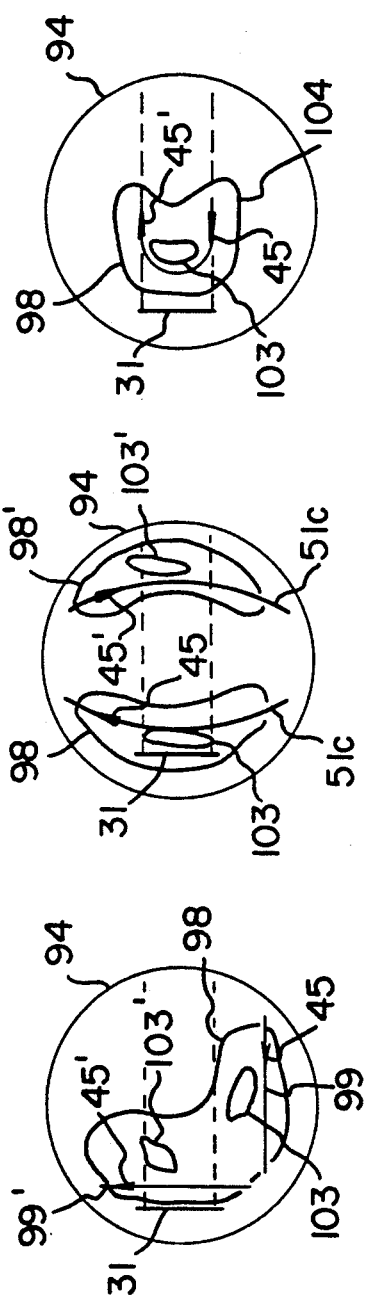
FIG.38D  FIG.38E  FIG.38F
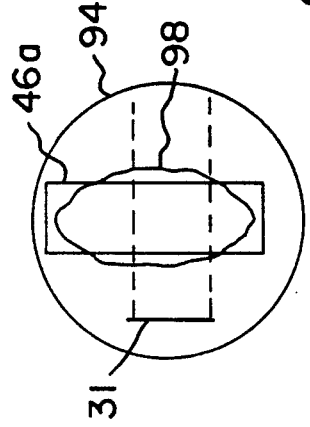
FIG.40
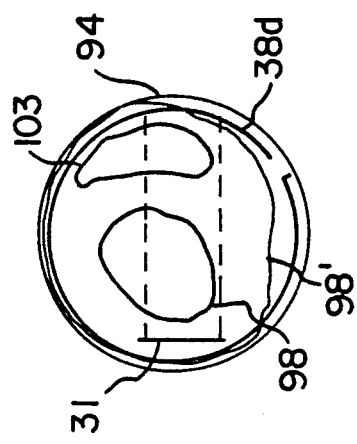
FIG.39
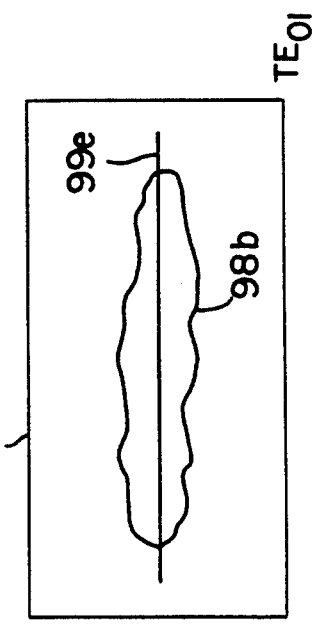
FIG.41B  TE$_{01}$
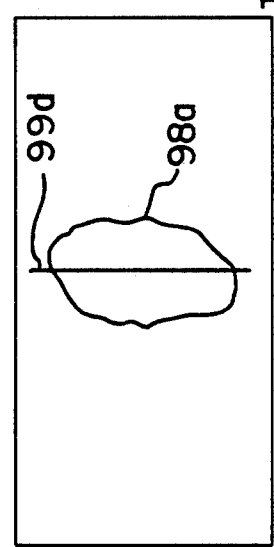
FIG.41A  TE$_{10}$

RADIO FREQUENCY THERMOTHERAPY

A. FIELD OF THE INVENTION

Heating of tumors is found to be effective in selectively killing the cells of cancerous tissues with respect to those of normal tissues.

B. BACKGROUND OF THE INVENTION

The therapeutic effects of heat also stimulate the immunological system. Destructive effects are further observed on the microvasculature of the tumor, which further enhances the heating of poorly vascularized tumor cores. When used in combined protocols with radiotherapy, synergistic effects arise due to a specific effect of heat on hypoxic cells, which enhances the killing effect of ionizing radiation. A further beneficial effect of heat in tumors is the enhancement of the effects of tumoricide drugs in combined treatments with chemotherapy (G. Hahn, Hyperthermia and Cancer, Plenum Press, N.Y.).

A further beneficial use of heat is found in palliative treatments of superficial musculature, subcutaneous tissues and/or joints, with heat usually administered as an adjunct to other therapeutical treatments (J. Lehmann, Therapeutic Heat and Cold, Williams and Wilkins, N.Y., 1982). Moreover, alleviation of prostatism occurs with heating the prostatic gland enlarged by benign prostatic hyperplasia. The beneficial effects of drugs is enhanced in a number of non-tumoral pathologies.

When the heating fields are generated by external applicators, it is often difficult to raise tissue temperatures of circumscribed target volume at depth to therapeutic levels without damaging the access tissues represented by the skin and subcutaneous fat layer. So far, the development of an inexpensive and versatile electromagnetic (EM) applicator to safely deliver localized heat to volumes of variable shape and size underneath the subcutaneous fat layer has presented an insolvable problem.

A hyperthermia EM applicator for subcutaneous and deeper tissues is characterized by the following main features. The penetration depth in a muscle tissue is defined as the depth at which the delivered EM energy, measured in Watt/kg in terms of specific absorption rate (SAR), is attenuated to 50% of the normalizing value measured at one cm depth in the same muscle tissue. The SAR space distribution is calculated in terms of the local $E(x,y,z)$ field and conductivity $(x,y,z)$ distributions as: $SAR = \alpha E^2/2$. Thus, for any applicator, an effective field size (EFS) defined by the 50 percent iso-SAR contour measured at one cm muscle depth, hereinafter referred to as either iso-SAR or EFS, may be used to assess the quality of the heating field of an applicator. The penetration depth for an efficient paracorporal applicator designed for subcutaneous heating should be about 2-3 cm within the muscle tissue in order to guarantee a uniform treatment of most muscle tissues. To this figure, the thickness of the access fat and bone layers have to be added, taking into account that in humans the fat layer varies from a few millimeters to a few centimeters. At the same time, the overheating of these access tissues should not be above an acceptable level.

An ideal applicator should not require a water bolus interposed between the applicator and the body surface. The bolus impedes the location and concentration of heat to a specific area and prevents an applicator from scanning a restricted area of the body surface. In addition, an EFS contour can be easily shaped by a moving applicator to the contours and sizes of the tissue to be exposed or to the anatomy of access site when the applicator is mobile rather than fixed.

Finally, an ideal applicator should exhibit low stray radiation levels and no electric hazards and should be patient customized and safely operated by unspecialized personnel in the clinical environment.

There are some intrinsic limitations in the design of EM applicators that should be considered. It is well known to the experts in electromagnetism that heating with EM sources occurs by two types of coupling between the body tissue and the EM radiator. In a dominant E-field type of coupling, in which E is the electric field component of the EM field, the radiator may be substantially described as a charge source. In a dominant H-field type of coupling, with H being the magnetic field component, the radiator may be substantially described as a current source. The latter coupling is referred to as inductive since the heating is due to the induced E-field and associated induced currents in the conductive and therefore lossy tissue. The main restraint in applicator design as required by the EM theory is that the heating E-field should be substantially directed parallel to the subcutaneous fat-muscle (bone-muscle) interface for minimizing the heating of the highly resistive fat (and bone) layer and improving the safety of the treatment.

Good applicator design requires the locally generated E-field to flow parallel to the body surface. This restraint rules out the use of E-field devices which use high power, direct-contact capacitive electrodes whose E-field lines impinge perpendicularly upon the fat-muscle interface. Such applicators produce unpredictable and delocalized heating field distributions and present treatment safety problems due to the overheating of fatty tissue, even if a cooling bolus is used. H-field coupled devices induce E-fields which comply with the above requirement, and are considered the safest and most practical devices. Such H-field applicators have the added advantage that they require neither direct contact with the body surface nor bolus cooling.

A further restraint is related to the frequency of the EM radiation. External heating with radiation of very short wavelength such as microwaves is minimally effective at depth because the absorption of energy in the access tissues along the heating field pathway is so great that insufficient energy reaches deep-seated tissues. Heating at depth with such short wavelengths entails overheating of the access tissues which would be subject to unsafe high intensity fields. It is well known to the experts in the art of therapeutic heating that the penetration depth of an EM radiator increases in direct proportion to the electric dimension of the radiator. This is a problem in the cases of localized heating of a small target volume for which small apertures have to be used. However, the smaller the aperture, the higher the frequency which lowers the penetration potential. This limitation on the use of higher frequencies comes from EM theory whereby the wavelength of the EM field supported by the modes of a resonant waveguide aperture radiator, hereinafter referred to as a resonant waveguide or resonant aperture radiator, is related to the transverse electric dimensions of the aperture. These in fact define the cutoff frequency of such waveguide, i.e., the lower limit for the working frequency in this modality of propagation. Aperture applicators working at frequencies as low as 27 MHz have been developed. However, in order that such a low frequency will still be above the cutoff frequency, waveguides must be dielectric-filled so that their transverse dimensions are brought down to sizes comparable with those of the tissue to be heated. A water loaded, very heavy and cumbersome waveguide applicator has been proposed (A. Paglione et al., Microwave J., Vol. 24, p. 71, 1981) which exhibits high penetration, but its aperture is far too large for the localized treatment of most subcutaneous tumors. Small size microstrip applicators working at 27 MHz have also been developed (R. H. Johnson et al., Strahlentherapie, Vol. 9, pp. 537-538, 1985) but the penetration is not improved with respect to microwave applicators of comparable aperture size and a thick bolus is required to prevent the strong EM near-fields from overheating access tissues. This results in a substantial reduction of the power density of the field impinging upon the body surface.

Thus, concentrating the heating field in a small cross section while maintaining high penetration are conflicting requirements which have limited the prior art development of resonant aperture applicators. In clinical practice, heating small target volumes by small aperture applicators working in the 200-600 MHz range is feasible with acceptable uniformity of heating for superficial tissues at depths not exceeding $-1.5$ cm, subcutaneous fat layer included. Within these limits, a full set of dielectric-loaded resonant aperture radiators of varying aperture size and penetration would have to be developed in order to meet wide clinical requirements. In any case, no in-field optimization of these applicators would be possible and precise treatment planning for small size subcutaneous target volumes at substantial depths could not be satisfactorily achieved given the high temperature gradients required for target tissue and the rapidly decaying heating fields with consequent low penetration.

Improvements in penetration and uniformity are obtained by the use of phased arrays in which a multi-element radiator is directed toward the target volume with a multiplicity of coherent electromagnetic heating fields which are controlled in phase, amplitude and orientation to give rise to a positive interference effect when out of phase and thus substantially enhancing the temperature elevation of tissue when in phase. This constitutes a method to focus the heating at a predetermined depth. The constructive interfering superposition of microwave or radio frequency radiation fields have long been employed in hyperthermia. Phased arrays of 4, 8 and even 16 resonant aperture applications are known. These, however, exhibit a complexity of operation and high manufacturing costs which are not rewarded by the small gain in uniformity and penetration obtained.

Fixed aperture applicators developed around undersized, air-filled, below-cutoff waveguides (BCW) have been proposed for hyperthermia therapy (J. Vrba et al., Tesla Electr., Vol. 2, pp. 44-50, 1984; J. Vrba, Czechoslovak Patent 227,270). In the design of these heating devices, the excitation of evanescent modes in the BCW for producing useful heating fields occurs accidentally and in uncontrolled ways and under no theoretical conditions would these devices produce heating fields as versatile and effective as the devices disclosed in the present invention.

Attempts to circumvent the intrinsic limitations of aperture radiators for deep subcutaneous treatments have been made by developing H-field and E-field heating devices working at low frequency and using the well-established technology of the inductive shortwave diathermy (J. Oleson, in IEEE Trans. Biomed. Engin., Vol. BME-31, pp. 91-97, 1984). H-field devices do possess the extremely important feature that in whichever direction the inducing currents flow with respect to the body surface, the locally induced E-field and associated currents will flow parallel to the body surface and to the subcutaneous fat-muscle interface, thus sparing the access fat layer from overheating.

Low frequency H-field devices exploit the quasi-static term of the EM field and appear to be of practical use because (1) they do not require a bolus and (2) are less expensive to manufacture and are of proven technology. These devices are substantially coils of various shapes derived from the flat, spiral or pancake multiturn coil design. They are widely used in shortwave diathermy and are placed externally with their coil plane parallel to the body surface. These coil applicators produce inside the body induced solenoidal E-fields and associated current loops which flow on planes substantially parallel to the plane of the inducing current loops, i.e., to the body surface.

The main limitation in the use of low frequency inductive devices is that the induced current loops exhibit a gradient towards their centroids, where the deposited SAR is vanishing, so that their SAR deposition pattern is non-uniform. Moreover, the penetration potential of multiturn coils is substantially impaired by the presence of large stray E-fields between coil turns, the field lines of which are impinging perpendicularly on the fat-muscle interface, causing subcutaneous fat overheating which limits the power that can safely be used and consequently the penetration depth. For both these limitations, multiturn coil devices are used only occasionally in tumor thermotherapy, where precise and uniform fields are required.

Improvements in penetration have been obtained in producing perpendicular E-field loops inside the body by the use of flexible magnetic flux-guides implemented with toroidal resonators at radio frequency, in which a high density magnetic flux is directed over the body surface by treatment ports suitably oriented (Proc. Hypert. Oncology 1988, T. Sugahara and M. Saito, eds., pp. 829-831, Taylor & Francis, 1989). A substantial part of this improvement is due to the low impedance exhibited by these flux guides, which are similar to a curved solenoid. In fact, the current lines are distributed over the whole toroidal wall and are flowing radially. However, this applicator appears to have a limited capability in determining the heating field size, shape and localization of the induced current loops.

A partial removal of the intra-turn E-fields of multiturn coils has been obtained in single rectangular loop applicators used with their loop plane perpendicular to the body surface, hereinafter referred to as magnetic dipoles or dipoles, which are inducing local E-fields also perpendicular to the body surface. The dipole heating field is characterized by a component due to the loopside proximal to the body surface to which the smaller but out-of-phase field of the distal loopside is superimposed. The negative effect of this out-of-phase field depends on the separation between loopsides, i.e., on the dipole height.

Planar dipoles have also been implemented by a large ribbon-like or sheet conductor working at 150 MHz, including a large metallic backplane. This dipole will be referred to as a distributed current dipole or distributed dipole (J. Bach Andersen et al., IEEE Trans. BME, Vol. 31, pp. 21-27, 1984).

Distributed dipoles at various frequencies have been described by others who have provided them with metal screening boxes which closely wrap the dipoles (R. H. Johnson et al., Electr. Letters, Vol. 22, pp. 591-593, 1986; R. H. Johnson et al., IEEE Trans. MTT, Vol. 35, pp. 1317-1321, 1987).

Distributed dipoles have been described with parallel slots in order to generate discrete parallel currents on proximal loopsides. They are provided with a flexible metallic backplane which allows the proximal loopsides to conform to cylindrical surfaces (R. H. Johnson et al., Proc. Hypert. Oncology 1988, T. Sugahara and M. Saito, eds., pp. 832-833, Taylor & Francis, 1989; A. W. Preece et al., Proc. 10th ESHO Symp., Amsterdam, p. 152, 1989).

Some improvements in SAR penetration and uniformity have been obtained with the use of lower frequency 27 MHz dipoles in a symmetric two side-to-side parallel dipole configuration (the Twin-Dipole). These lumped or distributed dipoles do exhibit some limitations in their use. They are low-efficiency devices due to both the spread of high intensity stray EM fields into open space in spite of the presence of the metallic backplane or box and to their short height, i.e., to a close distal loopside carrying the out-of-phase return current (IEEE Trans. Micr. Theory Techn., Vol. MTT-34, pp. 612-619, 1986).

The latter limitation has been removed by the implementation of a large (120 cm c.a.) ribbon-like conductive sheet applied against the body surface on which a high-intensity distributed current at 13.56 MHz is flowing, while the distal loopside is removed to a remote distance (80 cm c.a.) and does not contribute to the heating field. This device has been shown to be effective in penetration; however, its heating efficiency drops to the lowest level since the required radio frequency power of a few kilowatts is almost completely dispersed in the open space. Moreover, there is no practical way of controlling the local heating field distribution (H. Kato et al., J. Microw. Power, Vol. 18, pp. 331-336, 1983).

Improvements in heating penetration and uniformity with magnetic dipoles has been obtained with the development of a 27 MHz hybrid dipole applicator (Strahlentherapie, Vol. 9, p. 547, 1985). This operates by superimposing to the induced E-field of a twin-dipole device the unidirectional and coherent E-field generated by an auxiliary capacitive device. With this two different-element phased array applicator, the central SAR gradient typical of induced E-field loops disappears and a broad and deep SAR maximum appears by virtue of the positive interference of the two superimposed heating EM fields provided that the respective phase, amplitude and orientation are adjusted. Such an applicator can, however, be applied only to specific anatomic sites.

SUMMARY OF THE INVENTION

The present invention provides a method and an apparatus for the safe and precise therapeutic heating of tissues at substantial depths beneath the skin. This is accomplished by employing the EM composite heating fields generated by a hybrid passband applicator (HPA) from 0.1 MHz to 2450 MHz. The basic element of an HPA is a below cutoff waveguide (BCW) segment of any cross section size and shape which is supporting a plurality of evanescent modes. Three sets of resonant radiating elements are positioned inside the BCW at various distances from the aperture. The radiating elements of the first set are the most retracted from the BCW's aperture and are positioned within the BCW's pure exciting range to work as pure exciters and energize selected evanescent modes. The radiating elements of the second set are also retracted from the BCW's aperture to be instead positioned within the BCW's mixed exciting/radiating range to work both as exciters and direct radiators and energize further evanescent modes and emit a direct heating field, respectively. The radiating elements of the third set are working as direct radiators and are positioned by the BCW's aperture without substantially energizing any BCW's evanescent mode. The BCW's modes energized by both first and second sets of radiating elements produce a multi-modal heating field, which is propagating through the BCW's active aperture to the tissue to be exposed. The additional direct heating field generated by the second and third direct radiator sets contribute to the shaping of the resulting composite EM heating field of the HPA. The HPA aperture is positioned against the body surface encompassing the tissue under treatment from which it is separated by a gap. The heating method according to the invention includes the control of the many HPA parameters for optimizing the treatment of tissues of a large variety of sizes, shapes and depths for which a precise heat treatment is prescribed.

Further general objects of the invention are disclosed to provide hyperthermia methods and applicators for specific therapeutic applications.

It is an object of this invention to provide a method and an HPA apparatus for the hyperthermic treatment to the precise and uniform temperature elevations required for the hyperthermic treatment of deep subcutaneous tumors of any size and shape, including prostatic, bladder, mammary, uterus, ovaries, head and neck carcinomas and skin tumors including melanomas, osteosarcomas and lymph node tumors.

It is an object of the invention to provide a method and an HPA apparatus for the safe palliative hyperthermic treatment of deep subcutaneous tissues of any size and shape with a large variety of beneficial effects, including increasing the extensibility of collagen tissues, decreasing joint stiffness, producing pain relief, relieving musole spasms, assisting in resolution of inflammatory infiltrates, edema and exudates and increasing blood flow.

It is an object of the invention to provide a method and an HPA apparatus for the safe palliative hyperthermic treatment of the deep subcutaneous prostatic gland tissue of any size and shape to achieve beneficial effects in clinical cases of benign prostatic hyperplasia.

To achieve the foregoing and other objects according to the present invention as embodied and described therein, preferred HPA embodiments are disclosed, each of them falling within the scope of the present invention.

One object of the invention is to provide an HPA in which the radiating elements are distributed constant radiators, including monopoles, dipoles, helices or resonant apertures working in the high frequency range.

Another object of the invention is to provide an HPA in which the radiating elements are semi-distributed constant radiators including transmission line radiators working in the mid-range of the frequency.

Another object of the invention is to provide an HPA in which the radiating elements are lumped constant H-field coil radiators working in the low frequency range.

Another object of the invention is to provide an HPA in which the radiating elements are lumped constant H-field magnetic dipole radiators working in the low frequency range.

Another object of the invention is to provide an HPA in which the radiating elements are lumped constant H-field line current radiators working in the low frequency range.

One object of the invention is to provide tuning means in the lower frequency range for the EM coupling of an HPA to the power source frequency which is adjustable by automatic control means for taking care of the physiological changes of the tissue during the treatment. This is accomplished by manufacturing the resonant radiating elements with common tuning means implemented by a single variable capacitor to which the inductive parts of the radiating elements are connected in series, parallel or a series-parallel network.

Another object of the invention is to provide an HPA working in the low end of the frequency range and the lumped inductive parts of the resonant radiating elements are constructed with flexible conductive embodiments with the purpose of providing a simple operative means for infield adjustment of the radiator conformations and configurations to assist the cross-sectional heating pattern to match the target tissue size, shape, heterogeneity and depth.

Another object of the invention is to provide a versatile HPA delivering time-dependent heating fields the components of which are controlled along the treatment by manufacturing the resonant elements by flexible conducting embodiments and by providing mechanical means which are controlling the position, conformation or configuration of such flexible radiators to help accomplish the time and spatial profiles of the heating fields required for taking care of the physiological tissue changes occurring during the treatment.

Another object of the invention is to provide a versatile HPA delivering time-dependent heating fields the components of which are controlled along the treatment by feeding the resonant radiating elements by multi-channel power sources incorporating modulating means driven by time-dependent waveforms which are switching the individual radiator power among programmable intensity levels which will contribute to accomplish the required time and spatial profiles of the heating fields.

Another object of the invention is to provide matching means in the lower frequency range for the EM coupling of an HPA to the power source which is univocally adjustable for changes of tissue load during treatments also by automatic control means. This is accomplished by manufacturing exciters and direct radiators with inductive parts magnetically coupled among themselves and to the power source through a variable magnetic flux transformer which would provide a common matching means. This variable transformer is implemented by terminating the feeding cable from the EM source by a coupling loop which magnetically couples to the inductive portion of the radiating elements. The loop may be rotated or shifted coaxially to adjust its magnetic coupling to the inductive radiator parts, thus providing a precise and smooth matching to the power source.

Another object of the invention is to provide means for limiting the excitation of spurious evanescent modes or the emission of accidental direct heating fields by the radiating elements of the HPA. This is accomplished by hosting the cables feeding these radiating elements and their tuning and matching means in a shielded box outside the BCW.

Another object of the invention is to provide means for limiting the excitation of spurious evanescent modes or the emission of accidental direct heating fields by the radiating elements of the HPA. This is accomplished by hosting the cables feeding these radiating elements and their tuning and matching means beyond the exciting range of a prolonged BCW segment.

Another object of the invention is to provide an HPA which exhibits low stray E-fields. This is accomplished by connecting the inner BCW wall to one end of the radiating element conductive embodiments and to on electrode of the tuning capacitor.

Another object of the invention is to provide an HPA which exhibits low stray E-fields. This is accomplished by connecting the inner BCW wall to the electric midpoint of the radiating element inductive part or to the central electrode of the three-electrode tuning capacitor of electrically symmetric radiator embodiments.

Another object of the invention is to provide the BCW of HPAs with an electric short at its nonactive end.

Further objects of the invention are to provide HPAs according to the invention, the heating field of which is optimized to provide therapeutic temperature elevations in tissues to be exposed of specific size, shape, heterogeneity and depth.

Another object of the invention is to provide an HPA the heating field of which is optimized by selecting any number of resonant radiating elements in each of the three sets.

Another object of the invention is to provide an HPA in which the number of the resonant radiating elements of the second set is two.

Another object of the invention is to provide an HPA in which the number of the resonant radiating elements of the third set is two.

Another object of the invention is to provide an HPA in which the size of resonant radiating elements of the three sets is optimized to help provide the heating field to match the size, shape, heterogeneity and depth of the target tissues.

Another object of the invention is to provide an HPA in which the conformation of resonant radiating elements of the three sets is optimized to help provide the heating field to match the size, shape, heterogeneity and depth of the target tissues.

Another object of the invention is to provide an HPA in which the relative configuration of resonant radiating elements with respect to each other and to the BCW wall is optimized to help provide the heating field to match the size, shape, heterogeneity and depth of the target tissues.

Another object of the invention is to provide an HPA in which the relative position of resonant radiating elements with respect to the BCW aperture is adjusted to help provide the heating field to match the size, shape, heterogeneity and depth of the target tissues.

Another object of the invention is to provide an HPA which is optimized for the treatment of tissues of specific shape, size, heterogeneity and depth. This is accomplished by loading the BCW with low loss ferrite materials of selected size, shape and susceptibility with the purpose of substantially modifying the distribution of the H-field components of the heating fields.

Another object of the invention is to provide a versatile HPA delivering time-dependent heating fields which are controlled during the treatment by providing mechanical means which are controlling the position of the ferrite load of the BCW to help accomplish the required time and spatial profiles of the heating fields.

Another object of the invention is to provide an HPA which is optimized for the treatment of tissues of specific shape, size, heterogeneity and depth. This is accomplished by loading the BCW with low loss dielectric materials of selected size, shape and permittivity with the purpose of substantially modifying the distribution of the E-field components of the heating fields.

Another object of the invention is to provide a versatile HPA delivering time-dependent heating fields which are controlled during the treatment by providing mechanical means which are controlling the position of the dielectric load of the BCW to help accomplish the required time and spatial profiles of the heating fields.

Another object of the invention is to provide an HPA which is optimized for the treatment of tissue to be exposed by employing BCW with circular cross-sectional apertures or by employing BCW with rectangular cross-sectional apertures with any side ratio.

Another object of the invention is to provide an HPA which is optimized for the treatment of tissues exhibiting a specific size, shape, heterogeneity and depth. This is accomplished by adjusting the size, shape or curvature of the BCW aperture, including the insertion of transition cross-sectional waveguide segments.

Another object of the invention is to provide a versatile HPA delivering time-dependent heating fields the components of which are controlled along the treatment by manufacturing the HPA aperture of variable size, shape or curvature and by providing means which are controlling the aperture size, shape or curvature to help accomplish the required time and spatial profiles of the heating fields.

Another object of the invention is to provide an HPA which is optimized for the treatment of tissues of specific size, shape, heterogeneity and depth. This is accomplished by constructing said resonant radiating elements of the first and second set working as exciters with a suitable symmetry and configuration compatible for preferentially exciting the fundamental modes of the BCW.

Another object of the invention is to provide an HPA which is optimized for the treatment of tissues of specific size, shape, heterogeneity or depth. This is accomplished by modifying the multi-modal field of the HPA by inserting mode filters of specific symmetry inside the BCW for suppressing specific modal components.

Additional objects of the invention are to provide further HPAs which are optimized for providing therapeutic temperature elevations in tissues to be exposed of specific size, shape, heterogeneity and depth.

An additional object of the invention is to provide an HPA employing resonant radiating elements fed by power sources at more than one frequency to provide heating fields with components of variable penetration.

An additional object of the invention is to provide an HPA provided with means for controlling the power level of each resonant radiating element including a multi-channeled feeding device with individual power level and phase shift control means in every channel to provide heating fields of adjustable component intensity and phase.

An additional object of the invention is to provide an HPA which is optimized for the treatment of tissues localized in anatomic sites presenting curved body surfaces. This is accomplished by shaping the BCW aperture to substantially conform to the curved body surface to provide a more uniform penetration.

An additional object of the invention is to provide an HPA the active aperture of which is occluded by a conformal radiation shield in which one or more treatment ports have been cut away and the size, conformation and configuration of the ports are adjusted to help provide secondary heating fields to match the tissues to the exposed size and shape.

Another object of the invention is to provide a versatile HPA delivering time-dependent heating fields which are controlled during the treatment by providing mechanical means which are controlling the shape, size or configuration of the treatment ports cut through a radiation shield occluding the BCW aperture to help accomplish the required time and spatial profiles of the heating fields.

An additional object of the invention is to provide an endocavitary HPA which is optimized for the treatment of tissues localized on the inner wall of body cavities. This is accomplished by providing an HPA in which one or more supplementary treatment ports have been cut sideways on the BCW wall and the size, conformation and configuration of these ports are adjusted to help match the heating fields to the tissue to be exposed and localized on the body cavity wall.

An additional object of the invention is to provide an HPA the EM coupling of which with the body is optimized by adjusting the length of the air gap.

An additional object of the invention is to provide an HPA the EM coupling of which with the body is optimized by interposing in the gap a matching bolus of adjustable EM properties and thickness.

An additional object of the invention is to provide an HPA which is optimized for the treatment of tissues to be exposed at substantial depths while keeping the overall BCW size to a minimum. This is accomplished by selecting a working evanescent mode for the BCW by a suitable choice of exciters and by enlarging only the relevant electric dimension of the BCW aperture for the passband mode of propagation of the working mode selected.

Another object of the invention is to provide an HPA which is optimized for the treatment of tissues localized at depth in body segments of near-cylindrical symmetry. This is accomplished by employing a single HPA equipped with a single toroidal shaped BCW surrounding the body segment to be treated and whose heating field cylindrical wave from the circumferential aperture extending all around the inner wall of the BCW is impinging radially on the near-cylindrical body surface.

Further objects of the invention provide hyperthermia methods and systems according to the invention which are generating heating fields for safely providing a circumscribed and enhanced temperature rise in tissues to be exposed of any size, shape, tissue heterogeneity and depth and/or located in anatomic sites for which the field of a single hyperthermia applicator is inadequate.

A further object of the invention is to provide a method and a system for the safe and focused heating of a tissue mass. This is accomplished by a like element phased array of HPAs, the heating field of which is individually controlled in intensity and phase and in orientation with means well known to people skilled in the art so that their heating fields are preferably superimposed over the tissue to be exposed where they are positively interfering and providing enhanced heating focused on the target tissue.

A further object of the invention is to provide a method and system for the safe and circumscribed heating of tissue masses at substantial depths. This is accomplished by a hybrid element phased array whereby to the principal heating field of an HPA are superimposed the phase coherent EM heating fields generated by active auxiliary devices energized by independent power sources giving rise to a substantially constructive interference effect preferentially over the target volume which results in a circumscribed target temperature enhancement. At low RF frequencies, the auxiliary devices include capacitive electrodes, inductive coils and hybrid combinations of these.

A further object of the invention is to provide a method and apparatus for the safe and circumscribed heating of tissue masses at substantial depths. This is accomplished by a hybrid element phased array whereby to the principal heating field of an HPA are superimposed the phase coherent EM heating fields generated by passive auxiliary devices energized by an adjustable EM coupling with said HPA and giving rise to a substantially constructive interference effect preferentially over the target volume which results in a circumscribed target temperature enhancement. At low RF frequencies, the auxiliary devices include capacitive electrodes, inductive coils and hybrid combinations of these.

A further object of the invention is to provide a method and system for providing uniform temperature elevations on tissue masses located at depth in the subcutaneous area. This is accomplished by providing mechanical means which are programmed for cyclically scanning the HPA following specific pathways and speeds and duty cycles over that portion of skin which is used to access the heating target. The heating fields are continuously aimed at the tissue target to produce a circumscribed and enhanced heating.

It is a further general object of the invention to provide a method and apparatus for the safe and precise therapeutic heating of tissues at substantial depths beneath skin by the EM composite heating field generated by an HPA in which only the first set of resonant radiating elements working as pure exciters and positioned within the BCW's pure exciting range and the third set of pure direct radiators positioned in the pure radiating range are integrated in the BCW to produce a controlled passband applicator (CPA).

It is a further general object of the invention to provide a method and apparatus for the safe and precise therapeutic heating of tissues at substantial depths beneath the skin by the EM composite heating field generated by an HPA in which only a first set of resonant radiating elements working as pure exciters and positioned with the BCW's pure exciting range and the second set of exciters/radiators positioned in the mixed exciting/radiating range are integrated in the BCW to produce a semi-controlled passband applicator (SCPA).

It is a further general object of the invention to provide a method and apparatus for the safe and precise therapeutic heating of tissues at substantial depths beneath the skin by the EM composite heating field generated by an HPA in which only the second set of resonant radiating elements working as exciters/radiators and positioned within the BCW's mixed exciting/radiating range and the third set of pure radiators positioned in the pure radiating range are integrated in the BCW to produce a partially controlled passband applicator (PCPA).

It is a further general object of the invention to provide a method and apparatus for the safe and precise therapeutic heating of tissues at substantial depths beneath the skin by the EM composite heating field generated by an HPA in which only the second set of resonant radiating elements working as exciters/radiators and positioned within the BCW's mixed exciting/radiating range are integrated in the BCW to produce a mixed passband applicator (MPA).

It is a further general object of the invention to provide a method and apparatus for the safe and precise therapeutic heating of tissues at substantial depths beneath the skin by the EM pure multi-modal heating field generated by an HPA in which only the first set of resonant radiating elements working as pure exciters and positioned within the BCW's pure exciting range are integrated in the BCW to produce a pure passband applicator (PPA).

It is a further general object of the invention to provide a method and apparatus for the safe and precise therapeutic heating of tissues at substantial depths beneath the skin by the heating field generated by an HPA in which only the third set of direct radiators positioned within the BCW's direct radiating range is producing a radiator-in-BCW applicator (RA).

The foregoing and other objects and advantages of the present will appear from the following description which is referred to in the accompanying drawings in which preferred embodiments of the invention are illustrated. It should be understood that various modifications and combinations of the illustrated embodiments will be apparent to those skilled in the art within the scope of the invention and that the cited examples of particular embodiments have been given by way of illustration and are not intended as limitations on the scope of the invention, which is susceptible of apparently widely different embodiments without departing from the scope thereof.

Accordingly, this invention should not be limited by the embodiments described herein and reference is made therefore to the claims herein for interpreting the scope of the invention.

BRIEF DESCRIPTION OF THE DRAWINGS

These and other objects, features and advantages of the present invention will become apparent to those skilled in the art of electromagnetic hyperthermia from the following specifications which should be considered in conjunction with the accompanying drawings in which like reference numerals refer to like parts wherein:

FIG. 1 shows a schematic side view with parts cut away of HPA hyperthermia applicator embodiments coupled to the tissue to be exposed by an air gap, showing the passband waveguide segment, the mode-exciting radiators and the direct radiators positioned within their respective working ranges;

FIG. 1(g) shows a schematic side view with parts cut away of an HPA hyperthermic applicator embodiment;

FIG. 2(a) is a schematic side view with parts cut away of a waveguide segment working in the propagation mode of the prior art, showing the $E_{xy}$- and $E_z$-field patterns of the transversal electric $TE_{11}$ propagation mode;

FIG. 2(b) is a circular cross section of FIG. 2(a);

FIG. 3(a) is a schematic view with parts cut away of a passband waveguide segment of circular cross-section according to the invention which is heating a body tissue coupled to the waveguide aperture and including the $E_z$-field pattern of the $TE_{11}$ evanescent mode excited by a power source;

FIG. 3(b) is a schematic view of the embodiment of FIG. 3(a);

FIG. 4 is a front view of the aperture of a waveguide of circular cross section showing the theoretical density power map of the fundamental $TE_{11}$ mode;

FIGS. 5(a)-(m) are schematic front views of alternative embodiments of low $TE_{mn}$ modes of waveguides of various cross section shapes of hyperthermia applicators;

FIG. 7 is a front view of the rectangular aperture of the passband waveguide of an applicator showing a resonant radiator embodiment positioned for exciting the $TE_{10}$ evanescent mode;

FIGS. 8(a) and (b) are front views of alternative embodiments of passband waveguide rectangular apertures of applicators according to the invention excited to higher modes by transverse loop exciter embodiments and a modal filter embodiment suppressing an unwanted transversal mode;

FIGS. 9(a) and (b) are front views of alternative embodiments of a passband waveguide rectangular aperture of applicators excited by resonant dual-exciter embodiments positioned for simultaneously exciting two orthogonal evanescent modes of propagation;

FIGS. 20(a)-(f) show schematic side views with parts cut away and front views of embodiments of hyperthermia applicators provided with radiation shields and associated treatment ports and an extended aperture applicator embodiment for improved penetration;

FIG. 21 shows a schematic side view with parts cut away of an embodiment of a hyperthermia applicator provided with electronically scanned radiators;

FIGS. 22(a) and (b) show schematic side views with parts cut away of alternative embodiments of hyperthermia applicators provided with concave apertures and director radiators shaped to conform to cylindrical body segment surfaces;

FIG. 23 shows a schematic side view with parts cut away of an embodiment of a hyperthermia applicator provided with a convex aperture and direct radiators shaped to conform to a cylindrical body surface concavity;

FIG. 24 shows a schematic side view with parts cut away of an alternative embodiment of a hyperthermia applicator provided with a convex radiation shield shaped to conform to a cylindrical body concavity;

FIG. 25 shows a schematic side view with parts cut away of an embodiment of an endocavitary hyperthermia applicator provided with a side aperture for the treatment of body cavity sidewall tissues;

FIG. 26 shows a schematic side view with parts cut away of an embodiment of a hyperthermia applicator provided with circumferential aperture and discrete direct radiators for the treatment of deep-seated tissues inside pseudo-cylindrical body segments;

FIGS. 29(a)-(d) show schematic side views with parts cut away of an embodiment of a hyperthermia applicator provided with a capacitive auxiliary heating device for improving the penetration in the treatment of deep-seated tumors;

FIGS. 35(a)-(d) show a schematic front view with parts cut away of transverse iso-SAR contours of a cylindrical cross section applicator provided of direct radiators giving heating fields of different sizes;

FIG. 36 shows a schematic front view with parts cut away of a transverse iso-SAR contour of a cylindrical cross section applicator showing the edge effect of a direct heating field radiator;

FIG. 37 shows an asymmetric SAR profile along the x-axis of a cylindrical cross section applicator showing the edge effect of a direct field radiator;

FIGS. 38(a)-(f) show a schematic front view with parts cut away of transverse iso-SAR contours of a cylindrical cross section applicator showing the effects of the conformation, configuration and phase of radiator currents;

FIG. 39 shows a schematic front view with parts cut away of transverse iso-SAR contours of a cylindrical cross section applicator provided with a planar loop coil direct radiator;

FIG. 40 shows a schematic front view with parts cut away of a transverse iso-SAR contour of a cylindrical cross section applicator provided with a current sheet direct radiator; and FIG. 41(a)-(b) show schematic front views with parts cut away of transverse iso-SAR contours of a rectangular cross section applicator provided with single-line direct radiators.

DESCRIPTION OF PREFERRED EMBODIMENTS

Figure 1A:
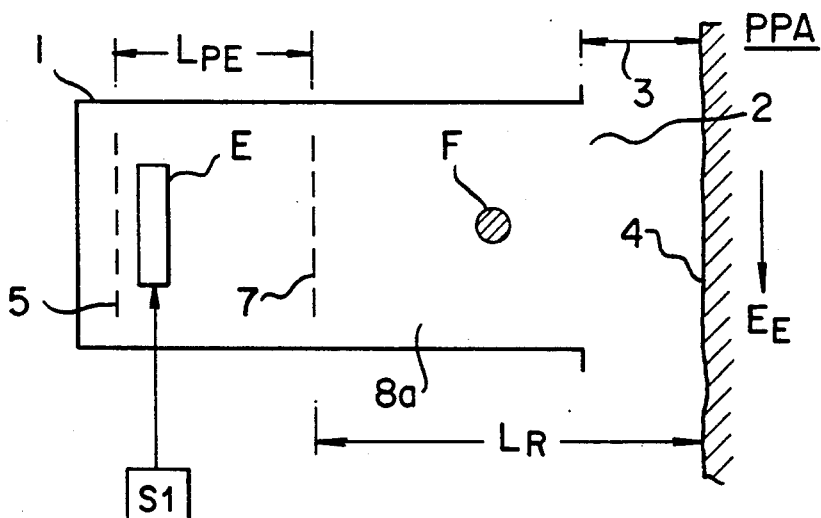
FIG. 1(a) shows a schematic side view with parts cut away of a PPA hyperthermic applicator embodiment.

This invention discloses simple to operate, safe, low cost and very versatile hyperthermia applicators and systems for the delivery of EM energy from about 0.1 Megahertz (MHz) to 2.450 Gigahertz (GHz) for optimized hyperthermia treatments of subcutaneous tissues of any size, conformation and depth, together with heating modalities and optimization means. The preferred embodiment and best mode of the invention is shown in FIG. 1(g). In the FIGS. 1(a)-(f), partially implemented applicator configurations are shown.

All applicator embodiments are based on the working principle of the EM waveguides working below their cutoff frequency, which is illustrated with the help of FIG. 1(a).

The waveguide segment 1, terminated by a short at one end, presents the active treatment aperture 2 at the other end, which is separated by a gap 3 from the body tissue to be exposed 4. It is assumed that waveguide segment 1 has cutoff frequency fc for the dominant mode and works with waves of frequency $f < f_c$. Such a waveguide is referred to as a below-cutoff waveguide (BCW). A first set of EM resonant radiating elements represented as E, hereinafter referred to as the pure exciter set, is placed inside waveguide segment 1 in the BCW pure exciting range $L_{PE}(5,7)$ defined by the positions 5 and 7 from the BCW aperture, which are depending on the BCW cross-sectional parameters. Under this condition, E excites some evanescent modes of waveguide segment 1 when fed by EM energy from source $S_1$ of frequency $f_e < f_c$. The resulting multi-modal EM field $E_E$ at the frequency $f_e$ generated by the excited evanescent modes of waveguide segment 1 flows across aperture 2 and impinges upon tissue 4 through gap 3, delivering therapeutic heat. As long as E falls within positions 5 and 7 of FIG. 1(a), its direct heating field is not reaching body tissue to be exposed 4 with a significant energy level since E is not within the radiating range $L_R$ (7,4) of waveguide segment 1. Applicator 8a of FIG. 1(a) will hereinafter be referred to as pure passband applicator (PPA). The PPA offers the advantages of simple operation, low manufacturing costs and a shaping of the heating field by selecting a multiplicity of BCW modes through a proper selection of the exciter symmetry and BCW cross section shape and free from the interference of spurious direct radiation fields generated by the radiating elements. A further selection of mode-specific components of the multi-modal field is accomplished with the help of mode suppressing filters F and by other optimization means, helping to match the PPA heating field to the tissue to be exposed size, shape, heterogeneity and depth.

Figure 1B:
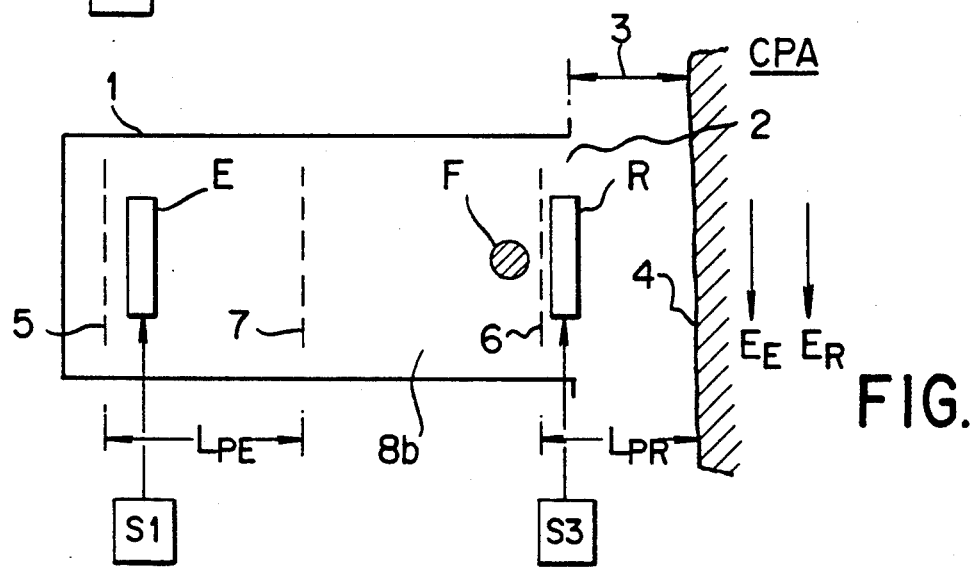
FIG. 1(b) shows a schematic side view with parts cut away of a CPA hyperthermic applicator embodiment.

Another embodiment integrates in a pure passband applicator, an independently controlled set of resonant radiating elements working as direct radiators. The combination of these two independently controlled radiator sets into a dual-stage hybrid applicator allows a composite heating field exhibiting a number of original and useful features which cannot be obtained with single radiator set devices. This embodiment is illustrated in FIG. 1(b). Here, BCW 1 is hosting the pure exciter set E fed by power source S1 of frequency $f_e (< f_c)$ and working within the $L_{PE}$ range. The heating field $E_E$ generated by E flows across aperture 2 and impinges upon tissue 4, delivering the multi-modal portion of the therapeutic heat. The resonant radiating elements of the further radiator set R are substantially working as pure direct radiators within the pure direct radiating range $L_{PR}(6,4)$, i.e., beyond the extreme position 6 of the whole exciting range $L_E$ of waveguide segment 1. R is fed by power source $S_3$ of frequency $f_r$ ($<f_c$) and is directly radiating the heating field $E_R$ which impinges upon tissue 4 and releases locally the directly radiated portion of the thereapeutic heat. The local $E_R$ field in tissue 4 would decrease in intensity as R is withdrawn inside waveguide segment 1, but keeps a significant intensity as long as R gets to position 7, which defines the R pure radiating range LR extreme. However, in this embodiment, R is kept within the pure $L_{PR}(6,4)$ range, in order to avoid the excitation of further BCW evanescent modes. The therapeutic heat is delivered to tissue 4 by the composite heating EM field obtained by the local superimposition of the pure $E_E$ and $E_R$ fields. This composite field may be optimized for the treatment of any tissue size, shape, heterogeneity and depth by suitable means independently controlling the size, shape, penetration and relative intensity of each field component. Any intermixing of field components due to accidental coupling of R with the BCW aperture may be quenched by proper mode filters F placed beyond position 6 for suppressing unwanted modes. Applicator 8b is the controlled passband applicator (CPA). The CPA presents some versatility in producing composite heating fields to match precise clinical requirements with rather simple means.

Figure 1C:
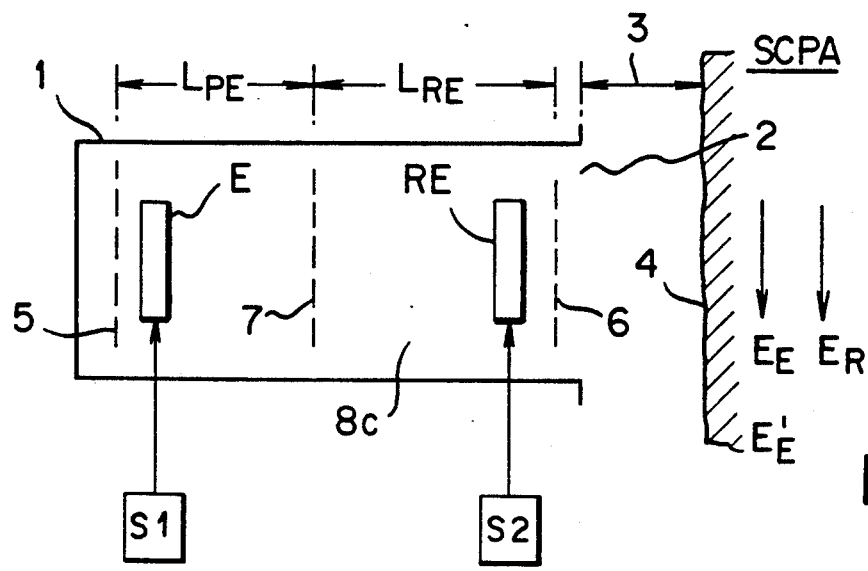
FIG. 1(c) shows a schematic side view with parts cut away of an SCPA hyperthermic applicator embodiment.

Another simple preferred applicator embodiment according to the invention is applicator 8c of FIG. 1(c), in which the first set of pure exciters E is positioned within $L_{PE}(5,7)$ and generates the multi-modal field $E_E$, while a second set RE of exciters/direct-radiators is positioned within the mixed exciting/radiating range $L_{RE}(7,6)$, generating a further multi-modal field $E_E'$ plus the direct field $E_R$. The composite $E_E+E_E'+E_R$ field flows across aperture 2 and impinges upon body tissue 4, delivering the therapeutic heat. Embodiment 8c is referred to as the semi-controlled passband applicator (SCPA).

Figure 1D:
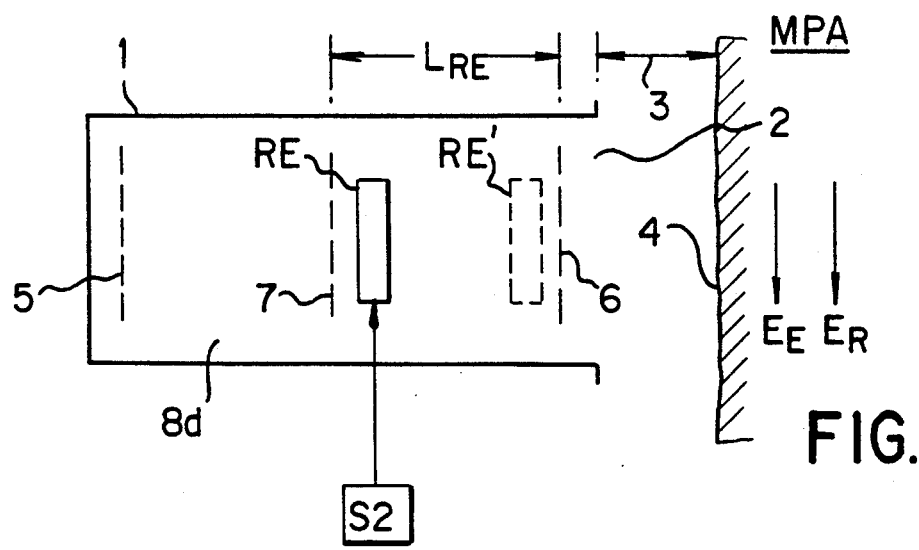
FIG. 1(d) shows a schematic side view with parts cut away of an MPA hyperthermic applicator embodiment.

The applicator embodiment 8d of FIG. 1(d) is characterized by having only one set of resonant radiating elements RE positioned within the mixed exciting-radiating range $L_{RE}(7,6)$ of waveguide segment 1. Thus, RE works as exciter with BCW 1 with the resulting multi-modal field $E_E$ flowing across aperture 2 and impinging upon body tissue 4. RE simultaneously delivers the local direct heating filed $E_R$, which decreases in intensity as RE is withdrawn inside waveguide segment 1 and substantially vanishes when the extreme position 7 of $L_{RE}$ is reached. Applicator 8d is very simple to operate and manufacture, yet provides a safe and useful composite heating field by the local superimposition of $E_E$ and $E_R$ fields in body tissue 4. The versatility of applicator 8d is increased if a part RE' of the exciter/radiator set is positioned closer to the terminal position 6 of $L_{RE}$ to provide an increased contribution to the direct heating field. In this and other ways, the composite heating field can be easily and effectively optimized for the treatment of many tissue sizes, shapes and depths with very simple means. These include a control of the power level ratio between direct and modal field components accomplished by shifting the position of the RE elements along $L_{RE}$. Applicator 8d is referred to as the mixed passband applicator (MPA).

Figure 1E:
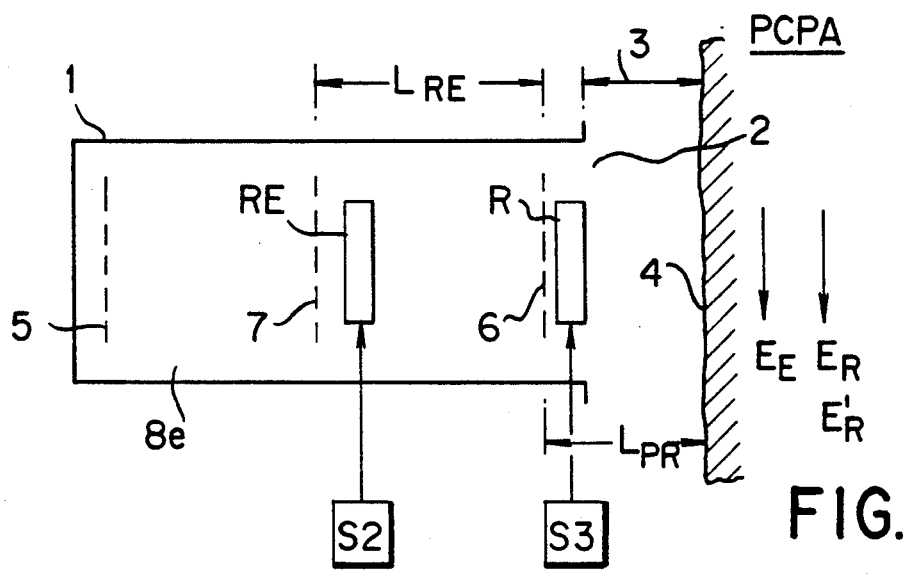
FIG. 1(e) shows a schematic side view with parts cut away of a PCPA hyperthermic applicator embodiment.

In applicator embodiment 8e of FIG. 1(e), one set of mixed exciters/radiators RE is positioned within $L_{RE}(7,6)$ and a further set R of pure direct radiators is positioned within $L_{PR}(6,4)$. Thus, the direct fields $E_R$ and $E_R'$ generated by R and RE, respectively, flow across aperture 2 and impinge upon 4, delivering the direct field portion of the therapeutic heat, while the local field $E_E$ generated by RE is delivering the multi-modal field portion. Applicator 8e is substantially as complex to operate as applicator 8b of which keeps most of the versatility and is useful when a stronger multi-modal field is required. Applicator 8e is referred to as the partially controlled passband applicator (PCPA).

Figure 1F:
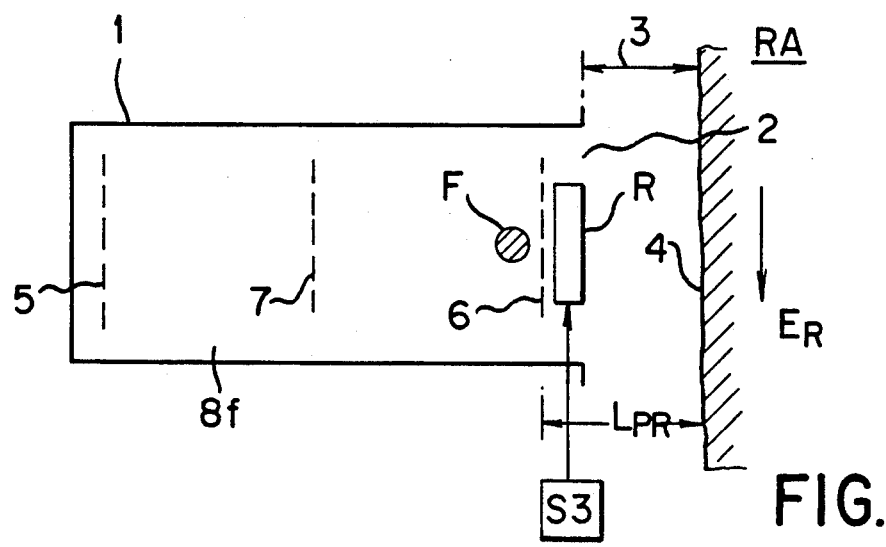
FIG. 1(f) shows a schematic side view with parts cut away of an RA hyperthermic applicator embodiment.
Figure 5E:
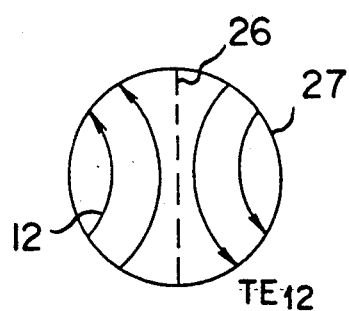
Figure 5F:
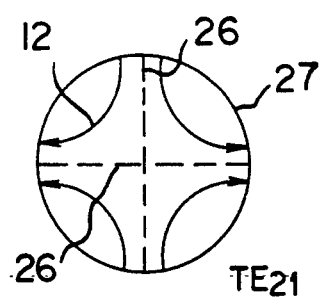
Figure 5G:
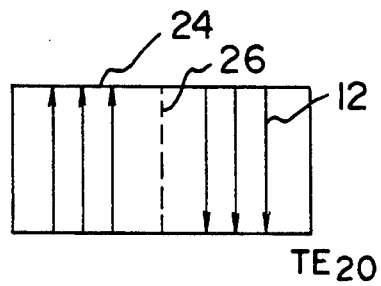
Figure 5H:
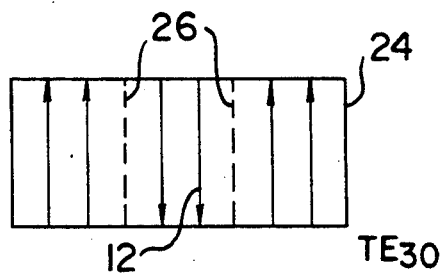
Figure 5I:
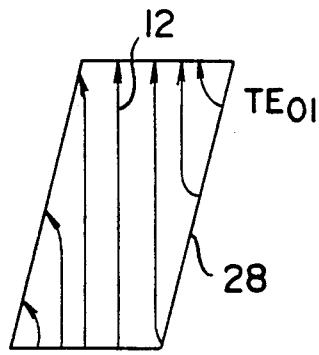
Figure 5L:
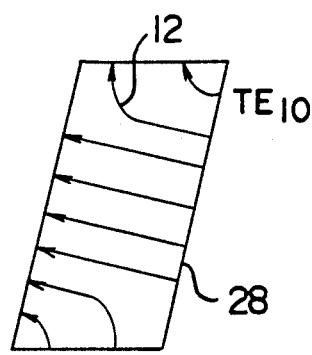
Figure 5M:
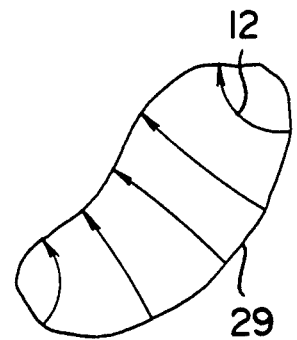

Another applicator embodiment is 8f of FIG. 1(f), which integrates in waveguide segment 1 the only set R of pure direct-radiators within the $L_{PR}(6,4)$ range, the heating field ER of which impinges upon body tissue 4 and releases the therapeutic heat. The multi-modal filter F is suppressing any significant modal fields likely to be accidentally excited by R. The position of the aperture 2 surrounding R affects the radiation field of R in ways useful in hyperthermic treatments, in that aperture 2 represents a substantial EM boundary with an excellent shielding feature and without generating strong near fields impairing the penetration potential as instead occurring with the close shielding boxes of prior art devices (see: R. H. Johnson et al., loc. cit.). Applicator 8f is the simplest to operate and exhibits the lowest manufacturing costs, yet provides a safe and useful $E_R$ heating field in body tissue 4, and keeps adequate versatility and is easily optimized with simple means to cope with a large variety of tissues to be exposed. We shall hereinafter refer to applicator 8f as the radiator-in-BCW applicator (RA).

A more general applicator embodiment according to the invention is illustrated as applicator 8 in FIG. 1(g). From this complex embodiment, the simpler and partial embodiments described as 8a–f in FIGS. 1(a–f) were derived. In the embodiment 8 of FIG. 1(g), the first set of pure exciters E is positioned within $L_{PE}(5,7)$ of BCW 1 and generates the multi-modal field $E_E$, while the second set RE of exciters/direct-radiators is positioned within the mixed exciting/radiating range $L_{RE}(7,6)$, generating a further multi-modal field $E_E'$ plus the direct field $E_R$. The third set of direct radiators R is positioned within $L_{PR}(6,4)$ and generates the direct field $E_R'$. The composite $E_E+E_E'+E_R+E_R'$ field flows across aperture 2 and impinges upon body tissue 4, delivering the therapeutic heat. We shall hereinafter refer to embodiment 8 as the hyrid passband applicator (HPA). This embodiment is most versatile, and its optimization for generating specific composite heating field results very precise and effective on account of the higher number of optimization parameters involved.

Since the basic working principle of the present invention is the integration of a plurality of sets of direct radiators into a BCW, the CPA, PCPA, SCPA, MPA, PPA and RA devices as well as any further embodiments in which any radiating means are inserted and positioned anywhere into any BCW are generically referred to as hybrid passband applicators (HPA) in any presentation of features which apply to them.

The applicators of the prior art which are based on the use of a BCW and which are supposed to generate a pure modal field (see: J. Vrba et al., loc. cit.) are effectively producing a heating field which can be shown to be a directly emitted EM field which is accidentally shaped as the BCW modal field. This field is not adequately characterized theoretically and the relative prior art assumptions are misleading. The prior art assumptions are:

(1) in order to excite the BCW evanescent modes, the radiating elements have to be placed as close to the BCW aperture as possible;

(2) the heating field produced by a BCW excited by such radiators in such an aperture position is a pure multi-modal field;

(3) the only allowed conformation and configuration of these aperture resonant elements are those congruent to the symmetry of the BCW modes to be excited, which would give rise to fixed iso-SAR contours.

From the thorough analysis on the behavior of the hybrid BCW devices and from the results which are disclosed in the present invention, the following conclusions can be drawn:

(1a) pure modal fields are generated only by heating elements within the pure exciting $L_{PE}$ range, which is quite far from the BCW aperture;

(2a) what is claimed to be a pure BCW multi-modal field by the prior art appears instead the substantially pure direct heating field of the radiating elements;

(3a) the prior art devices do not possess any comparable degree of optimization of their heating fields.

Therefore, no knowledgeable design of prior art BCW applicators can produce heating devices possessing the relevant features for being representative of the following classes, as disclosed in the present invention: (i) pure evanescent-mode applicators (PPA); (ii) mixed, evanescent-mode/directly-radiating applicators (MPA); (iii) purely radiating elements in-a-BCW aperture (RA) (or of their combinations: CPA,SCPA,PPA, and HPA).

The working principle for the BCW heating devices may be summarized as follows. Waveguides working below the cutoff frequency of their dominant mode, i.e., BCWs, appear to be the only examples of distributed constant networks which do not propagate progressive waves. However, it is known (G. Craven, Microwave J., Vol. 13, pp. 51-58, 1970) that they may be used in a variety of propagation devices, such as filters, etc., with the insertion of lumped or semi-lumped resonant circuits. Thus, BCWs suitably loaded by resonators become passband devices centered about the resonance frequency of these circuits with the concomitant excitation of the BCW evanescent modes.

The evanescent mode energy delivery to an external load is compared with the normal mode of waveguide propagation at $f > f_c$ with the help of FIGS. 2 and 3. Experts in electromagnetism know that when a waveguide is over-dimensioned, i.e., when the frequency f of the EM wave is above the cutoff frequency $f_c'$ calculated for the dominant mode through the waveguide cross section dimensions, i.e., $f > f_c$, the wave freely propagates along the waveguide in the commonly used devices for waveguide energy transmission. In FIG. 2(a), the circular cross section waveguide segment 9, working at $f > f_c$, is shown with half a section cut away. The E-field, represented by the vectors 10, is propagating within the conductive walls of waveguide 9 with a longitudinal space periodicity characterized by the succession of the E-field nodal (E=0) planes 11, which determine the guide wavelength ($\lambda_g$). In FIG. 2(b), a front view of the circular cross section of waveguide 9 is schematically illustrated together with the E-field line distribution 12 for the fundamental transversal electric $TE_{11}$ mode for a cylindrical cross section.

In FIG. 3(a), the circular cross-section BCW segment 13 is shown with half a section cut away. BCW 13 does not support any longitudinal resonant mode of propagation and therefore does not exhibit a longitudinal periodicity of the E-field distribution. However, BCW 13 supports exactly the same transversal electric $TE_{mn}$ and transveral magnetic $T_{mn}$ modes of resonant waveguides of the same cross section shape, which are now $TE_{mn}$ and $TM_{mn}$ evanescent modes. In any case, any below cutoff working frequency $f (< f_c)$ needs not be related to the transversal dimensions of the BCW for exciting its evanescent modes. Inside BCW 13, an EM field generated by any radiating means at any given point is reactively attenuated along the waveguide with a linear attenuation constant given by:

$$\alpha = 0.020944 (f_c^2 - f^2)^{\frac{1}{2}} \qquad [1]$$

In equation [1], $\alpha$ is in dB/m for any cross section and may be calculated for any mode of cutoff frequency $f_c$. The frequencies are in MHz. However, this type of attenuation is without an effective loss of energy in that the EM energy which it is not made available at a further point along the BCW is reflected back to the power source. If a resonant exciter is placed at the position 14, the intensity of the E-field of the excited modes will be attenuated exponentially on both directions along waveguide 13. In Table 1 below, the attenuation for unit length is calculated for a number of modes of circular and rectangular waveguides. The way a useful nesting field is obtained is schematically illustrated in FIG. 3(b). A resonant circuit formed by the inductive part 15 and the tuning capacitive part 16 is inserted at position 14 inside BCW 13. In this example, this resonant circuit is assumed to have a Q-factor of about 10, and its inductive part 15 is substantially working as a radiator, with the current flow 17 exciting the modal fields. This resonant circuit is storing an energy proportional to the Q-factor and an energy balance or a power balance shows in simple explanatory terms how it is possible to transfer a given power level from power source 18 to external load 4 through waveguide aperture 2 without any further losses than those on cables, dielectrics and the waveguide walls. If power source 18 is assumed delivering energy under steady state conditions and that supplies 100 Watts to the resonant circuit through the lossless feeding cable and matching device 19, the power stored in this resonant circuit may be evaluated to be $100 \times Q$ Watts c.a. and at position 14 inside waveguide 13, the intensity of the EM field vectors excited by the resonant circuit will correspond to this power level. The attenuation of the EM power from position 14 along BCW 13 is represented diagrammatically as decaying curve 20 in FIG. 3(b) and it may be seen that the power level is reduced to $\sim 100$ Watts at a distance $L_E$ from position 14 depending on the $\alpha$ value. If the waveguide aperture 2 is at this distance from the exciter, BCW 13 can deliver 100 Watts c.a. of EM power to a matched external load. For the present purposes, $L_E$ is the evanescent mode most effective exciting range of BCW 13. BCW 13 may either be back terminated by short 21 or be left with an aperture which mirrors active aperture 2. If the mirror aperture is left matched in open space, the EM energy transferred by the evanescent modes in this direction will be almost totally reflected back to the source with a low level of stray EM radiation in open space. The same would occur at the active aperture 2 if left unmatched as in open space. This feature confers a high degree of freedom from hazards to exposure to EM fields when the BCW aperture is not properly loaded, as during pre-treatment adjustments. Thus, the transfer of considerable EM power from source 18 to tissue 4 through TE or TM evanescent modes of BCW 13 is accomplished with high efficiency and low EM hazards.

Moreover, no cooling bolus is required between aperture 2 and tissue 4. The air gap 3 is of non-critical length and may practically be changed from 0.5 cm up to a few cm with only a decrease of coupling efficiency and slight tuning and matching adjustments. At higher frequencies, a bolus would help the matching, although the efficiency improvement does not appear significant. This very useful feature is explained if one considers that a low frequency air-filled waveguide working below cutoff exhibits an inductive characteristic admittance of body tissues (R. E. Collin, Foundations of Microwave Engineering, McGraw Hill, N.Y.), allowing a transfer of EM energy with a coupling efficiency never below 90 percent.

In FIG. 4, a front view of the circular cross section of aperture 2 of BCW 13 of FIG. 3(b) is shown together with the normalized EM power density pattern, when only the dominant $TE_{11}$ mode is excited (see FIG. 2(b)). Textbook iso-density contours 22 and 23 are relative to 90 percent and 50 percent of the central maximum power density level, respectively, with contour 23 approximately defining the fixed effective heating field size of this aperture device.

$f_c$ is calculated for simple waveguide cross section and for each mode by simple textbook formulae. For the $TE_{mn}$ and $TM_{mn}$ modes of a rectangular cross section waveguide of dimensions a and b (a>b)(Equation [2]) and a circular waveguide of diameter D (Equation [3]), all measured in meters is:

$$f_{c,rect} = 149.9 \, [(m/a)^2 + (n/b)^2]^{\frac{1}{2}} \quad [2]$$

$$f_{c,circ} = K_{mn}/D \quad [3]$$

In Equation [3], the textbook $K_{mn}$ values are reported in Table 1 below for a number of lower modes (higher symmetry modes) together with the calculated values of the cutoff frequency $f_c$ (see Equations [2] and [3]) for a 20 cm×10 cm rectangular cross section waveguide and for circular cross section waveguides of 10 cm and 20 cm diameter, respectively. Only lower TE modes are considered to show trends. In the same Table 1, the approximated value of the attenuation per unit length (see Equation [1]) is also reported, assuming that the working frequency f is f<<$f_c$, as it is the case if f=27 MHz, whereby Equation [1] becomes $\alpha \sim 0.020944 f_c$.

sible to develop BCWs of acceptable attenuation per unit length and still have a size useful for treatment of more superficial tissues also at the FCC approved medical frequencies up to 2450 MHz.

However, the attenuation coefficient is shown to increase rapidly for superior modes and more rapidly for cylindrical BCWs than for rectangular ones. This behavior has to be taken into account in the design of a mode-weighted multi-modal heating field by considering also the position of the exciters inside the BCW, i.e., by selecting individual distances from the aperture within the $L_E$ range for each mode exciter according to the weight in the multi-modal field that has been designed for each modal component.

In FIG. 5, a front view of geometrical and irregular waveguide cross sections are shown, with some of the low $TE_{mn}$ modes supported and described by E-field vector lines 12. In FIGS. 5(a) and 5(b), the rectangular cross section 24 is shown to support the dominant $TE_{10}$ and $TE_{01}$ modes, respectively. In FIG. 5(c), the square cross section 25 is shown to support both lowest and fundamental $TE_{10}$ and $TE_{01}$ degenerate modes. In FIGS. 5(g) and 5(h), the superior $TE_{20}$ and $TE_{30}$ modes of 24 show nodal (E=0) planes 26 for the E-Field, across which a phase reversal occurs. In FIGS. 5(d), 5(e), and 5(f), the circular cross section 27 is shown to support the $TE_{11}$, $TE_{12}$, and $TE_{21}$ modes respectively, with the two superior ones exhibiting nodal planes 26. In FIGS. 5(i) and 5(l) a distorted rectangular cross section 28 is shown to support distorted $TE_{01}$ and $TE_{10}$ modes respectively. In FIG. 5(m), an E-Field distribution approximating the $TE_{10}$ mode is shown for the distorted and irregular rectangular waveguide cross section 29. For the purpose of this invention, all allowed transversal modes for cross sections of any shape and size may in principle be excited as evanescent modes and used for delivering multi-modal heating fields for specific therapeutic purposes.

In FIG. 6, a number of simple embodiments are schematically illustrated for selectively exciting lower modes, including the fundamental $TE_{10}$ (or $TE_{01}$) and $TE_{11}$ modes in rectangular, or square, or cylindrical waveguides, respectively. The exciting mechanisms illustrated here may easily be extended by analogy to any mode and in BCWs of any cross section size and shape. The transfer of energy by a resonant exciter to a waveguide mode is well known to people knowledgeable in electromagnetism and is described in most microwave textbooks and is accomplished by symmetry congruent coupling of either the E-field or H-field of the exciter to the waveguide modal E- or H-field, respectively (Ch. 8 in: S. Ramo et al., Fields and Waves, J. Wiley & Sons, 1965). One simple way of looking at

TABLE 1

| | CIRCULAR BCW (D = 10 cm) | | | CIRCULAR BCW (D = 20 cm) | | | RECTANGULAR BCW | | | |
|---|---|---|---|---|---|---|---|---|---|---|
| | | | | | | | (a = 20 cm) | | (b = 10 cm) | |
| | $TE_{11}$ | $TE_{21}$ | $TE_{12}$ | $TE_{11}$ | $TE_{21}$ | $TE_{12}$ | $TE_{10}$ | $TE_{01}$ | $TE_{20}$ | $TE_{30}$ |
| K | 175.7 | 291.5 | 508 | 175.7 | 291.5 | 508 | — | — | — | — |
| $f_c$ | 1760 | 2915 | 5080 | 884 | 1458 | 2540 | 750 | 1500 | 1500 | 2250 |
| | 0.37 | 0.61 | 1.10 | 0.26 | 0.30 | 0.53 | 0.05 | 0.31 | 0.31 | 0.47 |

($f_c$ is in MHz; $\alpha$ is in dB/cm).

In Table 1, it is seen that the cutoff frequency of the dominant mode, which is the lowest for each waveguide, is always much higher than the frequencies customarily used for external superficial applicators that fall within the 13.56–433. MHz range and includes shortwave diathermy frequencies. In any case, it is posthis problem is to have the current (i.e. the E-field) lines of the source flow parallel to the current (i.e. the E-field) lines of the waveguide mode in proximity of the highest density points of these. However, the effective position of the exciter has to be seen as an impedance matching problem, and, if the exciter position is fixed, further matching means may be required. In FIG. 6, any details regarding the energy transfer from the power source (not shown in FIG. 6) through coupling and matching devices (not shown in FIG. 6) are omitted, and all exciters are supposed to be within the effective exciting range $L_E$ of the BCW wanted modes.

Figure 6B:
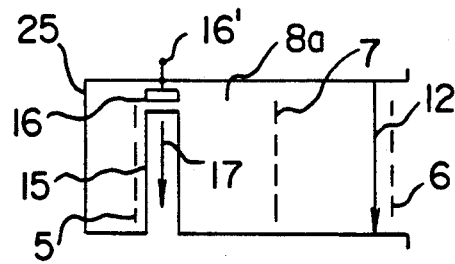
FIG. 6 (a)-(d) are schematic views with parts cut away of alternative embodiments of passband waveguides according to the invention with distributed, semi-distributed and lumped resonant radiator embodiments exciting evanescent modes.
Figure 6A:
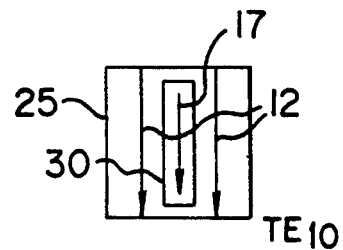

In FIG. 6(a), the resonant aperture 30 works as an exciter laying on a cross section plane of square waveguide 25, shown by a front view. Aperture 30 is characterized by current (E-field) lines 17, which are exciting the $TE_{10}$ mode of 25, since line 17 flows parallel to current lines 12. This distributed constant exciter embodiment is employed in the high frequency range.

For exciting in the mid-frequency range the dominant $TE_{10}$ (or $TE_{01}$) mode of square cross section BCW 25 of PPA 8a is illustrated in FIG. 6(b) with half a section cut away. The semi-distributed and inductive transmission line section 15 is connected across parallel waveguide walls, so that E-field lines 17 couples to E-field lines 12 of the $TE_{10}$ or ($TE_{01}$) mode. The low tuning capacitance 16 is implemented by sliding electrode 16' grounded to the BCW wall.

In FIG. 6(c), an exciter embodiment is shown which is usefully employed in the low frequency range. Here the exciter is embodied by a lumped resonant circuit inside rectangular BCW 24 of PPA 8a shown by the side view of a cutaway section and includes lumped tuning capacitor 16, together with lumped inductive part 15, which takes the form of a single loop across which current 17 flows and excites the $TE_{10}$ mode of 24.

In FIG. 6(d), a further embodiment of the lumped resonant exciter of FIG. 6(c) is shown, in which the lumped tuning capacitance 16 is placed outside BCW 24 of PPA 8a, for easier tuning adjustments and for avoiding the excitation of unwanted modes by its electrical connections.

The lower the symmetry of the waveguide cross section, the higher the mode together with the number of E-field nodal surfaces that are plane only for lower modes. It follows that it is difficult to implement an exciter for individually exciting low symmetry modes without exciting some higher symmetry ones as well The reverse is also true, since the lowest modes are most favored in the distribution of the EM energy among all the transversal modes; thus, the possibility of individually exciting high symmetry modes, without exciting some lower symmetry ones requires a very careful exciter symmetry design and implementation.

In FIGS. 7 and 8, practical embodiments of low frequency lumped element exciters according to the invention are shown by way of examples by front views of the rectangular cross section BCW 28.

In FIG. 7, the inductive part of the exciter is embodied by multi-turn coil 31 wound on coil former 32. The current loops 17 lay substantially on BCW longitudinal planes and are efficient exciters for $TE_{10}$, whose E-field lines 12 spread across the extended cross section of BCW 28. (see FIG. 5(a)).

In FIG. 8(a), there is shown a practical embodiment for the excitation of the higher $TE_{20}$ mode of 28 by the single rectangular loop 33 laying on the waveguide transversal plane, and with the exciting out of phase currents 17 and 17' flowing parallel and in phase with $TE_{20}$ mode lines 12 and 12', respectively, laying in different cross section semi-planes. However, the current line 17" on the upper arm of the exciting loop is flowing parallel to the E-field vector 12" of mode $TE_{01}$ of BCW 28, which would also result excited. To avoid this mode to contribute to the modal field of BCW 28, a conductive rod or sheet 34 is electrically connected between the shorter walls of waveguide 28. In this way, the E-field vector 12" of mode $TE_{01}$ is short circuited, and the relative modal field component is suppressed.

Filtering embodiments may be applied to reject the transmission of energy through unwanted TE and TM modes of any BCW. In one embodiment, metallic rods or thin laminae are introduced inside the waveguide laying parallel to the E-field which is to be attenuated, but perpendicular to the one that should propagate. In other embodiments, slots are cut along the waveguide walls which are perpendicular to the unwanted mode, but parallel to the direction of the currents of the wanted one.

In FIG. 8(b), the $TE_{30}$ mode of rectangular BCW 28 is excited by the 8-shaped loop laying on a transversal BCW plane. It is to be noted that the phase of the exciting currents 17 and 17' are coherent with those of the $TE_{30}$ mode in each of the three regions delimited by the two nodal planes 26 (see FIG. 5(h)).

In FIG. 9(a), both $TE_{10}$ and the $TE_{01}$ modes of rectangular BCW 28 are simultaneously excited by an orthogonal dual-exciter configuration embodied by a series-coil circuit. With this exciter embodiment, the $TE_{10}$ mode (see FIG. 5(a)) is excited by the parallel current lines 17 of multiturn coil 31, while the $TE_{01}$ mode (see FIG. 5(b)) is excited by the current line 17' of the single current line 36, connected in series to the former, and therefore being crossed by the same current intensity. By differentiating the number of turns of the exciter coils, a control of the energy transfer in each mode is accomplished.

In FIG. 9(b), the same modes of FIG. 9(a) are instead excited by the two orthogonal coils 31 and 31' connected in parallel, a modality which also allows control of the individual intensity of currents 17 and 17' for a control of the energy transfer on each mode.

More complex series-parallel circuit networks of various symmetry may be adopted for the multiple excitation of a selected number of modes with a control of the individual energy transfer to each mode. It is observed that both series and parallel networks of resonant exciters may share a common tuning capacitor, which renders these embodiments of both practical and less expensive to manufacture.

The resonant coil embodiments that have been illustrated as exciters in FIGS. 6, 7, and 8, may work as well as direct radiators, provided that their position fall also within the whole $L_R$ range, and that are configured to emit the direct heating field of the required shape. The reverse is also true, whereby any direct radiator embodiments can be used as exciters as well, provided that they are positioned within the $L_E$ range and their symmetry is congruent with the modes to be excited. Moreover, it will be apparent that any radiator embodiment can work as exciter as well as direct radiator, provided that its position falls within the $L_{RE}$ range and is configured to produce at the same time a direct field of suitable shape and intensity and the excitation of the wanted modes.

It will be shown that the integration of direct radiator embodiments into the BCW body, as for the CPA or SCPA or PCPA or MPA embodiments or into the BCW aperture for the RA embodiment, substantially improves both the safety and heating efficiency features of the direct radiators. This is true for direct radiator embodiments of any type or size, or conformation or configuration or frequency, and it is one of the important features of the invention.

Figure 10A:
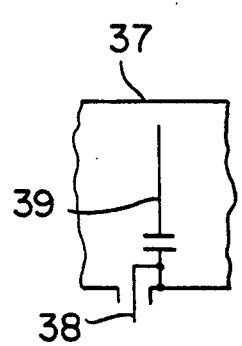
FIGS. 10(a) and (b) are schematic side views with parts cut away of alternative embodiments of high frequency distributed resonant radiators in a below cutoff waveguide for producing direct or modal heating fields of hyperthermia applicators.
Figure 10B:
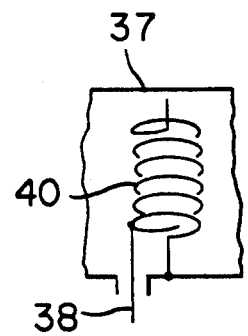
Figure 11A:
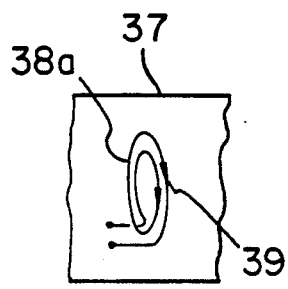
FIGS. 11(a)-(e) are schematic side views with parts cut away of alternative embodiments of hyperthermia applicators provided with resonant lumped coil radiator alternative embodiments for producing direct or modal fields.
Figure 11B:
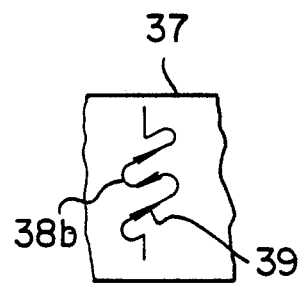
Figure 11C:
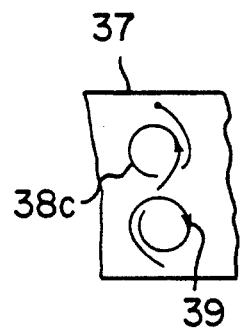
Figure 11D:
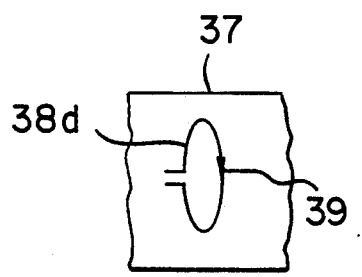
Figure 11E:
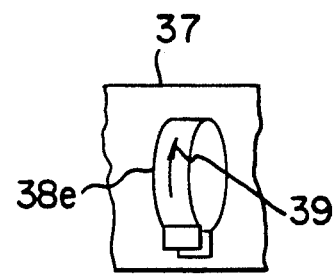

FIG. 10 illustrates side views of BCW 37 with parts cut away incorporating distributed radiator embodiments which may be used in the high frequency range for producing direct therapeutic field or for exciting BCW modes. The feeding of these radiators by the power source (not shown in FIG. 10) occurs through the adjustable coupling and matching asymmetric tap 38 although other coupling and matching embodiments may be employed as well. The radiating embodiments are the resonant monopole 39 (FIG. 10(a)) and the distributed constant helix 40 (FIG. 10(b)). Other high frequency embodiments may be employed as EM radiators within the purposes of the invention, including the resonant aperture radiator of FIG. 6(a).

FIGS. 11 and 12 illustrate side views of BCW 37 with parts cut away incorporating some lumped radiator embodiments which may be used in the low frequency working range. The current flow lines 39 in these lumped inductive part embodiments are active in producing a direct therapeutic field or in exciting BCW modes, or both.

The radiator shapes or configurations of FIGS. 10, 11, and 12 are currently employed as applicators for mild shortwave diathermy treatments and occasionally for hyperthermia tumor treatments. However, the main problem with any such radiators and above all with the coil embodiments of FIG. 11 is that they have exhibited patient safety problems when energized at full treatment power. In fact, subcutaneous fat overheating always arises, causing skin burns, on account of the stray E-field between radiator parts due to the high impedance exhibited at the working frequency. Moreover, their heating field distribution shows a significant non-uniformity substantially due to the stray E-field distribution along the high impedance inductive circuit. This calls for safer treatment conditions at reduced power, a limitation which decreases the penetration potential. Furthermore, all the relative embodiments of the prior art exhibit large EM stray fields and therefore EM hazards.

A few simple considerations will help to explain why, if the same radiators are incorporated into a BCW as in the HPA embodiments disclosed in the invention, substantial improvements are accomplished in terms of access tissue safety with respect to the prior art embodiments.

With regard to the CPA or SCPA or PCPA or MPA embodiments, the local heating field is composite field generated by two independent mechanisms. This implies that there are two access routes to the target tissue, each transferring a portion of the total power delivered and this adds improved safety to the treatment. Furthermore, for all the HPA embodiments of this invention, the direct radiators may be withdrawn many centimeters from the body surface inside the BCW and within the $L_R$ range until the superficial overheating due to the rapidly decaying stray E-fields is within acceptable limits. In a prior art lumped or distributed radiating device positioned in open air a few centimeters from a body surface, the intensity of the heating field rapidly vanishes on account of the energy spread in open space. In addition, it appears that the BCW electromagnetic boundary positively modifies the stray E-field, an effect distinctly observed with the aperture-conditioned direct radiators of the RA embodiments. These improvements have been substantiated by experimental in vitro tests.

Figure 12A:
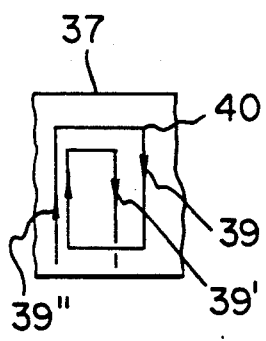
FIGS. 12(a)-(e) are schematic side views with parts cut away of alternative embodiments of hyperthermia applicators provided with alternative resonant lumped magnetic dipole radiator embodiments for producing direct or modal fields.
Figure 12B:
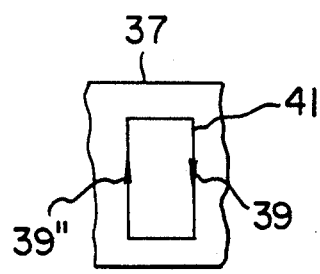
Figure 12C:
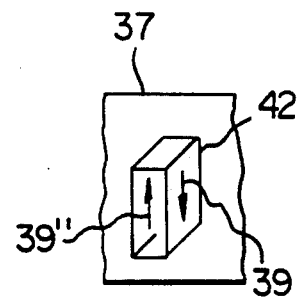
Figure 12D:
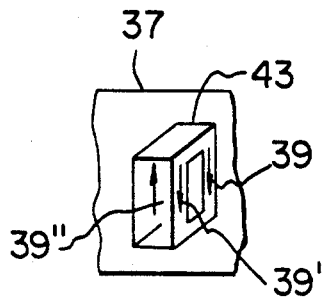
Figure 12E:
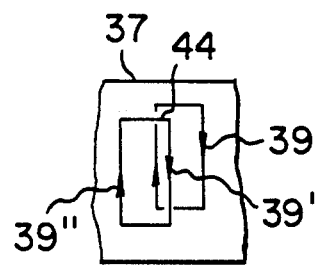

In FIG. 11, side views of BCW segments 37 are shown with parts cut away, which are incorporating some currently used conformations of lumped inductive radiators whose current lines 39 flow in flat coils 38 laying across transverse BCW planes. e.g. flowing parallel to the body surface (not shown in FIG. 11). Hereinafter, the embodiments of FIG. 11 are referred to as coil radiators. Details about the power source, the feeding circuit and the matching and tuning means are not shown in FIG. 11. In FIG. 11(a), the flat spiral or pancake coil embodiment 38a is shown. In FIG. 11(b) the flattened solenoid or Side-Turner embodiment 38b is shown. In FIG. 11(c), the flat S-shaped coil embodiment 38c is shown. All these coil embodiments are high impedance devices and a considerable radio frequency voltage drop is found within their extremities with consequent high stray E-field intensities. The single loop coil radiator 38d of FIG. 11(d) exhibits a lower impedance, while the lowest impedance is exhibited by the cylindric single turn coil embodiment 38e, in which distributed parallel current lines are flowing along the large cylinder conductive surface. The flat transverse radiators of FIGS. 8(a) and (b) are thus coil radiators. FIG. 12 illustrates side views with parts cut away of BCW segment 37 incorporating various types of magnetic dipoles with the currents lines 39 flowing on flat loop embodiments, usually of rectangular conformation, laying along longitudinal planes of BCW 37 and therefore perpendicular to the body surface (not shown in FIG. 12). In FIG. 12(a) the multi-turn rectangular dipole 40 is shown. In FIG. 12(b), the single turn rectangular dipole 41 implemented by a conductive wire conductor is shown. In FIG. 12(c) the single dipole is implemented by the folded metal ribbon conductor embodiment 42 along which distributed currents flow, a variant of which is the multi-distributed current dipole 43 of FIG. 12(d). In FIG. 12(e), the side-to-side parallel twin-dipole embodiment 44 is illustrated. In all dipole embodiments to the heating field due to currents 39 flowing on the loopside proximal to the body surface is superimposed the field due to the out-of-phase return current 39" flowing on the symmetric distal loopsides, a presence which affects the heating when the latter are close to the body surface. The longitudinal radiator of FIG. 6(c) may be considered a single dipole radiator. When used as direct radiators, the dipoles feature an improved penetration with respect to the coil radiators due to the perpendicular configuration of the former with respect to the body surface, which reduces the intensity of the stray E-fields impinging upon superficial tissues.

Figure 13A:
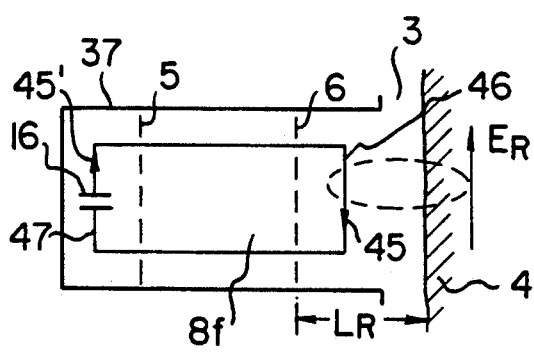
FIGS. 13(a) and (b) are schematic side views with parts cut away of embodiments of hyperthermia applicators provided with alternative lumped resonant line current radiator embodiments for producing a direct heating field and means for removing unwanted distal conductor heating field contributions.

FIG. 13 discloses embodiments of the RA 8f and 8f' implemented with further lumped H-field radiator embodiments for low frequency work integrated into BCW 37. These newly disclosed radiating embodiments carry some useful advantages over coil and dipoles, and can be used as direct radiators as well as exciters or both. The radiating radiofrequency currents 45 are flowing along the single conductor carrying line 46, which in FIG. 13 is embodied as a direct radiator and is positioned within the $L_R$ range of 8f and 8f'. The return currents 45' are flowing in conductors positioned outside this range and do not contribute to any fields. Hereinafter, this type of radiator embodiments is referred to as line current radiators or line radiators. In the embodiment of FIG. 13(a), the distal loopside 47 is withdrawn beyond position 7 inside the BCW and out of the whole $L_R$ and $L_E$ ranges (see FIG. 1).

Figure 13B:
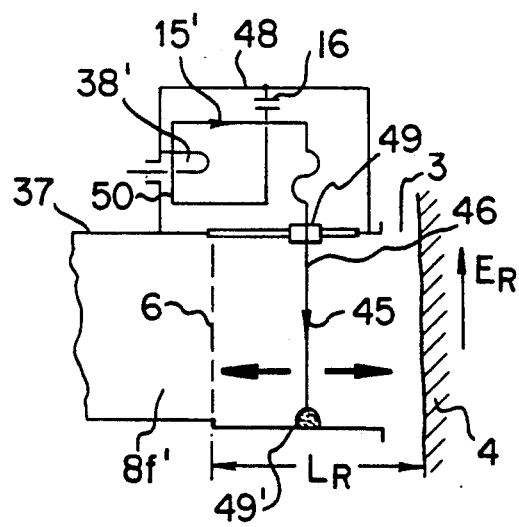
Figure 14A:
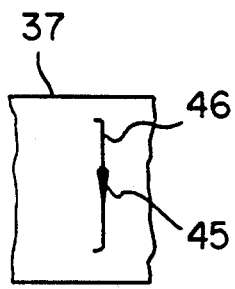
FIGS. 14 (a)-(g) are schematic side views with parts cut away of alternative embodiments of hyperthermia applicators provided with alternative lumped resonant line current radiator embodiments for producing direct or modal fields.
Figure 14B:
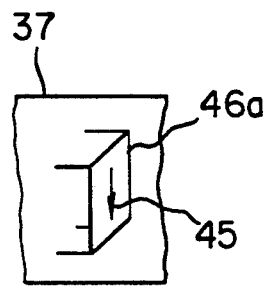
Figure 14C:
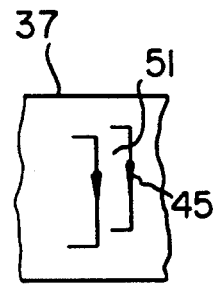
Figure 14D:
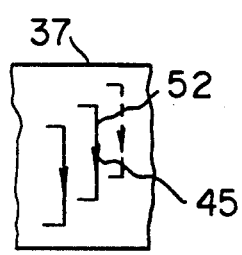
Figure 14E:
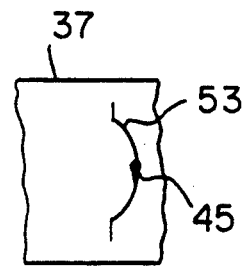
Figure 14F:
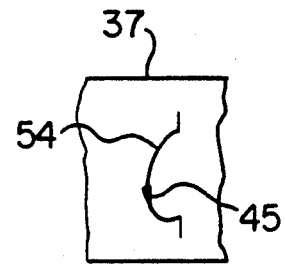
Figure 14G:
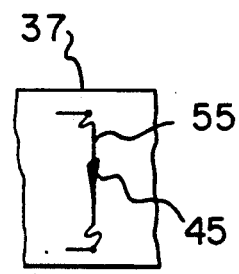

A further line radiator embodiment is the RA embodiment 8f' of FIG. 13(b), wherein the circuit of the line radiator 46 is electrically closed outside waveguide 37 within a shielded box 48 with the return current 45' flowing across conductive walls 48 and not substantially contributing to the heating field. Line radiator 46 is provided with sliding devices 49 (isolated from the BCW wall) and 49' (grounded to the BCW wall) which can be shifted longitudinally in both directions to be positioned within the whole $L_R$ range at a variable separation from tissue 4, in order to control the $E_R$ intensity. In the RA embodiment of FIG. 13(b) the matching and tuning means of line radiator 46 are enclosed in the shielded box external to BCW 37 for improved practicality of operation and lower manufacturing complexity, allowing independent adjustments of in-field interchangeable exciters, and avoiding accidental excitation of unwanted modes. The coupling and matching loop 38' is of the asymmetric inductive type and couples to a further inductive part 50 of the line radiator circuit for an efficient energy transfer to radiator 46.

In FIG. 14, some basic embodiments of line radiators are illustrated. In FIG. 14(a), a single-line radiator 46 is shown, while its distributed current version 46a is illustrated in FIG. 14(b). In FIGS. 14(c) and 14(d), twin-line radiator 51 and multiple-line radiator 52 are shown, respectively. In FIGS. 14(e) and 14(f), curved line radiators 53 and 54 are shown, which are laying on longitudinal and transverse planes of 37, respectively. In FIG. 14(g), the flexible line radiator 55 is shown, the conformation of which may assume a variety of 3-D conformations and configurations and may be used also for adjusting the heating field following the treatment changes during a treatment session. Further conformations and configurations of line radiators may be added or derived from the basic ones illustrated in FIG. 14.

Figure 16A:
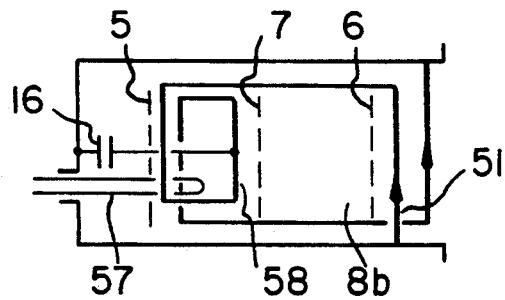
FIGS. 16(a)-(f) are schematic side views with parts cut away of further embodiments of hyperthermia applicators provided with symmetric radiators.
Figure 16B:
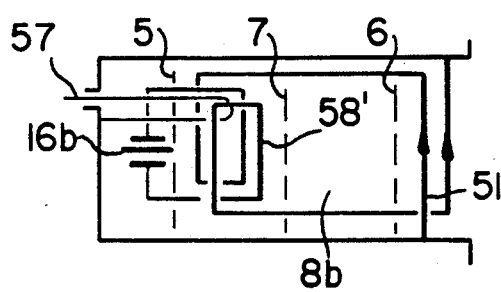
Figure 16C:
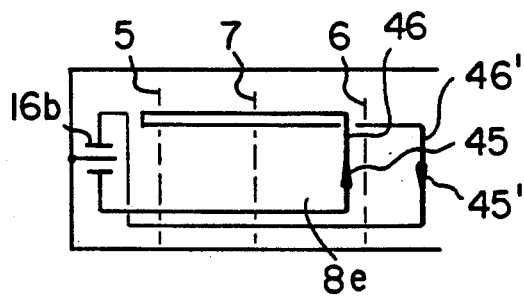
Figure 16D:
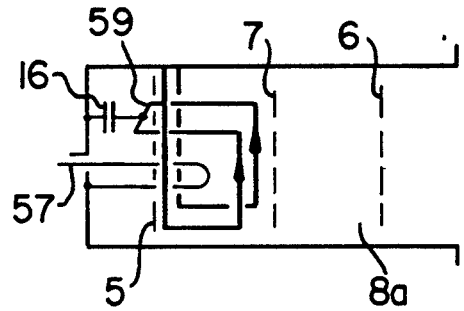
Figure 16E:
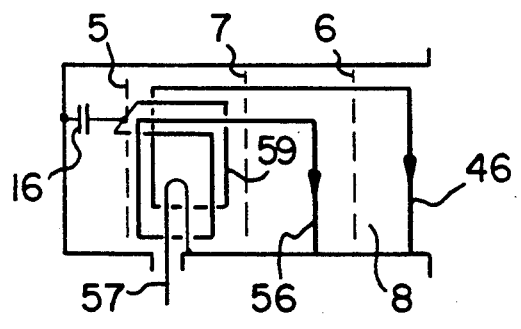
Figure 16F:
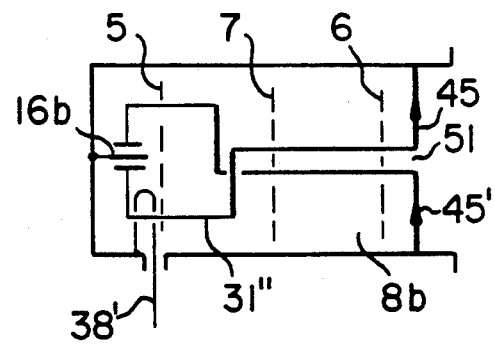
Figure 17:
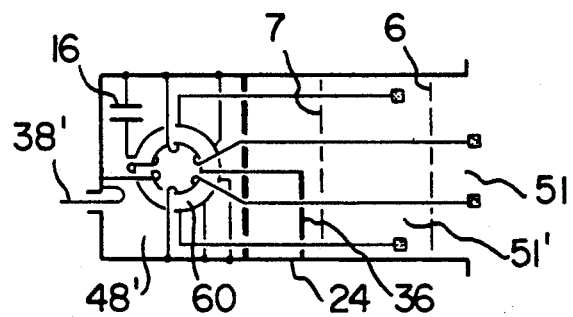
FIG. 17 shows a schematic top view with parts cut away of a multi-radiator embodiment of a hyperthermia applicator.

Embodiments for HPA applicators according to the invention are described with the help of FIGS. 15, 16 and 17. Exciters and radiators are schematically illustrated by way of circuit combinations and are not optimized to excite any particular evanescent modes or produce $E_R$ fields of particular intensity or orientation. Basic coupling and matching embodiments are schematically illustrated only in some drawings by the way of examples. In the applicator embodiments shown, the combination of BCWs, exciters, radiators, tuning and matching means should be taken as examples and are not intended for limiting further combinations or extensions.

Figure 15A:
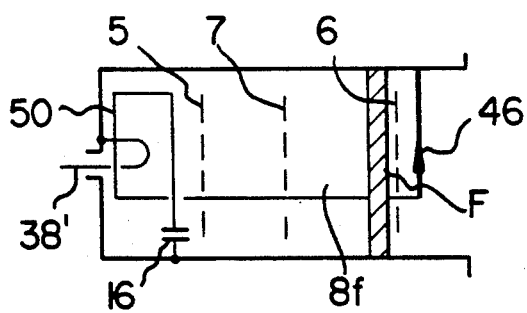
FIGS. 15(a)-(d) are schematic side views with parts cut away of embodiments of hyperthermia applicators provided with asymmetric radiators.

FIG. 15(a) illustrates an RA embodiment 8f, in which single-line radiator 46 works within the $L_{PR}$ range. The coupling and matching means are implemented off the $L_E$ range by loop 38' coupling to the further inductive part 50 of the line radiator circuit for an efficient power transfer to 46. A modal filter F is inserted to suppress accidental BCW mode excitation.

Figure 15B:
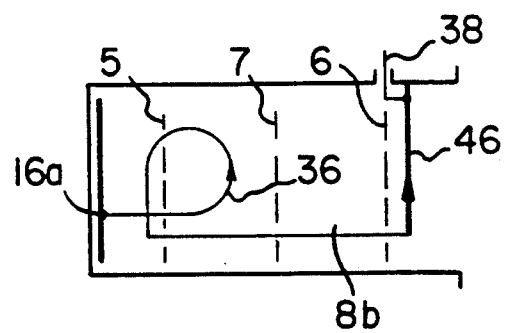

FIG. 15(b) illustrates a side view with parts cut away of a CPA embodiment 8b, in which single-line direct radiator 46 is within the $L_{PR}$ range in combination with single-line exciter 36 within the $L_{PE}$ range. The tap matching embodiment 38 as illustrated may as well be implemented at the other terminal of the radiator circuit. The tuning capacitance is implemented by distributed capacitor 16a in which the ground electrode is the BCW inner wall itself. In alternative embodiments, air (or vacuum) dielectric capacitors are preferred for use with the high power required, in order to avoid the heavy losses on the dielectrics and keep tuning stability during long (1 hour c.a.) treatment sessions.

Figure 15C:
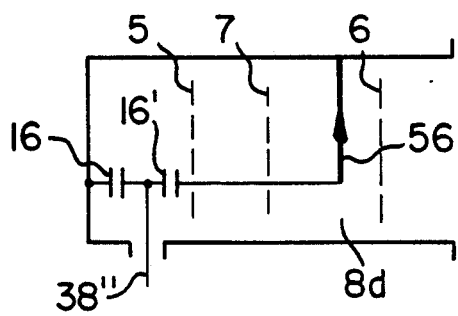

FIG. 15(c) illustrates a side view of MPA embodiment 8d, in which single-line exciter-direct radiator 56 is within the $L_{ER}$ range. The matching and tuning embodiment 38'' is standard network including two variable capacitor 16 and 16' circuit, resonating with the inductance of 56.

Figure 15D:
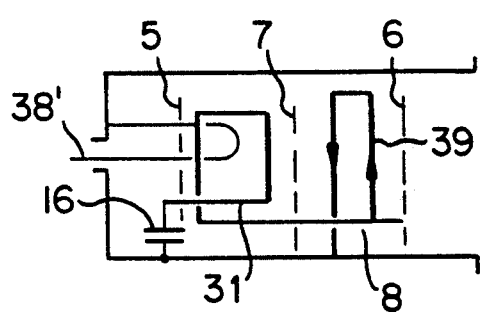

FIG. 15(d) illustrates a side view with parts cut away of alternative SCPA embodiment $8_C$ in which dipole mixed exciter/radiator 39 is within the $L_{RE}$ range. The matching loop 38 is seen coupling directly to coil exciter 31 for improved coupling efficiency and circuital simplicity. In this as well as in the CPA embodiment of FIG. 15(b), exciter and direct radiator are connected in series and energized by the same current intensity for feeding circuit simplification. The power ratio between $E_R$ and $E_E$ fields may be controlled by the adjustment of other parameters, such as radiator position, exciter coil turns, radiator sizes, shapes and configurations.

FIG. 16 illustrates side views with parts cut away of alternative circuital embodiments in which line direct radiator embodiments are implemented with the currents flowing in the same direction or in the reverse direction.

FIG. 16(a) shows a CPA embodiment 8b in which twin-line direct radiator 51 is within the $L_{PR}$ range and works in combination with the multi-turn dipole exciter 58 within the $L_{PE}$ range. With this embodiment, currents with the same direction of flow along the two direct radiator lines are symmetrically grounded to the BCW inner wall to provide very low stray E-field and therefore can be made working at closer distance from the body surface with improved penetration. The direct radiator electrical symmetry is respected by the symmetric matching loop 57 coupling directly to coil exciter 58, and by the grounding of tuning capacitor 16 tapping to ground exciter 58 electric center.

FIG. 16(b) illustrates alternative CPA embodiment 8b, in which multi-turn dipole exciter 58' is centrally grounded by the three electrode variable tuning capacitor 16b. This tuning embodiment is particularly useful for single or multiple radiators working at low and mid-range frequency with symmetric radiator circuits.

FIG. 16(c) shows PCPA embodiment 8e in which line direct radiators 46 and 46' are within the $L_{PR}$ and $L_{RE}$ ranges, respectively, and currents of opposite direction 45 and 45' flow on the two line, respectively. The radiator electric symmetry and the grounding towards the BCW inner wall is provided by the ground connection of the 3-electrode tuning capacitor 16b central electrode. This applicator embodiment is versatile in spite of its simple circuitry and is easily transformed into an embodiment with currents flowing in the same direction by the simple inversion of the connecting wires to the radiators.

FIG. 16(d) illustrates the PPA embodiment 8a, in which the parallel-dipole exciter 59 is within the $L_{PE}$ range. This embodiment generates currents with the same direction on the dipoles 51 which are grounded to the BCW inner wall. The direct radiator electric symmetry is respected by the symmetric matching loop 57 coupling directly to parallel-coil exciter 59 whose center tap is grounded to the BCW inner wall by tuning capacitor 16.

FIG. 16(e) illustrates the HPA embodiment 8 of an applicator according to the invention, in which all three sets of radiating elements are implemented, and the single-line direct radiator 46 is within the $L_{PR}$ range and works in combination with both parallel-dipole exciter 59 within the $L_{PE}$ range and with the exciter/radiator 56 within the $L_{RE}$ range, for extended versatility in providing the most complex heating pattern. The specific embodiment illustrated generates currents of the same direction on line radiators 46 and 56 which are grounded to the BCW inner wall. The symmetric matching loop 57 is coupled to parallel-dipole exciter 59 whose center tap is grounded to the BCW inner wall through tuning capacitor 16.

FIG. 16(f) illustrates alternative CPA embodiment 8b for providing currents of opposite directions 45 and 45' twin-line direct radiator 51. For this purpose, the exciter 31" is inverting the current wires supplying the line radiators.

FIG. 17 illustrates a top view with parts cut away of an applicator system according to the invention and based on rectangular cross section BCW 24 designed to host a versatile multi-radiator embodiment. An external shielded control box 48' is provided for hosting the tuning capacitor 16 and the symmetric coupling and matching loop 38' together with a power splitter embodiment. This includes toroidal radiofrequency transformer 60 whose primary is coupled to loop 38' and capacitor 16, and whose five secondary circuits are feeding single-line exciter ($TE_{10}$) 36, the twin-line exciter-radiator 51' and twin-line direct radiator 51. The power level of each secondary current may be controlled by the relative transformer ratio. The relative phase of the secondary currents may be shifted 180° by switching the secondary-to-radiator wiring. It should be noted that, for a time-dependent control of the power level to number of the five radiators of the applicator embodiment of FIG. 17, it is sufficient to interpose a multi-channel radiofrequency switch between control box 48' and BCW 24.

Variable coupling and matching means are required for coupling the power source to radiators with adequate efficiency and stability. In addition, variable tuning means are required for adjusting the intrinsic frequency of resonators to the power source frequency. Both matching and tuning means have to be differently embodied according to the frequency range, the type and number of radiators and their use as exciters or direct radiators. Preferred tuning and matching embodiments are disclosed which fall under the scope of the invention and present the advantage of stability and of smooth control, a feature useful during treatment sessions for adjusting the power delivered in conjunction with tissue and position modifications during treatment sessions. Moreover, they appear simple to operate and suited for automatic control through servos driven by process control computers and can be manufactured with low cost and proven technology.

Figure 18A:
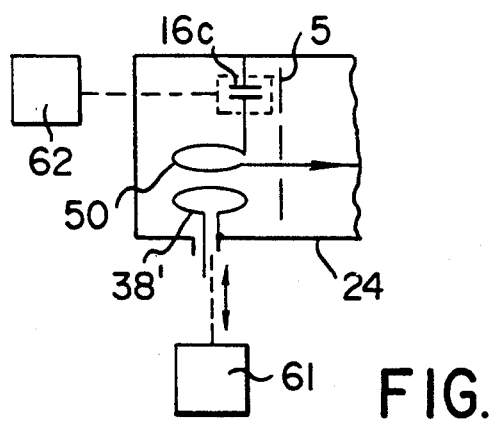
FIGS. 18(a) and (b) show schematic side views with parts cut away of magnetic matching control embodiments for asymmetric radiators of hyperthermia applicators.
Figure 18B:
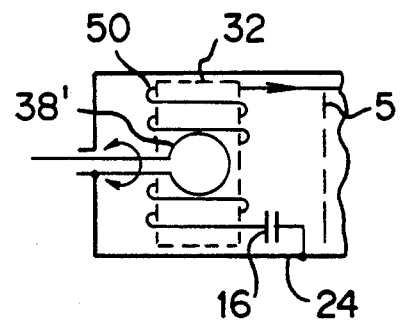

In FIGS. 18(a) and 18(b), side view with parts cut away are illustrated of BCW 24 incorporating two lumped coupling and matching loop embodiments of the inductive type, which are supplying the EM energy from the power source (not shown in FIG. 18) to a radiator (not shown in FIG. 18) in the low and mid-frequency ranges. In FIG. 18(a), the EM energy is supplied to the applicator via a cable terminated by loop 38' which couples to the coil 50, which is terminating the inductive part of a radiator, through a variable transformer type of coupling. The coupling extent is controlled by a coaxial displacement of loop 38' until the reflected power is at the minimum. The displacement of 38' can be set to a null point for the best matching also by an automatic servo mechanism. In this embodiment, this is performed automatically by the computer controlled servo drive 61. The tuning embodiment is implemented by vacuum condenser 16c whose capacitance value is smoothly adjusted by computer controlled servo drive 62.

In FIG. 18(b), the EM energy is supplied to the applicator via a coaxial cable terminated by loop 38' which couples to the radiator terminating coil 50 through a variable magnetic flux coupler type of coupling, the extent of which is controlled by the angle formed by 38' with the magnetic flux line of 50. This angle is adjusted by a rotatable joint until the reflected power is at the minimum. Although not shown in the drawing, the rotation of the coupling loop 38' can be set to a null point for the best matching by an automatic servo mechanism.

Figure 19A:
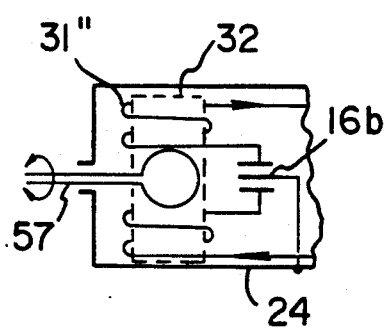
FIGS. 19(a) and (b) show schematic side views with parts cut away of magnetic matching control embodiments for symmetric radiators of hyperthermia applicators.
Figure 19B:
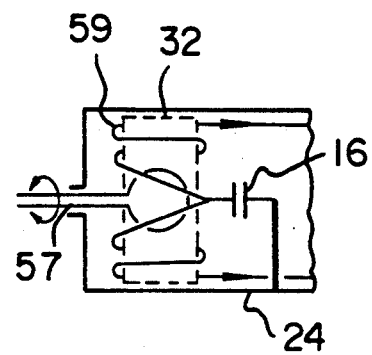

The coupling and matching means of FIG. 18 are also useful for energizing symmetric radiators, as in FIGS. 19(a) and 19(b) in which side views with parts cut away of BCW 24 are schematically illustrated (radiators and sources not shown in FIG. 19).

In FIG. 19(a), the symmetric loop 57, provided of a rotatable joint, couples to the symmetrical coil embodiment 31" (see FIG. 16(b)), which is symmetrically grounded by the 3-electrode capacitor 16b, and the matching is accomplished by adjusting the angle of 57 with the magnetic flux lines of coil 31".

In FIG. 19(b), the symmetric loop 57, provided of a rotatable joint, couples to the symmetric parallel-coil embodiment 59 (see FIG. 16(a)), which is grounded by capacitor 16, and the matching is accomplished by adjusting the angle of 57 with the magnetic flux lines of parallel-coil 59.

The series-dipole embodiment 31" and parallel-dipole embodiment 59 of FIGS. 19(a) and 19(b), respectively, are very simple and yet versatile enough to provide specific power levels to each radiator depending on the effective transformer ratio between each coil segment and feeding loop 57. Moreover, multiple parallel-dipole embodiments may energize a multiplicity of radiator, each to a prescribed power level. Furthermore, loop 57 needs not to be fed by a symmetric line: a coaxial cable terminated by a asymmetric loop like 38' may work as well.

The few basic HPA embodiments disclosed are the basic building blocks of a large variety of HPA configurations, the flexible design of which permits optimization to exploit variations of the HPAs to cope with specific clinical situations which present variable requirements with regard to therapeutic field cross section, size, shape, and penetration. Furthermore, heating modalities are disclosed regarding the HPA usage in connection with specific target volumes, localization and body site conformation as well as with combined tissue treatments, with the purpose of accomplishing enhanced heating of target volumes of any sizes, shapes and depths with the utmost safety.

Air-filled HPAs can be made available with a cross section of any shape and size of clinical interest for the whole popular frequency range employed in deep subcutaneous hyperthermia (13.56–43.3 MHz) or lower in addition to treatments at 2450 MHz for superficial lesions. The HPA manufacturing process can be simple and inexpensive, and further improvements can be made with regard to the handling and the comfortable positioning the HPA over the patient, primarily due to the low weight of the HPA and the air gap between the HPA and the skin. Finally, HPAs can easily be optimized for patient personalized treatments at practically any working frequency right in the clinical environment, since their direct radiators and EM boundaries may be easily and simply modified by unspecialized personnel.

As illustrated in FIGS. 5-8, the number and symmetry of the modes supported by the EM boundary of a BCW are strictly bound to the EM boundary configuration. If these modes are energized by a suitable exciter, these could result in multi-modal fields of variable cross section shapes. Modifications in the composition of the multi-modal heating field can be accomplished by modifying the EM boundary of the BCW segment including the conductive wall cross section size and shape, the aperture, the BCW medium, i.e., the EM parameters of the filler (ferrite, dielectrics) of the BCW, etc.

In alternative HPA embodiments, the contribution of specific evanescent modes to the multi-modal field may be changed by modifying the BCW existing cross section size or shape by mechanically altering the BCW walls which can be manufactured with a flexible conductive part. In further alternative HPA embodiments, a cross section transition BCW segment is added to the active aperture of an existing BCW segment to modify its cross section. In other alternative HPA embodiments, enhanced excitation of higher BCW modes or field distortion is accomplished by loading the BCW with high dielectric constant material of low dielectric losses and by positioning the dielectric slabs where the E-field density is higher and most affected. Moreover, mode filters would further help in the component selection for the multi-modal field, the relative intensity of which is controlled by the exciter position in the $L_{PE}$ or $L_{RE}$ range.

In further multi-modal field controlled embodiments, illustrated in FIG. 20(a) with a side view of HPA 62 with parts cut away, the aperture 2 is occluded by a conductive radiation shield 61, which modifies the EM boundary of the BCW segment 63 at the active aperture. The treatment port 64 cut through shield 61 is excited by the incident multi-modal field of the BCW and by the direct field of line radiator 46 and acts as a secondary field aperture source limiting the size and shaping the contour of the heating field of 62 impinging upon tissue 4 encompassing target tissue 65. Small size ports cut through radiation shields reduce the penetration and should be reserved to more superficial lesions. A large variety of HPA heating field sizes and shapes may be obtained by cutting through one or more treatment ports of suitable size, shape and position over the shied as schematically illustrated in FIGS. 20(b)-(d), showing front views of a circular cross section HPA with parts cut away. FIGS. 20(b) and 20(c) show front views of circular shield 61 on which the circular port 64a and the half-moon shaped port 64b are cut through, respectively. FIG. 20(d) shows a front view of rectangular shield 61a on which the circular ports 64c, d, e are cut through. Also the field of direct radiators 46 of the HPA represented in FIGS. 20(a)-(d) are affected by the presence of a shield and by the size and shape and position of treatment ports such as 64a-e and this can be used to advantage in further shaping of the HPA heating field.

If the aperture size of an applicator could be kept large enough to allow a better penetration while confining the heating over small target volumes, then such an applicator would represent an innovative and substantial improvement in therapeutic heating. This is partially accomplished by another embodiment of an HPA according to the invention and takes into consideration the possibility of minimizing the aperture size increase required by the EM theory for a given penetration improvement. This is explained with the help of FIGS. 20(e) and 20(f) showing front views of two HPAs with rectangular cross section 24 and 24a, respectively, of different transverse dimensions a and b (a>b). A substantial improvement in penetration is obtained without the need of enlarging the BCW aperture, but simply taking a large conductive sheet as 24' and cutting through an aperture matching the cross section of BCW 24, through which the BCW 24 aperture is mechanically and electrically connected as in FIG. 20(e). Thus, the large conductive flange 24' allows the flow of currents from aperture 24 on the perpendicular plane of the flange and in directions which help reduce the EM near fields which have an adverse effect on penetration—the larger the flange size, the greater the penetration improvement, as is well known to experts in electromagnetism. If we consider the fundamental $TE_{10}$ mode of 24 of FIG. 20(f), we observe that the b dimension is substantially irrelevant with respect to the periodicity of modal E-field 12 and therefore of other propagation parameters such as the cutoff frequency etc. (see Equation [2]). In principle, this is true for all those transverse modes, such as the $TE_{10}$, $TE_{01}$, $TE_{20}$, of 24 which have zero periodicity in one transverse axis. Thus, if the $TE_{10}$ fundamental mode of BCW 24 is excited, the only critical dimension determining the penetration of this modal field component appears to be the long side a, which could be extended up to any value compatible with the exciter size, the mode attenuation and the cutoff frequency. In FIG. 20(f), the front view with parts cut away of a preferred embodiment of an extended-side HPA is shown, in which the extended multi-turn exciter 31d is exciting the $TE_{10}$ mode of 24a to produce an heating field size elongated along the x-axis transverse relevant direction, and with a much smaller extension along the y-axis. Both these features potentially optimize a large number of HPAs, from the simplest PPA to the sophisticated SCPA, allowing them to heat efficiently deeper tissues of a large variety of shapes with applicators of minimal cross section size.

The heating field emitted by the HPA direct radiators may be further optimized, giving rise to many possible embodiments all of them falling under the scope of the invention. In one optimized HPA embodiment, the number, size, conformation or configuration of direct radiators is selected to help control the effective size or contour of the HPA direct heating field. In a further HPA embodiment, one or more direct radiators is a passive radiator which is indirectly energized through the EM coupling to radiators energized by the power source.

In one HPA embodiment, the pathway of the direct or multi-modal heating field is preferably modified by the insertion of low loss, high susceptibility ferrite materials within the BCW segment in positions in which the H-field density can be affected.

In further HPA embodiments according to the invention, relative intensity of the direct heating field with respect to the multi-modal field is controlled by mechanical means which are shifting the direct radiator, or the exciter position within their working range.

When an heating field is required for the treatment of tissues extending for a non-negligible depth, then multifrequency modal and direct heating fields may be employed exhibiting components of a varying penetration potential and the HPA includes exciters or direct radiators working at more than one frequency.

Time-averaged heating fields may be produced by a single HPA to match specific tissue contours, depth and heterogenity when the transversal size of the target tissue is smaller than that of the HPA. This versatility to cope with varying heating requirements is an HPA distinctive feature ascribed mostly to the flexibility in the design of direct radiators to produce a variety of direct heating fields. Radiators may be manufactured in flexible embodiments which include conductive multistranded wires, thin ribbons and sheets, flexible plastic tubes filled with liquid conducting means such as electrolytes and mercury. In these embodiments, the conformation of the radiators and their configurations with respect to waveguide walls, aperture or body surface are easily in-field modified to obtain a variety of final radiator conformations and configurations. Moreover, radiators may further be provided with mechanical means scanning flexible radiators among two or more rest conformations or configurations for producing SAR spatial distributions which are time-averaged out from those relative to their rest conformations and configurations. With these embodiments, means are provided for keeping the radiators automatically tuned and matched during scans. In case of switching times negligible with respect to the mean lifetime in the rest and final conformations, the final weighted average distribution will contain the primitive distributions in a ratio equal to the ratio of the respective lifetimes. Analogous results are obtained with an alternative HPA embodiment if the ferrite or dielectric are materials modifying the field pathway to the tissue mechanically scanned over suitable rest and final positions. In alternative HPA embodiments, the cross section—or a treatment port on the radiation shield—is mechanically switched between rest configurations to produce time-averaged multimodal and direct heating fields and corresponding time-weighted averages of their SAR distributions. Time and spatial profiles may thus be generated to keep optimized heating conditions during the treatment, when physiological changes occur which require heating field adjustments.

Time-averaged SAR spatial distributions are also accomplished by the use of electronic switching means, including multiplexing or multi-channel electronic devices, without modifying the conformation and the configuration of direct radiators or exciters but operating on the power level feeding the individual radiators. The switching signals may be square wave o rectangular pulses of variable duty cycle or any other time-dependent modulation waveform. In multi-radiator HPA embodiments, suitable electronic switching means may be implemented which are independently modulating the power level of the individual radiators. As an example, in FIG. 21, the side view with parts cut away is shown of HPA 62 including the three direct radiators 66a, b and c. If a 3-channel power source (not shown in FIG. 21) is feeding them with steady-state power levels individually controlled inphase and amplitude, SAR spatial distributions such as 67 is obtained when energizing all the radiators with equal power, while 68 and 69 are obtained with 66a energized with smaller power than 66b and 66c, and vice-versa, respectively. In alternative CPA or SCPA or PCPA or MPA embodiments, suitable 2-channel electronic switching means are modulating the power level of the whole direct radiator set or of the whole exciter set to accomplish varying power level ratios between channels until the limiting working conditions of a pure multi-modal or pure direct heating fields are accomplished. It is to be noted that a further element of variance for a time-averaged SAR distribution is added to the above embodiments if the switching is carried out with switching times which are comparable with the mean lifetimes in each radiator configuration.

Tumors occur in a large variety of anatomical sites, and adequate apertures or treatment port configurations to produce specific heating fields would be useful in many clinical situations. Alternative embodiments for the treatment of tissues embedded in body surfaces exhibiting concave or convex curvatures are illustrated in FIGS. 22-24.

FIG. 22(a) shows a side view with parts cut away of an alternative embodiment of HPA 62a applied to cylindrical body surface 4a encompassing tumor 65. The aperture 2a of the BCW is conforming to the cylindrical curvature of 4a, with a set of straight direct line-radiators 46 of suitable length laying substantially parallel to the cylinder axis as much as the extension of 65 along this direction.

FIG. 22(b) shows side views with parts cut away of alternative embodiments of HPA 62b with radiators 46' now perpendicular to the cylinder axis and applied to same body surface 4a and same tumor 65 of FIG. 22(a). The BCW aperture 2a of this PPA is still conforming to the cylindrical curvature of 4a. The choice between HPA embodiments of FIGS. 22(a) and 22(b) for tumor 65 treatment is based on which one of them provides a field which matches best the tumor size or shape.

FIGS. 23 and 24 show side views with parts cut away of alternative embodiments of HPA 62c and 62d, respectively, applied to the treatment of a body surface with negative curvature 4b encompassing tumor 65. In FIG. 23, the convex aperture 2b of HPA 62c is conforming to the concave body cylindrical surface with the set 46 of direct line-radiators laying along the aperture 2b cylindrical shape for an efficient and penetrating treatment. In FIG. 24, the convex aperture 2b of PPA 62d is occluded by shield 61, with both aperture and shield conforming to the concave body surface. Treatment port 64 is cut through shield 61 to circumscribe the heating to tumor 65.

People skilled in the art will recognize that with a HPA exhibiting a flexible radiation shield with more than one treatment port, and having at disposal suitable mechanical means, the port configuration may be switched from one configuration to another to produce a time-varying heating field shape and orientation delivering a time-averaged SAR distribution over the tumor tissue.

In FIG. 25, a further PPA embodiment is illustrated to treat the superficial tumor 65 sitting on the side wall of a body cavity 4b. One aperture 2c is cut through the side wall of the cylindrical cross section BCW segment of endocavitary HPA 62e without interrupting totally the conductive wall, for making available the therapeutic field to 65. The fundamental $TE_{11}$ mode of BCW is energized with the $TE_{11}$ mode vector fields E and H lying as in FIG. 25. In this PPA embodiment, aperture 2c is a longitudinal slot on the BCW cylindrical wall. In alternative embodiments of endocavitary HPA working on the same fundamental mode, side apertures are instead cut through the BCW wall as transverse slots, and the modal field emerging from the aperture field will substantially be an E-field which might be superimposed to the direct field of suitable direct radiators.

FIG. 26 is a perspective view with parts cut away of toroidally shaped PPA embodiment 62f according to the invention, which is exhibiting a continuous inner cylindrical aperture 2d for the treatment of pseudo-cylindrical body segment 4c. This PPA is thus shaped with the configuration of a cylindrically distributed phased array. The body segment 4c is inserted into the hole of the doughnut shaped BCW 62f to be totally surrounded by circumferential aperture 2d for treatment of deep tumor 65. One or more sets of distributed exciters (not shown in FIG. 26) provide a modal field of radial symmetry. A suitable distortion of this PPA cylindrical configuration would give a heating enhancement on an eccentric tumor 65. In alternate embodiments, a set of direct radiators 46 is providing a localized field for the enhanced and circumscribed heating of tumor 65.

Additional EM fields may be superimposed to the heating field of a single HPA, to safely provide a locally enhanced temperature rise in cases where the heating field a single HPA is not adequate. This is the case when in need of producing a treatment field of specific contours and of sizes larger than the cross section of a single HPA or when effective treatment fields are required at depths higher than the penetration depth of a single HPA.

Multiple applicator embodiments comprise assembling one or more HPAs together with other applicators, either electromagnetic or non-electromagnetic, for producing global treatment fields which match those contours and sizes at the required depths.

Alternative embodiments of a multiple HPA system are the HPA phase arrays. In general, all the array power sources are synchronized at a single frequency and are phase coherent. The field of each array element is controlled in phase, amplitude and orientation and is directed over the target volume where a positive interference occurs which produces a locally useful heating enchancement.

Figure 27A:
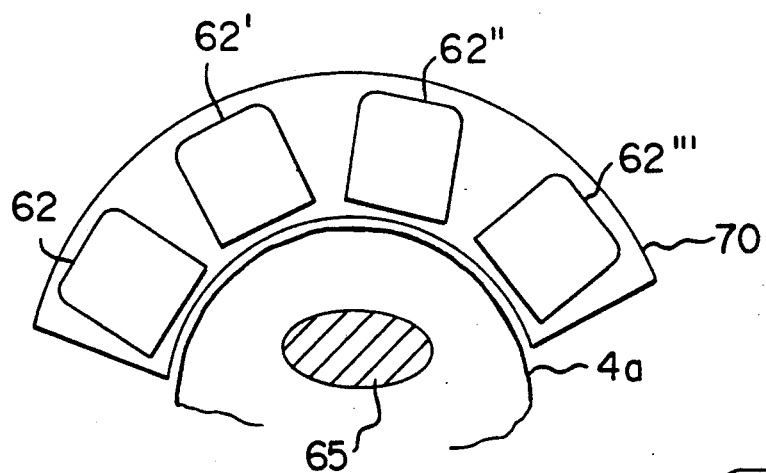
FIGS. 27(a) and (b) show schematic side views with parts cut away of alternative embodiments of hyperthermia discrete phased array applicators for the treatment of deep-seated tumors.

In FIG. 27(a), a side view with parts cut away is shown of the phased array embodiment 70 assembling the four HPAs: 62, 62', 62'', and 62'''. These are controlled to give positive interference of the four composite heating fields on deep-seated target tissue 65 that is the recipient of the temperature enhancement, while the convex access body tissue 4a is safely subject to an average HPA heating field intensity which corresponds approximately to one fourth of the total energy required for heating 65 by a single HPA.

Figure 27B:
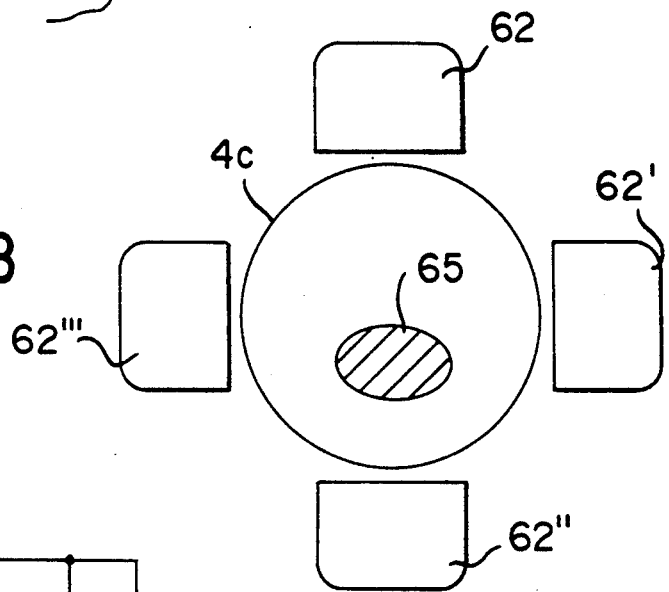

In FIG. 27(b), the top view with parts cut away, a further 4-element HPA phase array embodiment is shown. The array elements 62, 62', 62'', 62''' are surrounding the body 4c under treatment on a nearly circular disposition, and their relative phase and amplitude are controlled to give constructive interference over off-centered target 65. With both these embodiments, the effective penetration depth of the phased array is substantially higher than that of a single HPA. The treatment of body segments encompassing deep-seated masses is safer and more precise if the number of array elements if increased.

In alternate embodiments, planar or quasi-planar HPA phased arrays may be implemented as a means of improving the uniformity of a HPA applicator assembly, in those cases in which a large heating field size is required for a lesion on a quasi-planar body surface.

Figure 28A:
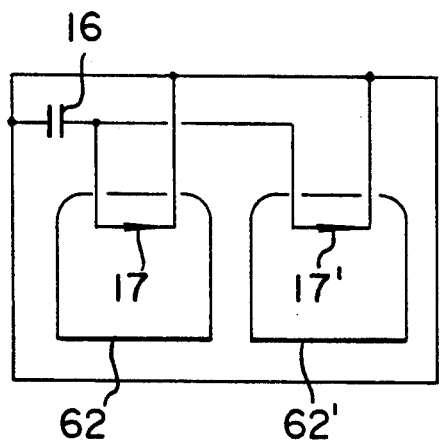
FIG. 28(a) and (b) show schematic side views with parts cut away of alternative embodiments of radiator feeding circuitry for assemblies of applicators.
Figure 28B:
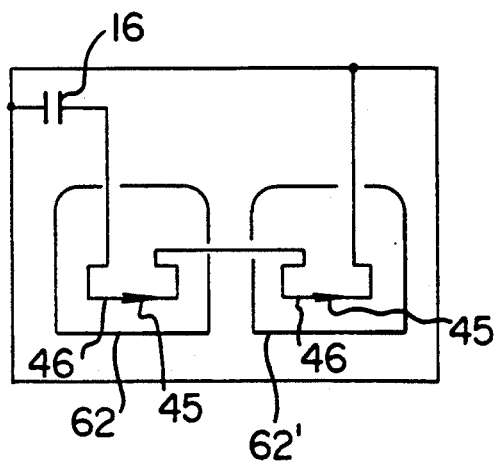

In FIG. 28, circuital embodiments are illustrated for feeding EM energy from a power source (not shown in FIG. 28) through matching means (not shown in FIG. 28) to a multiplicity of exciters as well as direct radiators of a 2-element HPA assembly which is working in the synchronous modality. In FIG. 28(a), a parallel embodiment is illustrated in which the radiators of HPAs 62 and 62' are energized by current lines 17 and 17', respectively, the intensity of which is drawn from a common resonant exciter circuit tuned by condenser 16. In FIG. 28(b), a series embodiment is illustrated, in which line radiators 46 and 46' of HPA 62 and 62', respectively, are energized by the same current intensity 45 drawn from the same circuit tuned by condenser 16. Such common feeding embodiments may be implemented for any multiple HPA system to synchronously energize exciters as well as direct radiators in the same or in different HPAs.

A further alternate multiple applicator embodiment is composed of plurality of HPAs, working at different frequencies.

The constructive interference principle may be used for the localized HPA heating enhancement of deep tissues below plane or quasi-plane body surfaces, for which a linear phased array made up of like elements is not adequate. The embodiment disclosed performs an effective heating enhancement of depth by equipping the HPA with auxiliary heating means of the utmost simplicity and practicality of operation. This principle will be illustrated for a low frequency embodiment with the help of FIG. 29, which is depicting an applicator system in which power sources and matching devices are not included.

In FIG. 29(a), a side view of HPA 62 aimed at the large and deep target volume 65 beneath the approximately flat body surface 4 is shown, together with the heating E-field $E_{PA}$ representative vector, giving rise to the 50 percent SAR contour, i.e. EFS, 71, which does not encompass completely tumor 65, as required for a successful treatment.

FIG. 29(b) shows the active auxiliary applicator (AA) 72, consisting of capacitive electrodes 73 and 73' applied to the same anatomic site (power source not shown). The AA is producing capacitive heating fields $E_c$ approximately parallel to the body surface. Because of site geometry, $E_c$ is substantially uniform and exhibits approximately the same phase across its cross section and gives rise to approximately the same phase across its cross section and gives rise to approximately uniform EFS 71' which, however, is not circumscribed to target 65.

In FIG. 29(c), a side view of an embodiment of the 2-stage applicator system obtained by assembling HPA 62 with auxiliary applicator 72 is schematically illustrated, in which the respective SAR distributions 71 and 71' are superimposed on the same site which includes target 65. If the individual power sources of both devices are coherent and controlled in phase and the $E_{PA}$ and $E_c$ fields have the same direction and phase over target volume 65, these interfere positively with a significant heat enhancement within the resulting EFS 71'', which exhibits an enhanced broad SAR maximum of variable depth and size, matching the depth and size of target volume 65 by adjusting the relative intensity direction and phase relationship of the two power sources.

In alternative embodiments, HPA and AA devices may both be energized by the same source by setting up suitable internal EM coupling means between them. A low frequency coupling embodiment is schematically illustrated in FIG. 29(d) with parts cut away, which refers to the same type of devices 62 and 72 of FIGS. 29(a) and 29(b), respectively. Energization of the passive circuit of auxiliary applicator 72' is accomplished by coupling this circuit to the magnetic component of the composite heating field of HPA 62, obtained by a suitable geometry of the applicator assembly. The resonant electric circuit of passive auxiliary applicator 72' includes electrodes 73 and 73', the inductive loop 74, the circuit tuning capacitance 75, and the body tissue between the electrodes, in which the AA current 76 flows. In the embodiment schematically illustrated in FIG. 29(d), 72' is substantially energized by the magnetic coupling of loop 74 to the magnetic field of current 45 of line radiator 46 of HPA 62. Thus, the closed electric circuit 72' of AA acts as the passive resonant secondary of a transformer in which the electric circuit of radiator 46 is the primary circuit. A positive interference between superimposed fields occurs since the current 76 induced in 72' by 62 results phase-coherent and with approximately the same phase of 45 of the latter device due to the highly resistive character of the resonant secondary. The power level energizing AA is easily controlled by adjusting the magnetic coupling between devices, which in turn controls the effective penetration of the whole hybrid HPA assembly.

By mechanical means incorporated in the apparatus, motion is imparted to the HPA for cyclically scanning the tissue under treatment in order to focus the heating field on a deep target volume while the energy is safely distributed over a wide access skin area. Other ways of cyclic scanning may be implemented so that a whole variety of tissue contours and sizes may effectively be treated by a single HPA, taking also into account the physical, electromagnetic or thermal heterogeneity of the tissues involved. More than one HPA may simultaneously be scanned over the tissue to be exposed in cases including lower power HPAs and very large size tissues. The scanning feature is made possible by the air-coupling distinctive feature of the HPA with the body tissue, which is not implementable in the prior art resonant aperture applicators. In all the scanning embodiments of the present invention, the therapeutic heating field of a HPA, or a part of it, is kept collimated over the tissue target by a suitable selection of the HPA cross section, aperture conformation, scan pathway and scan speed. All parts of the target tissue, supposedly heterogeneous, receive a specifically time-averaged heating field, the level of which is planned for bringing each part to its specific target temperature.

In a preferred scanning embodiment, the temperature of a target tissue at a depth can be raised to the therapeutic temperature, while the access and the normal tissues encompassing the target tissue remain at a lower temperature since their heating is intermittent.

Figure 30A:
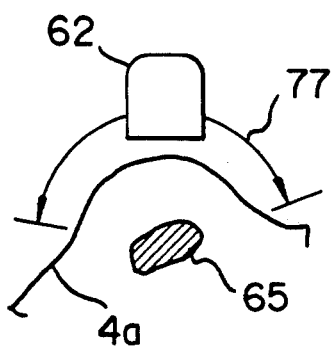
FIGS. 30(a)-(c) show schematic side views with parts cut away of embodiments of hyperthermia applicators provided with mechanical scanning means for improving the focusing of the EM energy in the treatment of deep-seated or heterogeneous tissues.

In FIG. 30(a), the side view is shown of this method employing HPA 62 provided with mechanical scanning means (not shown in FIG. 30(a)) which are impressing the approximately semi-circular trajectory 77 to 62 for continuously collimating the heating field over deep target volume 65 through the convex-shaped anatomic surface 4a.

Figure 30B:
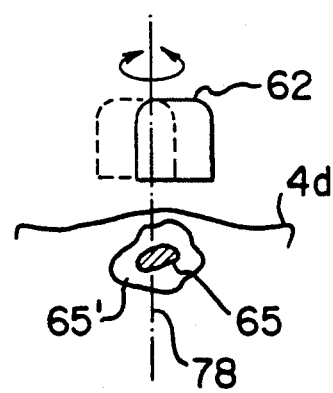

An alternative scanning embodiment is instead applied to a superficial target volume of cross section smaller than that of the HPA, as a means for obtaining a substantial temperature gradient between the target volume core and its periphery. In FIG. 30(b), HPA 62 is subject to an off axis rotatory motion around axis 78 centered on the target volume core 65 (rotatory means not shown in FIG. 30(b)) which is continuously subject to a part of the heating field of 62, while the target peripheral volume 65' is only intermittently subject to the other part of the heating field of 62.

Figure 30C:
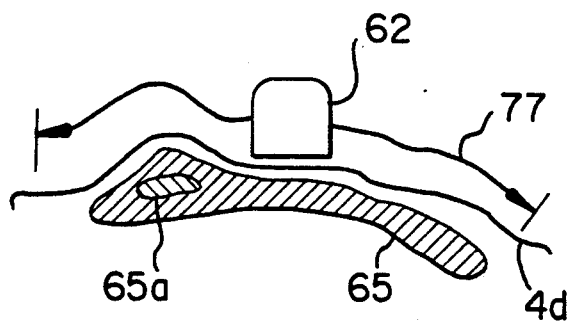

In FIG. 30(c), the side view is shown of an alternate scanning embodiment, which is aimed to heat the large size subcutaneous tissue 65 exhibiting an irregular contour, different thickness and depth and encompassing an heterogeneous tissue part such as 65a. HPA 62 is scanning over the irregular body surface 4d (scanning means not shown in FIG. 30(c)) with pathway 77 conforming to body surface 4d and covering all parts of 65 across its size in order to expose them to the heating field of 62. However, the scanning pathway will run at different speeds over the heterogeneous parts of tissue 65, the slower the speed the higher the time-averaged heat delivery over these parts, in order that each part of 65 reaches the established target temperature. The same result is obtained by a scanning pathway planned to pass over these heterogeneous parts with a different frequency, more frequent passages bringing higher level time-averaged heat delivery.

Thus the applicators of the present invention are suited to the localized hyperthermic treatment of a large variety of deep subcutaneous tumors as well as to the palliative treatment of a large variety of deep subcutaneous tissues which cannot be heated as effectively, or as simply, or at lower cost by current available heating equipment.

The treatment plans for the tumors would require exposure of the tumor tissue to a uniform temperature throughout the tumor mass for a definite interval of time. The local heating field distribution should therefore be shaped to take care of the EM and thermal heterogeneity of the tissues, including the presence of blood vessels and the large variety of anatomic access sites and of tumor shape, size, and depth. The HPAs may play an important role in cancer therapy for their improved penetration depth and safety features and for the flexibility in producing heating fields which are in-field adjustable by simple means in the clinical environment.

It will also be apparent that the design as well as the optimization of specific HPAs is useful for treatment superficial and subcutaneous tumors, among which skin tumors including melanomas, mammary carcinomas, brain tumors, head and neck carcinomas, lymph nodes, gynecological tumors and osteosarcomas.

Figure 31:
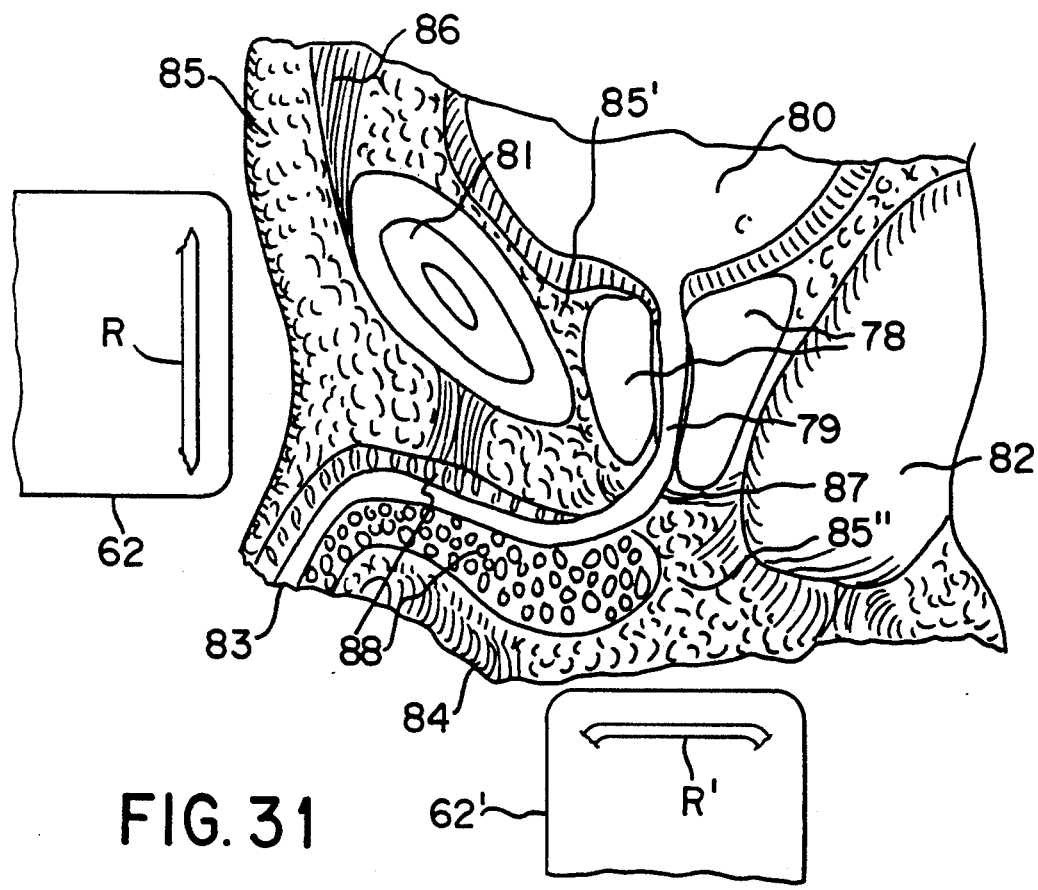
FIG. 31 is a schematic side view with parts cut away of a hyperthermia system embodiment for the treatment of the pelvic region and consisting of one abdominal and one perineal hyperthermia applicator which are configured at an angle.

With the help of FIG. 31, the HPA-body configuration may be usefully optimized for the external treatment of carcinomas in a complex anatomic region such as the pelvis, which are currently treated with difficulty and trauma with endocavitary applicators. The example illustrated in FIG. 31 shows embodiments for treating the prostatic carcinoma, but bladder carcinomas, and gynecological carcinomas may be treated as well as with predictable variants derived from such HPA configurations.

In FIG. 31, a schematic representation of a sagittal mid-section of the prostatic anatomic site is illustrated with indication of the significant anatomic parts: the prostate 78, the urethra 79, the bladder 80, the pubic bone 81, the rectal ampulla 82, the penile and testicular attachments 83 and 84, respectively.

From the abdominal heating pathway, the access tissues of significant anatomic size and with EM conditioning properties are first the subcutaneous abnominal adipose 85 followed by the bony pubic symphysis 81 and by thin tissue layer 85', in which small vessels, adipose and other tissues are imbedded, before getting at the anterior boundary of prostate 78. Both adipose and bony tissues are dry and as a result are almost transparent to the EM field of the HPA and absorb very little EM energy compared to the wet muscle tissues. The abdominal muscle tissue 86 is substantially sideways with respect to the main heating field pathway of HPA 62 and therefore neither interfere much with the treatment nor absorbing EM energy to an unsafe level. The prostatic tissue is a composite one and may be considered laying between fat and muscle tissues as far as EM absorption is concerned. Thin muscle, adipose, connective tissues and the vaxculature in the periprostatic space are not shown in FIG. 31 since their volume appears not to be relevant.

The separation of the HPA 62 aperture from the prostate anterior boundary is of a few centimeters, depending on the thickness of the adipose and this space is filled of substantially non-absorbing tissues in a window of a cross section comparable to that of the prostate, which allows the full penetration of the heating field of HPA 62 and its absorption by prostate lobes.

Prostate temperature enhancement may be obtained by conveying lossy materials, including many microscopic forms of ferrite suspended in a viscous liquid, up to the bladder bottom or in the prostatic uretha or in the rectal ampoule in direct contact with prostate lobes. Moreover, a flexible metallic radiation shield working as a reflecting surface may be placed in the rectal ampoule and in contact with the prostate posterior lobes for increasing the power absorbed by the latter.

The shorter perineal access pathway is used by HPA 62', the aperture of which is slightly V-shaped for patient comfort. Along this route perineal adipose tissue 85" is found which does not give rise to significant energy absorption. The muscular urogenital diaphragm 87 supports the prostate 78 and contributes, together with other surrounding musculature, to its temperature elevation. The urethra spongy tissue 88 is blood perfused tissue and therefore never overheated besides being only partially on the field route. The anal sphincter muscle 86' appears sideways the heating field route to the prostate and is eventually cooled by simple means.

It thus appears that the prostatic tissue R is within the safe heating range of both HPAs. Radiators R of HPA 62 and R' of HPA 62' are in general multiple radiators with such a size, conformation and configuration to help produce an EFS ranging from about 5 cm by 5 cm to about 7 cm by 7 cm at their respective heating depths. It is observed that such field sizes are easily accomplished by HPAs equipped with twin-line radiators of square configuration of approximately those dimensions.

For improved safety, HPA 62 and 62' may simultaneously be applied with superimposed heating fields at reduced individual power. One embodiment includes a 2-element phased array with phase coherent heating fields. An alternative embodiment includes two or more independent and higher power HPAs which are alternatively fired for avoiding the insurgence of hot spots. The penetration depth and the EFS of the 62, 62' assembly is substantially controlled by the relative configuration of the two applicators.

The adjustment of the proper relative position of HPA 62 and 62' of FIG. 31 and the operation of two independent systems may require complex operations that would be avoided with a single HPA. In the alternate heating method embodied in FIG. 32 for the treatment of prostate hyperplasia or adenocarcinomas, as well as for gynecological tumor treatment, HPAs 62 and 62' are integrated in the single 2-HPA embodiment 89 of FIG. 32. This includes radiators R and R' respectively integrated in the two sections of the orthogonal two-arm BCW waveguide 90 which is provided with apertures 2' and 2". The shielding pouch 91 in the inner bend of 90 is made to host penis and testis in the case of male patients. Moreover, shallow slots may be cut away on both sides of the applicator internal edge for allowing comfortable passage of internal thigh musculature. The series exciter 92 comprising exciters 31 and 31' supports a synchronized $TE_{10}$ mode in both arms of 90.

Figure 33:
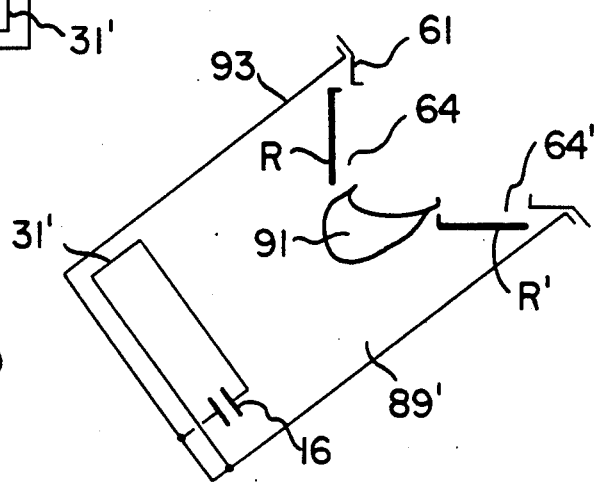
FIG. 33 is a schematic side view with parts cut away of an alternative embodiment of a dual port hyperthermia applicator designed for pelvic tissue treatment whereby the secondary heating field emitted by two ports cut away on the V-shaped radiation shield on the large cross section BCW aperture are collimated over the pelvic tissues via abdominal and perineal access routes.

The further alternate single-HPA embodiment 89' of FIG. 33, also designed for the treatment of pelvic tissues, includes a large size BCW segment 93 equipped with a single coil exciter 31. The concave-shaped radiation shield 61 is hosting pouch 91, and patient tailored treatment ports 64 and 64' are cut away on 61 and are acting as active apertures emitting phase-coherent secondary fields. The constructive pattern of the latter may be partially controlled by shaping said ports. Moreover, radiators R and R' are facing ports 64 and 64', respectively, with adjustable conformations and configurations to optimize the treatment field.

Figure 32:
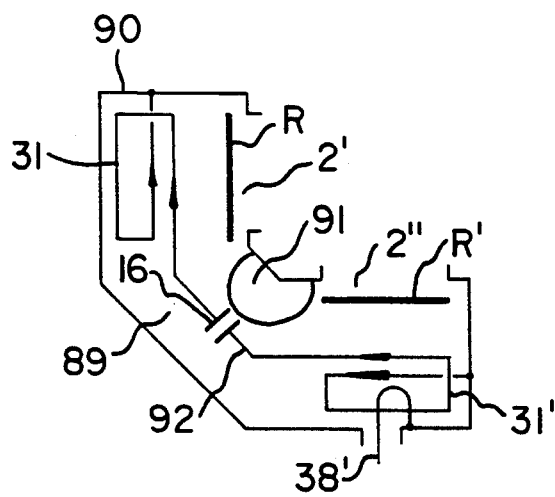
FIG. 32 is a schematic side view with parts cut away of an alternative embodiment of a dual applicator hyperthermia system suitable for pelvic tissue treatment via the abdominal and perineal access routes showing an orthogonal two-arm BCW body with a common exciting circuitry in which the apertures are configured at an angle.

For improved penetration, side-extended aperture HPA configurations such as that of FIG. 20(f) may usefully be employed in the HPA configurations of FIGS. 31 and 32.

It will be apparent to the people working in rehabilitation treatments with physical means such as ultrasound, microwaves, shortwave diathermy or magnetotherapy that all the HPA embodiments disclosed and those derived from them are useful also for palliation treatments of superficial musculature, subcutaneous tissues and joints. Subcutaneous localized heating is usually employed as an adjunct to other therapeutical treatments and it is prescribed for producing a large variety of beneficial effects, including increasing the extensibilty of collagen tissues, decreasing joint stiffness, producing pain relief, relieving muscle spasms, assisting in resolution of inflammatory infiltrates, edema and exudates and increasing blood flow (J. Lehmann; loc. cit.).

The HPA configuration of FIGS. 31, 32 and 33 and those derived from them are applicable to the safe palliative treatment of benign prostatic hypertrophia, to obtain a substantial volume reduction and consequent restoration of the urethral functionality. The beneficial effect of heat in cases of serious narrowing of the internal urethral meatus has been verified by applying heat via trans-rectal, trans-urethral and direct-contact capacitive applicators (A. Yerushalmi, Proc. IV Intl. Symp. Hyperth. Oncology, T. Sugahara and M. Saito eds., Vol. II, p. 69, 1989). However, the feasibility of these treatment approaches are bound to the safety of the access tissues, which is often jeopardized by the direct-contact of these delicate tissues with the applicators, a problem which would be solved with the adoption of HPA applicators.

It may be seen that a large variety of therapeutic field contours, sizes and penetration may be generated for optimized treatments by controlling the many parameters of these simple to operate, safe and efficient hybrid passband applicators. The versatility and simplicity of operation of any HPA will appear clear from a discussion of the experimental results of some heating patterns accomplished by HPA embodiments developed as examples of optimization of HPA therapeutic fields. The versatility and usefulness of the disclosed methods and apparatuses can be fully appreciated by these examples, which are not intended for limiting any further HPA configuration.

Figure 34A:
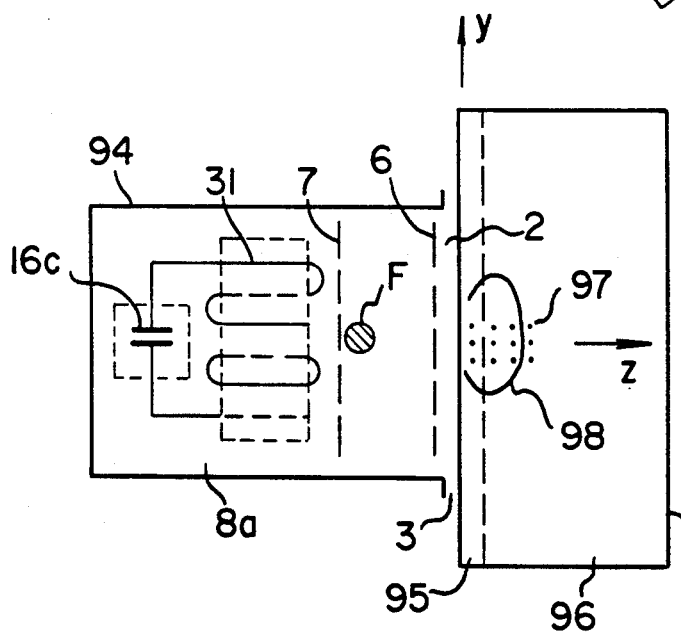
FIGS. 34 (a)-(e) show a schematic side view with parts cut away of a hyperthermia applicator embodiment coupled to a fat-muscle phantom and typical iso-SAR contours showing the effects of modal and direct heating fields superimposition.

In FIG. 34(a), the PPA hyperthermia test setup is schematically illustrated, showing the top view with parts cut away of PPA embodiment 8a of FIG. 1 including circular cross section BCW 94 with exciter 31 in the $L_{PE}$ range. The main evanescent mode energized by 31 is the dominant $TE_{11}$ mode, the cutoff frequency of which is about 840 MHz. In the following experiments, representative results are presented also of CPA, SCPA, and MPA embodiments.

BCW 94 is a cylindrical aluminum waveguide segment of 25 cm diameter and 30 cm length shorted at the back end and with aperture 2 laying parallel to the phantom fat surface with an air-gap 3 of 1 cm. A 3-turn coil solenoid 31 of diameter 9 cm and length 21 cm, built out of a 8 mm diameter multiwire copper conductor with the axis withdrawn about 12 cm from 2 is tuned to 27.12 MHz by variable vacuum condenser 16c and is fed by a power amplifier (not shown in FIG. 34) with a 30 second pulse of 800 W of EM power through a coupling and matching circuit (not shown in FIG. 34) and is cooled by a fan (not shown in FIG. 34) to ensure thermal stability and safety during operation. Bilayer phantom P is built up of materials simulating the EM behavior of body tissues with 2 cm thick superficial fat layer 95 and 20 cm thick muscle layer 96. The thermocouple array 97, sliding within parallel catheters, monitor the temperature steps $\Delta T$) following power pulses in both layers on a 1cm×1 cm×1 cm three-dimensional grid. From $\Delta T$ steps, longitudinal (x,y) and transverse (x,z) SAR distributions are calculated by computer interpolation and plotted as normalized iso-SAR maps.

The data illustrated in FIGS. 34(b)-41, are the 50 percent normalized SAR (x,y) contours at the depth of the SAR maximum value in the muscle tissue that hereinafter will be referred to as iso-SAR. From these SAR maps, and from those relative to (x,z) or (y,z) planes, the following treatment heating parameters may be evaluated: the effective (x,y) field size (EFS) coarsely evaluated by approximating the iso-SAR to an ellipsoid; the useful therapeutic volume (UTV) coarsely approximated by a rotation ellipsoidal volume; the penetration depth (pd), i.e., the depth along the z-axis from the phanthom exposed surface for which the SAR is 50 percent of the value measured at 1 cm depth within the muscle; the relative fat layer overheating factor (OF) defined by: $OF = (\Delta T_f / \Delta T_m)$, with temperature step $\Delta T_f$ measured at the fat layer midpoint and referred to the measured highest muscle $\Delta T_m$ step. The heating efficiency (HE) parameter is evaluated as the ratio between the average power deposited within the UTV to the total power delivered by the HPA and gives an indication of the focusing power of the HPA. Iso-SAR contours are schematically illustrated within front views of BCW 94 aperture trace, together with traces of the direct radiator (x,y) conductor pattern. In the following, like numerals refer to like parts, and reference is made to FIG. 34(a), illustrating the HPA equipped by a pure exciter, and to the drawings illustrating the further radiators employed, which are preferentially line radiators laying parallel to the body surface. Unless otherwise stated, the position of the latter inside the waveguide is fixed at 0.5-1 cm from the aperture, i.e., in the $L_{PR}$ range, and the air gap is fixed at about 1 cm. It has been found that under these experimental conditions, the contribution of the modal field to the composite field is never above 25 percent. Higher or lower direct and modal field contributions may well be accomplished changing the efficiency of the exciters or direct radiators according to the methods disclosed in the invention.

Figure 34B:
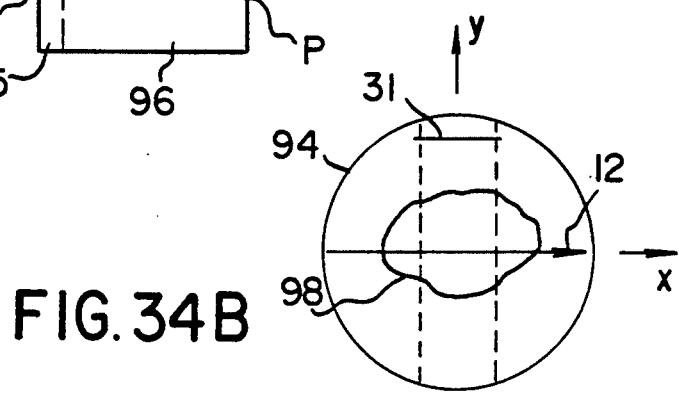

The first four experiments (see FIGS. 34(a)--(e)) are designed to demonstrate the principle of superpostion of modal and direct fields. In FIG. 34(a), the (x,z) is iso-SAR 98 of PPA 8a is shown. In FIG. 34(b), the (x,y) iso-SAR 98 of PPA 8a is shown to have an approximately ellipsoidal shape prolonged along the x-axis of the E-field 12 of the $TE_{11}$ mode of BCW 94. The results show a PD of 4 cm, a significantly high overheating factor (~2), and a low heating efficiency (~2%). The EFS and UTV obtained for this PPA are not significantly changed with other exciters of same symmetry, and are representative of the BCW employed, following closely textbook $TE_{mn}$ mode power density patterns. The mode filter efficiency has been checked, and it appears that HE decreases of an order magnitude by electrically connecting a simple $TE_{11}$ mode filter wire F as in FIG. 34(a), which verifies that $TE_{11}$ is the mode substantially excited by 31.

The integration in 8a of single-line (SL) direct radiator 99a at −7 cm from the aperture, i.e., in the distal end of the $L_{RE}$ range, gives the SCPA embodiment 8c of FIG. 1, and the (x,y) iso-SAR 98 of FIG. 34(c) is generated by the composite heating field resulting from the superimposition of the SCPA modal and direct fields. The SAR ellipsoid is rotated about 45° with respect to that of PPA in FIG. 34(c) account of the orthogonal configuration of 99a with respect to 31 and to the approximately equal weight of the two composite field components. A number of improvements are observed with respect to the PPA by virtue of the constructive effects caused by superimposing of coherent fields. The OF is significantly reduced of about one half, and penetration is improved as well the heating efficiency. The (x,z) iso-SAR is not shown for this and following experiments, since all of them have similar shapes, and the given PD values suffice.

In a further experiment, the crossed direct field contribution is increased by shifting SL 99a up to the BCW 94 aperture in the LPR range to accomplish a CPA configuration. The iso-SAR 98 of FIG. 34(d) is thus obtained, which shows the expected further rotation of the iso-SAR ellipsoid. The heating parameters exhibit significant improvements, with the muscle layer reaching higher temperature than the thick fat layer and the heating efficiency is doubled. Moreover, the more focused UTV ellipsoid is now lying along the SL 99a direction. These results are confirmed by a further experiment (FIG. 34(e)) in which the SL radiator 99b is now parallel to the exciting currents 31. The iso-SARs 98 of FIGS. 34(d)–(e) confirm the preponderance of this direct field to alter the shape and size of the composite field cross section. In this CPA configuration, the relative contribution to power deposition within the UTV by the two field components is about 4:1 in favor of the direct field, on account of the direct radiators being closer to the phantom.

The further four experiments are examples of how to increase the EFS and UTV of a CPA by shaping the direct field employing more than one radiator of varying conformation and configuration. In FIGS. 35(a)–(d) the iso-SAR contours 98 are relative to the following direct radiators: short SL 99c, narrow and long Twin-Line (NTL) 51a, wide and long twin-line (WTL) 51b and large radius concave Twin-Line (CTL) 51c, respectively. In FIG. 35(d), contour 100 is included for the 90 percent SAR value to show the heating uniformity of the device in a substantial part of the UTV. The results show a corresponding increase in EFS and UTV in the above order. The smallest fat overheating and the highest heating efficiency are exhibited by the NTL and WTL embodiments, while the highest penetration is shown by the CTL device. These trends are confirmed by further experiments and are to be ascribed to the constructive phase-coherence effects of the direct fields of the TL radiator pair superimposed to the modal field heating pedestal.

The CPA embodiment of FIG. 35(c) has been used to test the penetration dependance as a function of the air-gap to about 2 cm. The results (not shown here) confirm a PD not smaller than 4.5 cm in all cases. Furthermore, experiments with the CPA equipped with NTL and CTL radiators, respectively, show the effects of increasing the adipous layer to 3.5 cm, with the numerical data showing a substantial non-influence of any practical values of human fat layer thickness on heating parameters. Heating efficiency is smaller, consistently with the larger CPA-muscle tissue separation. The relative iso-SAR contours are approximately the same as those of FIGS. 35(b) and (d), respectively. These results were confirmed and show the efficiency of the HPAs to heat with safety tissues lying in or just beneath the subcutaneous fat below irregular body surfaces of adipous patients without any direct contact with the applicator.

Another useful feature of the hybrid CPAs according to the invention is evidenced, whereby the asymmetric SL radiator 99b configured close to the aperture edge (FIG. 36) exhibits iso-SAR 98 which is asymmetric, as shown by SAR profile 101 along the central x-axis (FIG. 37). The value of other heating parameters are comparable with those for the symmetric SL configuration. This edge effect feature may easily be amplified and used when heating irregular shaped or heterogeneous tissues.

In FIGS. 38(a)–(f), examples are given of how to optimize the conformation, the configuration and the phase of a 2-line radiators of a CPA to accomplish composite heating fields of cross section to match tissue lesions of varying sizes and non-regular contours. The outcome of these experiments follow a common trend with regard to the heating parameters (PD>4 cm; OF~1; HE>5%).

FIG. 38(a) shows the iso-SAR 98 and the 80 percent SAR contour 102 of a CPA equipped with the orthogonal configuration of SL radiators 99 and 99' energized with currents in the same direction 45 and 45' and of same intensity, respectively. It is seen that the phase coherent constructive interference of the two directly radiated components produces a sharp SAR maximum oriented along the SL bisectrix. The heating efficiency is the best so far obtained and fat is not overheated. A very sharp SAR edge effect is also present at the common origin of the radiators.

FIGS. 38(b) and (c) show iso-SAR contours 98 of a CPA equipped with SL radiators 99 and 99' at an angle smaller than 90° and energized with currents in the same direction 45 and 45', respectively. These have different intensity with 45 of higher intensity than 45'. In FIG. 38(b), both 99 and 99' are in the $L_{PR}$ range at ~0.5 cm from the aperture of the CPA, showing the iso-SAR 98 maximum closer to SL 99 on account of the higher current intensity flowing along this radiator. In FIG. 38(c), SL 99 is withdrawn inside the BCW at 3 cm from the aperture and falls within the $L_{RE}$ range, with 99' still at ~4 cm from the aperture within the $L_{PE}$ range. The iso-SAR 98 is now of larger size and more symmetric between SLs for the equalization of the field intensities on the tissue due to the longer distance from the tissue of the more energized SL 99. FIG. 38(d) shows the iso-SAR 98 and 98' and the respective 90 percent SAR contours 103 and 103' of a CPA equipped with orthogonal line radiators 99 and 99', respectively. These are energized with currents of opposite phase 45 and 45', respectively, and of same intensity. It is seen that the phase coherent destructive interference of the directly radiated components produces a central SAR minimum and two well defined maxima below the radiators bring rise to a bean-shaped iso-SAR. In FIG. 38(e), analogous results are obtained by out of phase currents by symmetric concave radiators 51c and 51c'. In FIG. 38(f), the iso-SAR 98 and the 90 percent SAR contour 103 of a CPA equipped with a C-shaped line radiator are shown. It is seen that a phase coherent destructive interference of the field components directly radiated by the currents flowing in opposite direction 45 and 45' in the parallel line terminals produce a central SAR minimum and a bean-shaped iso-SAR pattern. From all the results of FIG. 38, it appears that this principle may be exploited in a large variety of further HPA radiator configurations to produce iso-SAR to match many sizes and shapes of tissue lesions.

In FIG. 39, the large radius planar coil radiator 38d is generating an annular heated region delimited by inner and outer iso-SAR contours 98 and 98', respectively. The SAR maximum is defined by the 90 percent SAR contour 103 close to the loop hot end. The data shows a significant penetration improvement to 5 cm, a good heating efficiency and an acceptable fat overheating right below the SAR maximum and very large EFS and UTV. It appears that by a further boostering of the modal field, by additional direct radiators or by a small eccentric rotary scanning, a uniform composite field of any large size is accomplished with this very simple HPA configuration.

In FIG. 40, the iso-SAR 89 is shown for a CPA equipped with sheet current direct radiator 46a. The heating data are comparable to those obtained by a SL radiator with however, a heating efficiency twice as good and an absolutely negligible fat heating relative to the muscle tissue, which makes this CPA very safe for critical tissue clinical situations. In changing the frequency to 13.56 MHz, the iso-SAR as well as almost all the other parameters do not change appreciably. The efficiency is smaller on account of the smaller effectiveness but the penetration improves appreciably, as expected.

In FIG. 41, two MPA configurations of BCW 46 of rectangular 20 cm×40 cm aperture cross section and a 20 cm depth show iso-SAR 98a and 98b when excited in the $TE_{10}$ and $TE_{01}$ modes by SL 99d and 99e in the $L_{RE}$ range, respectively. It appears that for the $TE_{10}$ mode (FIG. 41(a)), 98a is only slightly larger than 98 of SL 99b (FIG. 34(e)) of same SL length of a smaller aperture HPA; however, penetration and fat overheating are significantly improved, as expected for having increased the relevant BCW cross section. For the $TE_{01}$ mode (FIG. 41(b)), the 98b length increases proportionally to the SL 99e length increases proportionally; however, its width is smaller than those that have been obtained with SL radiators in other BCWs (see FIG. 35(a)). The penetration is not improved, as expected for not having increased the relevant BCW dimension for this mode, as done in the case of FIG. 41(a).

Further SAR contours in a very large variety of sizes, shapes, orientations and depths may be accomplished by alternative HPA embodiments of the present invention which follow directly or indirectly from the principle disclosed according to the size, contours and multiplicity of BCWs apertures to the intrinsic SAR distributions of the modal and direct fields to the relative frequency and EM power energizing the exciters and direct radiators, to the conformation and configuration and position of the exciters and radiators in their respective active ranges, and to the relative phase of their currents.

In Table II, representative results accomplished with single-dipole (SD) and SL direct radiators measured under prior art conditions, i.e., in open air or encapsulating in a shielding metal box of size (22 cm×5 cm and 8 cm depth) close to those reported by previous authors (R. H. Johnson et al., loc. cit., 1987). It is to be noted that the box aperture depth by the latter authors are too small to properly excite evanescent modes and penetrate strong near fields which are detrimental to penetration. These results are compared with those of dipole-RA and Line-RA (FIG. 15(a)) according to the present invention, also reported in Table II, to show the improvements brought about by the disclosed RA devices. The phantom and the measurement conditions were those of the setup illustrated in FIG. 34(a), modified for the dipole-RA and line-RA measurements by placing exciter 31 by the BCW aperture and placing $TE_{11}$ mode filter rod back of the radiators and parallel to them. All the radiators were tested under the same conditions. Stray fields were measured with E- and H-field monitoring equipment.

to 45 percent of that of those disclosed in the present invention, with the lowest values for the radiators encapsulated in a metal box.

Moreover, the results of the stray E or H field intensity measurements at the radiator sides at 50 cm from the radiator conductors, under 100W of EM power feeding, show that these prior art devices present non-negligible EM hazards. Additional measurements on other HPA configurations show even lower levels of stray radiation on account of the retracted radiator position inside the BCWs and a consistently improved freedom from EM hazards.

While various embodiments of the present invention have been shown and described herein for purposes of illustration, it will be apparent that other variations and embodiments are considered to fall within the scope of the defined invention.

What is claimed is:

1. An electromagnetic heating method for the localized heating treatment of body tissues to therapeutic temperatures by exposing said tissues to an EM heating field produced by a hybrid passband applicator (HPA) comprising:

producing an electromagnetic power source with an output level, the frequency of said source ranging from about 0.1 MHz to 2450 MHz;

positioning a below cutoff waveguide segment having one end terminated by an active treatment aperture;

positioning a plurality of sets of resonant radiating elements inside said waveguide segment;

positioning a first set of resonant radiating elements within said waveguide segment to substantially work as pure exciters producing a multi-modal heating field propagating through said active treatment aperture;

positioning a second set of resonant radiating elements within said waveguide segment to substantially work both as exciters and direct radiators producing a multi-modal heating field and a direct heating field, respectively, both fields propagating through said active treatment aperture;

matching said sets of radiating elements to said power source;

tuning said sets of radiating elements to the frequency of said power source;

controlling the output level of said power source to each of said sets of resonant radiating elements; and matching electromagnetically said active treatment

TABLE II

|  | dipole radiator | | | | | line radiator | | | |
|---|---|---|---|---|---|---|---|---|---|
|  | PD (cm) | $\Delta T_f/\Delta T_m$ | HE % | H (A/m) | E (V/m) | PD (cm) | $\Delta T_f/\Delta T_m$ | HE % | H (A/m) | E (V/m) |
| Prior art: | | | | | | | | | | |
| metal box | 3.8 | 2.8 | .5 | .1 | 150 | 3.9 | 1.0 | 1 | .4 | 200 |
| open air | 4.0 | 1.5 | 1 | .2 | 75 | 3.9 | 1.1 | 2 | .4 | 210 |
| Present invention: | | | | | | | | | | |
| RA (Cyl. BCW) | 4.2 | 1.2 | 3.3 | .04 | 20 | 4.3 | .8 | 4.5 | .04 | 30 |

The Table II data shows that significant improvements are obtained with the dipole-RA and line-RA according to the invention for the main heating parameters, i.e.. PD, fat overheating and heating efficiency. For the latter parameter, it is seen that the prior art radiators exhibit an efficiency which is from 13 percent aperture to said body tissue for optimizing the energy transfer to the body tissue and directing over said body tissue the composite heating fields resulting from the superposition of said multi-modal and direct heating fields.

2. The electromagnetic heating method as claimed in claim 1 including the steps of:
inserting low loss high susceptibility ferrite materials in high H-field density regions of said waveguide segment;
adjusting the position of said ferrite material within said waveguide segment to produce the required time and spatial profiles of said heating fields; and
automatically controlling said matching and said tuning of said resonant radiating elements to said power source.

3. The electromagnetic heating method as claimed in claim 1 including the steps of:
inserting low loss high permittivity dielectric materials in high E-field density regions of said waveguide segment;
adjusting the position of said dielectric material within said waveguide segment to produce the required time and spatial profiles of said heating fields; and
automatically controlling said matching and said tuning of said resonant radiating elements to said power source.

4. The electromagnetic heating method as claimed in claim 1 including the step of controlling said localized heating by:
constructing said waveguide segment with an aperture cross section of variable size, shape or curvature;
adjusting said waveguide aperture size, shape or curvature to produce the required time and spatial profiles of said heating fields; and
automatically controlling said matching and said tuning of said resonant radiating elements to said power source.

5. The electromagnetic heating method as claimed in claim 1, wherein said matching electromagnetic of said active treatment aperture to said body tissues when said body tissues present a curved anatomic surface, includes the step of:
shaping said active treatment aperture to substantially conform to said curvature of said body surface.

6. The electromagnetic heating method as claimed in claim 1 wherein said localized heating comprises the additional steps of:
inserting a conductive radiation shield occluding conformally said active aperture of said waveguide segment; and
cutting at least one port on said radiation shield, said port acting as a secondary source generating a port-specific heating field, said secondary field being controlled by adjusting the size, shape or position of each port on said radiation shield.

7. The electromagnetic heating method as claimed in claim 1 wherein said body tissues define a body cavity and the localized heating comprises the additional steps of:
providing said waveguide segment with a cross section size and shape to match the size and shape of said body cavity; and
cutting at least one port in a wall of said waveguide, each port acting as a secondary source generating port-specific heating field and adjusting the size, shape or position of each port on said wall for heating specific portions of the tissues sitting in said body cavity.

8. The electromagnetic heating method as claimed in claim 1, wherein said localized heating comprises the additional steps of:
providing a principal heating field generated by said hybrid passband applicator;
providing at least one auxiliary and coherent heating field generated by at least one passive auxiliary electromagnetic heating device energized by an adjustable electromagnetic coupling with said hybrid passband applicator;
superimposing said principal and auxiliary heating fields preferentially over said tissues to be exposed; and
controlling said adjustable electromagnetic coupling to provide a relative phase, amplitude and orientation of said principal and auxiliary heating fields to generate a positive interference pattern preferentially localized over said tissues to be exposed to produce enhanced temperature elevations.

9. The electromagnetic heating method as claimed in claim 1 wherein said body tissues to be exposed include tumors to be treated to specific therapeutic temperature elevations.

10. The electromagnetic heating method as claimed in claim 1 wherein said body tissues to be exposed include superficial musculature, subcutaneous tissues and joints and said heating produces palliation.

11. The electromagnetic heating method as claimed in claim 1 wherein said body tissue to be exposed includes the hypertrophic prostatic tissue and said heating produces palliation.

12. The electromagnetic heating method for the localized heating treatment of body tissues to therapeutic temperatures by exposing the tissue to an EM heating field comprising the steps of;
providing a principal heating field through the generating of a hybrid passband applicator;
providing at least one auxiliary and coherent heating field generated by at least one active auxiliary electromagnetic heating device energized by an independent power source;
superimposing said principal heating field and said at least one auxiliary and coherent heating field over said tissues to be exposed; and
controlling the relative phase, amplitude and orientation of said principal and auxiliary heating fields to generate a positive interference pattern preferentially localized over said tissues to be exposed to produce enhanced temperature elevations.

13. An electromagnetic heating method for the localized heating treatment of body tissues to therapeutic temperatures by exposing said tissues to an EM heating field produced by a hybrid passband applicator (HPA) comprising:
producing an electromagnetic power source, the frequency of said source ranging from about 0.1 MHz to 2450 MHz;
positioning a below cutoff waveguide segment having one end terminated by an active treatment aperture;
positioning resonant radiating means inside said waveguide segment to produce multi-modal and direct heating fields;
matching said resonant radiating means to said power source;
turning said resonant radiating means to the frequency of said power source;

controlling output level of said power source to said resonant radiating means; and matching electromagnetically said active treatment aperture to said body tissue for optimizing the energy transfer to the body tissue and directing over said body tissue the composite heating fields resulting from the superposition of said multi-modal and direct heating fields.

14. An electromagnetic heating apparatus for heating treatment of localized body tissues to therapeutic temperatures by exposing said tissues to an EM heating field produced by a hybrid passband applicator (HPA) comprising:

an electromagnetic power source, the frequency of said source ranging from about 0.1 MHz to 2450 MHz;

a below cutoff waveguide structure having one end terminated by an active treatment aperture connected to said power source;

a plurality of sets of resonant radiating elements positioned inside said waveguide structure;

a first set of resonant radiating elements positioned within said waveguide structure adapted to work as pure exciters producing a multi-modal heating field propagating through said active treatment aperture;

a second set of resonant radiating elements positioned within said waveguide structure adapted to work both as exciters and direct radiators producing a multi-modal heating field and a direct heating field, respectively, both fields propagating through said active treatment aperture;

matching means matching said sets of resonant radiating elements to said power source:

tuning means tuning said sets of resonant radiating elements to the frequency of said power source;

control means controlling the output level of said power source to each of said sets of resonant radiating elements; and means to electromagnetically match said active treatment aperture to said body tissue for optimizing the energy transfer to the body tissue and directing over said body tissue the composite heating fields resulting from the superposition of said multi-modal and direct heating fields.

15. An electromagnetic heating apparatus as claimed in claim 14 wherein said resonant radiating elements are lumped constant radiators comprising coil radiators and lumped capacitive parts working in the low end of said frequency range.

16. An electromagnetic heating apparatus as claimed in claim 14 wherein said resonant radiating elements are lumped constant radiators comprising magnetic dipole radiators and lumped capacitive parts working in the low end of said frequency range.

17. An electromagnetic heating apparatus as claimed in claim 14 wherein said resonant radiating elements are lumped constant radiators comprising line current radiators and lumped capacitive parts working in the low end of said frequency range.

18. An electromagnetic heating apparatus as claimed in claim 14 wherein said resonant radiating elements are lumped constant radiators comprising lumped capacitive parts embodied by a common variable tuning capacitor shared by lumped inductive parts connected in series, parallel or a series-parallel network working in the low end of said frequency range.

19. An electromagnetic heating apparatus as set forth in claim 14 wherein said resonant radiating elements are lumped constant radiators comprising lumped inductive parts and lumped capacitive parts with flexible current carrying conductors; means for controlling time dependence of said localized heating, said means for controlling time dependence of said localized heating comprising:

mechanical control means adjusting the position and configuration of said resonant radiating elements to produce the specific time and spatial profiles of heating fields; and control means for the automatic control of said matching and said tuning of said resonant radiating elements to said power source.

20. An electromagnetic heating apparatus as claimed in claim 14 including means for controlling said localized heating comprising electronic multi-channel modulating means for individually adjusting the output level of said power source to each of said sets of resonant radiating elements to produce specific time and spatial profiles of said heating fields.

21. An electromagnetic heating apparatus as claimed in claim 14 wherein said resonant radiating elements are lumped constant radiators comprising lumped inductive parts and lumped capacitive parts, said lumped inductive parts being electromagnetically coupled together and sharing a common matching circuit to said power source, said matching circuit consisting of a loop terminating a feeding cable from said power source, said loop being magnetically coupled to said inductive parts of said lumped radiators, said matching circuit including a sliding joint means for modifying the extent of said magnetic coupling.

22. An electromagnetic heating apparatus as claimed in claim 14 wherein said resonant radiating elements are constructed as lumped constant radiating elements working in the low end of a frequency range of said power source and said matching and tuning means couple said lumped constant radiating elements to said power source, said lumped constant radiating elements being positioned inside a shielded box outside said waveguide structure.

23. An electromagnetic heating apparatus as claimed in claim 14 wherein said resonant radiating elements are constructed as lumped constant radiators working in the low end of said frequency range and said matching and tuning means for coupling said lumped resonant radiating elements to power sources are positioned beyond pure exciting range of said waveguide structure.

24. An electromagnetic heating apparatus as claimed in claim 14 wherein said resonant radiating elements are lumped constant elements working in the low end of said frequency range and consist of lumped capacitive parts and inductive parts with one electrode of said capacitive parts being grounded to a waveguide wall for limiting stray electromagnetic fields.

25. An electromagnetic heating apparatus as claimed in claim 14 wherein said resonant radiating elements are constructed as lumped constant elements working in the low end of said frequency range and consist of symmetric lumped inductive parts and symmetric lumped capacitive parts with a mid-point of said symmetric lumped inductive parts or a central electrode of said symmetric lumped capacitive parts being grounded to a waveguide wall for limiting stray electromagnetic fields.

26. An electromagnetic heating apparatus as claimed in claim 14 wherein two radiating elements of said second set work as mixed exciter/radiating elements.

27. An electromagnetic heating apparatus as claimed in claim 14 including means for adjusting the relative configuration of said resonant radiating elements with respect to each other and to a wall of said waveguide structure.

28. An electromagnetic heating apparatus as claimed in claim 14 including means for adjusting the position of said resonant radiating elements with respect to said waveguide active aperture.

29. An electromagnetic heating apparatus as claimed in claim 14 wherein said waveguide structure has a circular cross-sectional aperture.

30. An electromagnetic heating apparatus as claimed in claim 14 wherein said waveguide structure has a rectangular cross-sectional aperture.

31. An electromagnetic heating apparatus as set forth in claim 14 wherein the cross section of said waveguide structure is adjusted to a selected dimensional shape by the addition of cross-sectional transition waveguide segments.

32. An electromagnetic heating apparatus as claimed in claim 14 wherein mode filters of specific symmetry and configuration are inserted inside said waveguide structure.

33. An electromagnetic heating apparatus as claimed in claim 14 including means to operate said power source so that the resonant radiating elements can work at a plurality of frequencies.

34. An electromagnetic heating apparatus as claimed in claim 14 wherein said means for controlling the electromagnetic energy to said radiating elements from said power source comprise multi-channel feeding devices incorporating power level control means and phase shifting means in each feeding channel.

35. An electromagnetic heating apparatus as claimed in claim 14 including an air gap space between said aperture and said body tissue, said air gap space being of adjustable width.

36. An electromagnetic heating apparatus as claimed in claim 14 wherein a dielectric bolus of adjustable thickness, dielectric permittivity and magnetic susceptibility covers said waveguide structure aperture, said dielectric bolus being adapted to be interposed between the aperture and said body tissue.

37. An electromagnetic heating apparatus as claimed in claim 14 for localized heating on a target volume localized inside a quasi-cylindrical body segment wherein said waveguide structure is a radial waveguide of toroidal shape, said active aperture being a circumferential aperture on an inner conductive wall of said radial waveguide and adapted to surround said quasi-cylindrical body segment.

38. An electromagnetic heating apparatus as claimed in claim 14 including:
mechanical means for scanning conformally said hybrid passband applicator over said body surface; and
means for programming and executing the pathway, speeds and duty cycle of said scanning while continuously keeping the heating field of said applicator aimed to tissues to be exposed.

39. An electromagnetic heating apparatus for heating treatment of localized body tissues to therapeutic temperatures by exposing said tissues to an EM heating field produced by a hybrid passband applicator (HPA) comprising:
an electromagnetic power source, the frequency of said source ranging from about 0.1 MHz to 2450 MHz;
a below cutoff waveguide structure having one end terminated by an active treatment aperture connected to said power source;
a plurality of sets of resonant radiating elements positioned inside said waveguide structure comprising;
a first set of resonant radiating elements positioned within said waveguide structure adapted to work as pure exciters producing a multi-modal heating field propagating through said active treatment aperture; and
a second set of resonant radiating elements positioned within said waveguide structure adapted to work both as exciters and direct radiators producing a multi-modal heating field and a direct heating field, respectively, both fields propagating through said active treatment aperture;
matching means matching said sets of resonant radiating elements to said power source;
tuning means tuning said sets of resonant radiating elements to the frequency of said power source;
control means controlling electromagnetic energy from said power source to each of said sets of resonant radiating elements;
means to electromagnetically match said active treatment aperture to said body tissue for optimizing the energy transfer to the body tissue and directing over said body tissue, the composite heating fields resulting from this superposition of said multi-modal and direct heating fields; and
at least one additional assembly of like element phased array to that of said hybrid passband applicator, said hybrid passband applicator generating a total heating field, said total heating field being preferentially directed over said body tissue, all of said like elements of said phased array being coherent with one another and individually controlled in phase, amplitude and orientation to give rise to a positive interference pattern and to preferential enhanced temperature elevations of said body tissue.

* * * * *